(12) United States Patent
Hasenwinkel et al.

(10) Patent No.: US 8,383,734 B2
(45) Date of Patent: Feb. 26, 2013

(54) MULTI-SOLUTION BONE CEMENTS AND METHODS OF MAKING THE SAME

(75) Inventors: Julie M. Hasenwinkel, Manlius, NY (US); Jeremy L. Gilbert, Fayetteville, NY (US); Danieli C. Rodrigues, Syracuse, NY (US); Rebecca Bader, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 405 days.

(21) Appl. No.: 12/764,664

(22) Filed: Apr. 21, 2010

(65) Prior Publication Data

US 2010/0273911 A1    Oct. 28, 2010

Related U.S. Application Data

(63) Continuation-in-part of application No. 12/372,425, filed on Feb. 17, 2009, which is a continuation-in-part of application No. 11/779,025, filed on Jul. 17, 2007.

(60) Provisional application No. 60/807,551, filed on Jul. 17, 2006.

(51) Int. Cl.
*C08L 33/12* (2006.01)
*A61L 24/06* (2006.01)

(52) U.S. Cl. ........ 525/302; 523/116; 523/115; 523/117; 525/902; 525/228; 525/259; 525/261; 525/330.3; 525/330.5; 525/330.6

(58) Field of Classification Search ............... 523/116, 523/115, 117; 525/902, 228, 259, 261, 330.3, 525/330.5, 330.6, 302
See application file for complete search history.

(56) References Cited

U.S. PATENT DOCUMENTS

| | | |
|---|---|---|
| 3,928,499 A | 12/1975 | Tomalia |
| 4,396,476 A | 8/1983 | Roemer |
| 4,791,150 A | 12/1988 | Braden |
| 4,969,888 A | 11/1990 | Scholten |
| 5,334,626 A | 8/1994 | Lin |
| 5,728,583 A | 3/1998 | Kawakami |
| 5,902,839 A | 5/1999 | Lautenschlager |
| 2004/0220297 A1 | 11/2004 | Bonfield et al. |
| 2008/0039586 A1* | 2/2008 | Hasenwinkel et al. ....... 525/192 |
| 2009/0239970 A1 | 9/2009 | Rodrigues et al. |
| 2010/0273911 A1 | 10/2010 | Hasenwinkel et al. |

FOREIGN PATENT DOCUMENTS

| | | |
|---|---|---|
| WO | WO9824398 A1 | 6/1998 |
| WO | WO2006090379 A1 | 8/2006 |

OTHER PUBLICATIONS

Jayachandran KN, Chatterji, Synthesis of dense brush polymers with cleavable grants, European Polym J 2000; 36: 743-749. particles in a polymer melt, Macromolecules 2002; 35: 5171-5182.

(Continued)

*Primary Examiner* — Mark Kaucher
(74) *Attorney, Agent, or Firm* — Frederick J M Price; Bond Shoeneck & King

(57) ABSTRACT

The present invention relates to bone cements and, more particularly, to acrylic-based orthopedic bone cements, their use in spinal applications, and methods for making the same. An embodiment of the present invention provides a method of grafting PMMA brushes on cross-linked PMMA nanospheres comprising at least one of the following steps: performing a hydrolysis reaction of surface methyl ester groups of said cross-linked PMMA nanospheres to form surface carboxylic acid groups of said cross-linked PMMA nanospheres; forming a 2-aminoethyl acrylate compound; coupling said surface carboxylic acid groups of said cross-linked PMMA nanospheres with said 2-aminoethyl acrylate compound to form a coupled compound with an initiating site; and grafting said PMMA brushes onto said initiating site. Another embodiment of the present invention includes an orthopedic bone cement including cross-linked PMMA nanospheres comprising PMMA brushes prepared by this method, and a monomer, wherein polymer to monomer ratio is between about 1:1 and 1.3:1.

17 Claims, 26 Drawing Sheets

OTHER PUBLICATIONS

Borukhov I and Leibler L, Enthalic stabilization of brush coated Lin Ek and Gast AP, Self consistent field calculations of interactions between chains tethered to spherical interfaces. Macromolecules 1996; 29: 390-297.

Lewis, Alternative acrylic bone cement formulations for cemented arthroplasties: present status, key issues, and fracture prospects. J Biomed Mater Res B: Appl Biomater 2008, vol. 84B, pp. 301-319.

Lewis, Injectable bone cements for use in vertebroplasty and kyphoplasty: state-of-art-review. J Biomed Mater Res B: Appl Biomater 2006, vol. 76B, pp. 456-468.

Lieberman, et al., Vertebroplasty and Kyphoplasty: filler materials, Spine J 2005, vol. 5, pp. 305S-316S.

Jarvik, et al., Vertebroplasty: Learning more, but not enough. Spine 2003, vol. 28(14), pp. 1487-1489.

Belkoff, et al., Temperature measurement during polymerization of polymethylmethacrylate cement used for vertebroplasty, Spine 2003, vol. 28(14), pp. 1555-1559.

Belkoff, et al., The biomechanics of vertebroplasty. The effect of cement volume on mechanical behavior, Spine 2001, vol. 26(14), pp. 1537-1541.

Molloy, et al., Effect of cement volume and placement on mechanical property restoration resulting from vertebroplasty, AJNR Am J Neuroradiol 2005, vol. 26, pp. 401-404.

Phillips, Minimally invasive treatments of osteoporotic vertebral compression fractures, Spine 2003, vol. 28, pp. S45-S53.

Deb, et al., The effect of cross-linking agents on acrylic bone cements containing radiopacifiers, Biomaterials 2001, vol. 22, pp. 2177-2181.

Jasper, et al., Material properties of various cements for use with vertebroplasty, J Mater Sci, Mater Med 2002, vol. 13, pp. 1-5.

Lewis, et al., Influence of the radiopacifier in an acrylic bone cement on its mechanical, thermal, and physical properties: Barium sulfate containing cement versus iodine-containing cement, J Biomed Mater Res B, Appl Biomater 2005, vol. 73B, pp. 77-87.

Van Hooy-Corstjens, et al., Mechanical behavior of a new acrylic radiopaque iodine-containing bone cement, Biomaterials 2004, vol. 25, pp. 2657-2667.

Kurtz, et al., Static and fatigue mechanical behavior of bone cement with elevated barium sulfate content for treatment of vertebral compression fractures, Biomaterials 2005 vol. 26, pp. 3699-3712.

Ginebra, et al., Mechanical performance of acrylic bone cements containing different radiopacifying agents, Biomaterials 23, 2002, pp. 1873-1882.

Ruckenstein, Eli and Chung, Dennis Byungip, Surface Modification by a Two-Liquid Process Deposition of A-b Block Copolymers, Department of Chemical Engineering, State University of New York, Buffalo, NY, pp. 170-185.

Wang, et al., Fracture toughness of acrylic bone cements, J Mater Science 1989, vol. 24, pp. 3725-3738.

Vallo, et al. Mechanical and fracture behavior evaluation of commercial acrylic bone cements, Polym Int 1997, vol. 43, pp. 260-268.

Persson, et al., Radiopacity of tantalum-loaded acrylic bone cement, Proc I Mech E 2006, vol. 220, pp. 787-791.

Hasenwinkel, et al., A novel high-viscosity, two-solution acrylic bone cement: effect of chemical composition on properties, J. Biomed Mater Res 1999, vol. 47, pp. 36-45.

Hasenwinkel, et al., Effect of initiation chemistry on the fracture toughness, fatigue strength, and residual monomer content of a novel high-viscosity, two solution acrylic bone cement, J Biomedical Materials Research 2002, vol. 59, pp. 411-421.

ASTM F451-99a, 2007e1, "Standard Specification for Acrylic Bone Cement", ASTM International, West Conshohocken, PA, www.astm.org.

Kjellson, et al., Bone cement X-ray contrast media: a clinically relevant method of measuring their efficiency, J Biomed Mater Res B: Appl Biomater 2004, vol. 70B, pp. 354-361.

Pascual. et al., New aspects of the effect of size and size distribution on the setting parameters and mechanical properties of acrylic bone cements, Biomaterials 1996, vol. 127, pp. 509-516.

Sun, et al., Model filled polymers. VII: Flow behavior of polymers containing monodisperse crosslinked polymeric beads. Polym Eng Sci 1992, vol. 32(12), pp. 777-785.

Li, et al., Model filled Polymers: The effect of particle size on the theology of filled poly(metyl methacrylate) composites. Polym Eng Sci 2004, vol. 44, pp. 452-462.

Miller, S.T., Polymer Brushes, Science, New Series, vol. 251, No. 4996 (Feb. 22, 1991), pp. 905-914.

Burton, et al., Vertebroplasty and Kyphoplasty: a compressive review, Neurosurg Focus 2005, vol. 18(3), pp. 1-7.

Lewis, Properties of acrylic bone cements: State of the art review, J Biomed Mater Res B: appl Biomater 1997, vol. 38B, pp. 155-182.

Verlan, et al., Temperature elevation after vertebroplasty with polymethyl-methacrylate in the goat spine, J Biomed Mater Res B: Appl Biomater 2003, vol. 67B, pp. 581-585.

Hass, et al., A characterization of polymethylmethacrylate bone cement, J Bone Joint Surg A 1975, vol. 57, pp. 380-391.

Meyer, et al., On the settling properties of acrylic bone cement, J Bone Joint Surg A 1973, vol. 55, pp. 149-156.

Krause, et al., The viscosity of acrylic bone cements, J Biomed Mater Res 1982, vol. 16, pp. 219-243.

Chaffey, et al., Shear thinning and thickening rheology II, Volume fraction and size of dispersed particles, J Col Interf Sci 1977, vol. 59(I), pp. 63-75.

Probstein, et al., Bimodal model of concentrated suspension viscosity for distributed particle sizes, J Rheol 1994, vol. 38(4), pp. 811-829.

Hernandez, et al., Influence of powder particle size distribution on complex viscosity and other properties of acrylic bone cement for vertebroplasty and kyphosplasty, J Biomed Mater Res B; Appl Biomater 2006, vol. 77(B), pp. 98-103.

C.I. Vallo, et al. "Influence of cross-linked PMMA beads on the mechanical behavior of self-curing acrylic cements", Journal of Biomedical Materials Research. Part B: Applied Biomaterials, 2004, vol. 70B, No. 2, pp. 407-416. See the abstract.

* cited by examiner

Two-solution bone cement compositions

Micro/Nano compositions

| P:M ratio | Pb:Pl ratio | Pt mass | Pl mass | Pb mass | Pl:M ratio | Min Pb:Pl for Pl:M < 0.5 |
|---|---|---|---|---|---|---|
| 1 | 1 | 100 | 50 | 50 | 0.5 | 1 |
| 1 | 1.5 | 100 | 40 | 60 | 0.4 | |
| 1 | 2 | 100 | 33.33 | 66.67 | 0.33 | |
| 1.1 | 1 | 110 | 55 | 55 | 0.55 | 1.2 |
| 1.1 | 1.5 | 110 | 44 | 66 | 0.44 | |
| 1.1 | 2 | 110 | 36.67 | 73.33 | 0.37 | |
| 1.2 | 1 | 120 | 60.00 | 60.00 | 0.60 | 1.4 |
| 1.2 | 1.5 | 120 | 48.00 | 72.00 | 0.48 | |
| 1.2 | 2 | 120 | 40.00 | 80.00 | 0.40 | |
| 1.3 | 1 | 130 | 65.00 | 65.00 | 0.65 | 1.6 |
| 1.3 | 1.5 | 130 | 52.00 | 78.00 | 0.52 | |
| 1.3 | 2 | 130 | 43.33 | 86.67 | 0.43 | |
| 1.4 | 1 | 140 | 70.00 | 70.00 | 0.70 | 1.8 |
| 1.4 | 1.5 | 140 | 56.00 | 84.00 | 0.56 | |
| 1.4 | 2 | 140 | 46.67 | 93.33 | 0.47 | |

*mass relative to 100 ml MMA

| term | definition |
|---|---|
| P:M ratio | mass/vol ratio of total polymer to monomer |
| Pb:Pl ratio | mass ratio of polymer beads to linear polymer |
| Pt mass | total polymer mass (equals Pl + Pb) |
| Pl mass | mass of linear polymer |
| Pb mass | mass of crosslinked beads |
| Pl:M ratio | mass/vol ratio of linear polymer to monomer |

FIG. 32

MULTI-SOLUTION BONE CEMENTS AND METHODS OF MAKING THE SAME

CROSS REFERENCE TO RELATED APPLICATIONS

The present application claims priority to U.S. application Ser. No. 12/372,425, filed on Feb. 17, 2009, which claims priority to U.S. application Ser. No. 11/779,025, filed on Jul. 17, 2007, which claims priority to U.S. Provisional Application No. 60/807,551, filed on Jul. 17, 2006; all of the foregoing patent-related document(s) are hereby incorporated by reference herein in their respective entirety(ies).

BACKGROUND OF THE INVENTION

1. Field of the Invention

The present invention relates to bone cements and, more particularly, to acrylic-based (i.e., the use of polymers and monomers based on methacrylic acid) orthopedic bone cements, their use in spinal applications, and methods for making the same.

2. Description of the Related Art

The clinical use of total joint replacements in the United States is expected to rise precipitously over the next twenty-five years, projected to the level of over 4 million primary total knee and hip replacement procedures performed annually by the year 2030. The number of revision surgeries for both total hips and total knees will likely double over this time period as well. Thus, the demand for high performance bone cement is rapidly growing.

One of the critical factors in the clinical success of total joint arthroplasty is stable fixation of the prosthesis; which, in a majority of cases, is accomplished through the application of PMMA-based bone cement. While bone cement has been used clinically since the early 1960's and there are many commercially available powder-liquid cement compositions, the material continues to be scrutinized for the role that it plays in aseptic loosening of total joint prostheses.

Multi-solution acrylic bone cements (typically referred to as a two-solution bone cement, but which could have more than two solutions) have surfaced as an alternative to powder-liquid cement, using the same chemical constituents as current commercial formulations. This cement consists of PMMA powder pre-dissolved in methyl methacrylate (MMA) monomer, to form two separate solutions; one containing the initiator, benzoyl peroxide (BPO) and the other containing the activator, N,N-dimethyl-p-toluidine (DMPT), which react to initiate polymerization of the MMA when the solutions are mixed. These solutions have an initial viscosity similar to that of powder-liquid cement in the dough stage, therefore they can be simultaneously mixed and delivered to the surgical site via a single, closed system. This not only simplifies the surgical procedure by eliminating the multi-stage process of cement mixing and delivery, but also reduces the extent to which the properties of the polymerized cement depend on variations in surgical technique. Two-solution bone cement compares favorably to commercial cements (Simplex P and Palacos R) both in its mechanical properties and biocompatibility.

While the two-solution bone cement concept is a promising alternative to powder-liquid cements, it has several drawbacks in its current form, primarily related to the increase in monomer concentration necessary to form viscous solutions of dissolved linear PMMA. Many important properties of the cement, including the polymerization exotherm, residual monomer concentration, volumetric shrinkage, and shrinkage-induced porosity, are directly proportional to the initial monomer concentration. These properties represent the key areas where two-solution cement currently does not perform as well as commercial powder-liquid cements. The reduction of monomer in two-solution bone cement is limited by the solution viscosity, which is controlled by both the concentration and molecular weight (MW) of the PMMA in solution. Increasing the P:M ratio, without decreasing the MW of the PMMA, increases solution viscosity, yielding cements, which are difficult to mix and deliver. Significantly decreasing the PMMA MW in order to increase the P:M ratio, however, leads to a marked decrease in the mechanical properties of the polymerized cement.

Poly(methyl methacrylate) bone cements have primarily evolved for the fixation of total hip and knee joint arthroplasties. Over 30 commercially available plain acrylic cement brands are currently approved for use in cemented arthroplasties. Some of these commercial cements have been tailored recently for the treatment of vertebral compression fractures using kyphoplasty (KP) and vertebroplasty (VP) procedures. Percutaneous VP and KP stabilize vertebral compression fractures resulting from osteoporosis and other lesions. Both procedures involve injection of modified formulations of bone cements into the fractured vertebrae in order to restore functionality and reduce pain. The desirable properties of injectable bone cements for the treatment of vertebral compression fractures (using VP and KP procedures) comprise high radiopacity, suitable viscosity to allow easy handling and injectability, high compressive strength, low curing temperature and longer setting times (e.g., about 15 minutes and mechanical properties resembling those of non-osteoporotic vertebrae). Currently, no standardized formulations meet the viscosity criteria for use in the spine. Therefore in order to lower viscosity and increase the working time of commercial cements, surgeons usually alter the polymer-to-monomer ratio recommended by manufacturers. Lower viscosities are desirable to enhance penetration of the cement into the small pores of the cancellous bone, thereby increasing the strength of the interface between bone and cement mantle. Likewise, lower exotherm temperatures may provide protection from heat damage, avoiding thermal necrosis of surrounding soft tissues. Formulations that set more slowly would allow not only extended time for heat dissipation, but also better workability and handling.

Standard two-solution bone cement (STBC, as described in U.S. Pat. No. 5,902,839) has emerged as an alternative to current powder-liquid formulations. According to studies carried out by Hasenwinkel et al (cited below) the standard two-solution cement has the advantage of being porosity free and have higher flexural strength and modulus of elasticity. One limitation of this material is the high initial viscosity of the dough, which makes injection of the cement through small needles and cannulas difficult. STBC has the advantage of presenting higher flexural strength and modulus of elasticity, being less porous than commercial formulations. It also has the advantage of being mixed in a simpler manner, which allows metered delivery of material in a closed system (see Hasenwinkel J M, Lautenschlager E P, Wixson R L, Gilbert J L, A novel high-viscosity, two-solution acrylic bone cement: effect of chemical composition on properties, J. Biomed Mater Res 1999; 47:36-45; and Hasenwinkel J M, Lautenschlager E P, Wixson R L, Gilbert J L, Effect of initiation chemistry on the fracture toughness, fatigue strength, and residual monomer content of a novel high-viscosity, two-solution acrylic bone cement, J Biomedical Materials Research 2002; 59, 411-421). However, one limitation of the use of this formulation in KP and VP is the higher initial viscosity of the cement and relatively short setting time (varying from 7 to 9 minutes from the beginning of mixing).

It is well known that acrylic bone cements are non-Newtonian or pseudoplastic fluids that undergo shear thinning with increasing shear rates, presenting significant differences in the flow behavior among compositions. The clinical significance of highly pseudoplastic cements is related to the fact that the material can be subjected to rapid thinning, which consequently enhances flow through a delivery system and into the interstices of the bone. Another important factor affecting viscosity of bone cements is the incorporation of polymer particles or fillers in the cement matrix. Polymer particle size and its distribution (polydispersity), volume fraction and particle-particle interaction are factors that determine the rheological behavior of dispersed systems. Even though the effects of the size and size distribution of PMMA particles on the properties of acrylic bone cements are discussed in the literature, most of these studies involved the application of commercial samples of linear PMMA used in powder-liquid formulations. For example, Pascual et al showed that the use of PMMA particles with average diameter in the 50-60 µm range and with wide size distribution significantly changed the maximum polymerization exotherm and setting characteristics of cement formulations (see Pascual B, Vazquez B, Gurruchaga M, Goni I, Ginebra M P, Gil F J, Planell J A, Levenfeld B, Roman J S, *New aspects of the effect of size and size distribution on the setting parameters and mechanical properties of acrylic bone cements*, Biomaterials 1996; 17:509-516). Likewise, Hernandez et al discussed the influence of powder size distribution on the properties of cements used in KP and VP showing that cements with a high proportion of large PMMA beads (~118 µm) to small beads (~70 µm) presented suitable viscosity behavior and injectability (see Hernandez L, Gurruchaga M, Goni I, *Influence of powder particle size distribution on complex viscosity and other properties of acrylic bone cement for vertebroplasty and kyphoplasty*, J Biomed Mater Res B: Appl Biomater 2006; 77B:98-103).

The application of acrylic bone cement for the treatment of vertebral compression fractures requires visualization of the material flow under image fluoroscopy. In order to enhance contrast, it is common practice to alter the composition of commercial cements by increasing the amount of radiopacifier. Radiopacity of the cements is achieved by the addition of contrast radiopacifier materials, such as $BaSO_4$ and $ZrO_2$, which are vastly discussed in the literature to cause alterations in the biological and mechanical properties of cements. The effect of $BaSO_4$ on the static and dynamic properties of bone cements is somewhat contradictory. Most studies have reported deleterious effects of $BaSO_4$ in the mechanical performance of cements due to clumping resulting from the heterogeneity and incompatibility of the polymeric matrix and inorganic salt. For example, Wang et al pointed out that the addition of $BaSO_4$ to Simplex P lowers the ultimate tensile strength and fracture toughness of the material (see Wang C T, Pilliar R M, *Fracture toughness of acrylic bone cements*, J Mater Sci 1989; 24:3725-38). Ginebra et al showed a similar trend in tensile strength by the presence of $BaSO_4$ in comparison to a radiolucent cement (see Ginebra M P, Albuixech L, Fernandez-Barragan E, Aparicio C, Gil F J, San Roman J, Vazquez B, Planell J A, *Mechanical performance of acrylic bone cements containing different radiopacifying agents*, Biomaterials 23; 2002:1873-1882). On the contrary, Kurtz et al and Jasper et al reported a significant increase in the compressive properties as a function of increasing $BaSO_4$ content (see Kurtz S M, Villarraga M L, Zhao K, Edidin A A, *Static and fatigue mechanical behavior of bone cement with elevated barium sulfate content for treatment of vertebral compression fractures*, Biomaterials 2005; 26:3699-3712; Jasper L E, Deramond H, Mathis J M, Belkoff S M, *Material properties of various cements for use with vertebroplasty*, J Mater Sci: Mater Med 2002; 13:1-5). Vallo et al reported that the presence of radiopacifier fillers improved fracture toughness by promoting interactions between the crack and the second phase dispersion, and Deb et al concluded that the presence of the inorganic phase did not seem to affect the tensile strength of acrylic cements (see Vallo C I, Cuadrado T R, Frontine P M, *Mechanical and fracture behavior evaluation of commercial acrylic bone cements*, Polym Int 1997; 43:260-268; Deb B and Vazquez B, *The effect of cross-linking agents on acrylic bone cements containing radiopacifiers*, Biomaterials 2001; 22:2177-2181). In view of these contradictory opinions, alternative radiopacifiers and methods have been explored, as for example, the use of tantalum-based cements, iodine containing monomers and substitution of $ZrO_2$ for $BaSO_4$, which seems to have less detrimental effects due to the size and morphology of the particles that allow for better adhesion within the matrix. Current commercial cements that utilize Zr02 include Palacos R (Zimmer, Inc.).

Previous technology showed a synthetic pathway protocol regarding surface modification of beads with several steps including: 1. amidation of the surface methyl esters with ethanolamine; 2. reaction of the hydroxyl groups of the modified beads with acryloyl chloride leading to the formation of carbon-carbon double bonds on the surface of the beads, which ultimately acted as a free radical site; 3. reaction with potassium persulfate followed by free radical polymerization of methyl methacrylate at the surface.

Description Of the Related Art Section Disclaimer: To the extent that specific publications are discussed above in this Description of the Related Art Section or elsewhere in this application, these discussions should not be taken as an admission that the discussed publications are prior art for patent law purposes. For example, some or all of the discussed publications may not be sufficiently early in time, may not reflect subject matter developed early enough in time and/or may not be sufficiently enabling so as to amount to prior art for patent law purposes. To the extent that specific publications are discussed above in this Description of the Related Art Section (as well as throughout the application), they are all hereby incorporated by reference into this document in their respective entirety(ies).

SUMMARY OF THE INVENTION

It is therefore a principal object and advantage of the present invention to provide a multi-solution bone cement incorporating more PMMA.

It is another object and advantage of the present invention to provide a multi-solution bone cement having improved mechanical properties.

The viscosity and setting parameters of acrylic bone cements used for restoring vertebral compression fractures are critical factors in VP and KP procedures. Thus, it is another object and advantage of the present invention to provide a multi-solution bone cement which exhibits lower viscosities to allow easy handling and injectability, high compressive strength, low curing temperature and longer setting times. This object and advantage is designed to overcome the difficulty of forcing the "dough" through small needles upon application, and to reduce the risk of cementing the multi-solution bone cement during surgery.

It is a further object and advantage of the present invention to provide a multi-solution bone cement which exhibits high radiopacity.

In accordance with the foregoing objects and advantages, an embodiment of the present invention provides multi-solution bone cements which include cross-linked PMMA beads, thereby providing for a significant increase in the polymer-to-monomer (P:M) ratio. As a result, the bone cements of the present invention have reduced polymerization exotherms, volumetric shrinkage, shrinkage induced porosity, and residual monomer, all of which are advantageous for the clinical performance of the cement. When surface modified with unsaturated carbon double bonds, the cross-linked PMMA beads exhibit improved interfacial adhesion between the beads and the polymerized cement matrix by allowing them to participate in the polymerization reaction and thus be covalently bound to the matrix, thereby improving the mechanical properties of cements made with functionalized beads. One advantage of the multi-solution bone cements of the present invention is the ability to adjust viscosity by means of the P:M ratio and the ratio of cross-linked beads to linear polymer in the composition.

In accordance with an embodiment of the present invention, the present invention also comprises multi-solution bone cements made with PMMA-PMMA spherical brush polymers. The density and molecular weight of PMMA chains grafted onto cross-linked PMMA beads are controlled through the atom transfer radical polymerization process, along with the concentration of these particles in the monomer solutions, thereby enabling the manufacture of bone cements with tailored viscosities.

As noted supra, multi-solution bone cements consist of linear polymer chains consisting of acrylate (e.g., PMMA) polymer dissolved into MMA monomer. The viscosity of these cements is dictated by the combination of polymer molecular weight and polymer-to-monomer ratio. Increasing either of these quantities will increase the viscosity. In order to obtain workable cement viscosities, the combination of suitable molecular weight and polymer to monomer ratio are typically in the 80,000 g/mol lower limit Mw and about 0.95:1 polymer-to-monomer ratio. Since typical powder liquid cements are in the range of 1.8:1 P:M ratio, changes in two solution cement are needed to raise the P:M ratio while still preserving suitable viscosity.

In accordance with an embodiment of the present invention, modified multi-solution cements contain an additional element that can comprise either cross-linked PMMA beads or reactive cross-linked beads (where reactive double bond groups are placed on the surface of the beads) that are added to the multi solution mixture. The amount of crosslinking within the beads, the ratio of linear polymer (Pl) to bead-based polymer (Pb), and the bead size will all affect the viscosity of the mixture. Furthermore, varying crosslinking concentration (i.e., the amount of crosslinking agent used to create the cross-linked PMMA beads—e.g., EGDMA) within the polymer beads will affect the amount of monomer uptake and swelling that can take place within the beads which will, in turn, affect the overall viscosity of the system. Additionally, cements can be made by the addition of spherical polymer brushes alone to MMA.

In addition to the advantages previously described, the bone cements of an embodiment of the present invention are significantly simpler for the surgeon to mix and apply in the operating room compared to current powder-liquid bone cements. Simplification of this process eliminates much of the technique-dependent variability in bone cement properties. Additionally, the polymerization of multi-solution based bone cements is initiated by mixing the two or more components through a static mixing nozzle (current design) or some comparable device. The cement can be simultaneously mixed and delivered to the surgical site of application if desired. The use of a disposable mixing nozzle allows for metered dosing from a single batch of cement. For example, a desired volume of material can be mixed and delivered in order to cement the first component of a total knee replacement. The mixing nozzle can then be removed and at the appropriate time, a new nozzle can be attached to mix the cement for the second component of the knee implant. The flexibility that this type of approach affords the surgeon is highly advantageous from a delivery standpoint because it allows for multiple cement applications at different times during a single surgical procedure, from a single batch or dose of cement. This type of approach is not possible with conventional bone cements because an entire batch must be mixed at one time, thus starting the polymerization reaction and limiting the time with which the surgeon can work with the cement before it cures. Bone cements of different viscosities are desirable for different surgical procedures (e.g., khyphoplasty vs. total hip cementation vs. total knee cementation). The ability to customize cements for the various market niches within the field of orthopedics is therefore highly desirable.

In accordance with an additional embodiment of the present invention, the viscosity of standard two-solution bone cement (STSBC) can be manipulated by subtle changes in the polymer-to-monomer ratio and by the incorporation of cross-linked poly(methyl methacrylate) PMMA microspheres or nanospheres in the polymer phase. In a preferred embodiment, addition cross-linked PMMA particles can be added at specific ratios, e.g., in the 20-100 μm and 300-330 nm size-range (which was evaluated on the rheological properties and setting behavior of novel multi-solution cements, as discussed in the Examples below). The addition of the cross-linked PMMA particles was observed to reduce the initial viscosity in comparison to the standard formulation, and to improve the setting properties of multi-solution cements by increasing setting time and reducing maximum exotherm significantly.

In accordance with an additional embodiment of the present invention, the material properties of multi-solution bone cements of an embodiment of the present invention composed of cross-linked poly(methyl methacrylate) PMMA microspheres or nanospheres added to the linear polymer phase at a fixed ratio were assessed for formulations with increasing concentrations of zirconium dioxide ($ZrO_2$). The optical density was measured for three-cement formulations (standard two-solution containing linear PMMA (STSBC), modified two-solution containing cross-linked PMMA microspheres and modified cement containing cross-linked PMMA nanospheres) and compared to KyphX HV-R containing 30% barium sulfate ($BaSO_4$). Static compression testing was performed with formulations containing 0, 5, 20 and 30% $ZrO_2$. As discussed in the Examples section infra, cements prepared with cross-linked beads exhibited significantly higher compressive strength ($p<0.05$) than standard-two solution cement at increasing radiopacifier concentrations and significantly higher compressive strength ($p<0.05$) than KyphX. The strength of these bone cement formulations increased with increasing concentration of radiopacifier. In contrast, the addition of higher amounts of radiopacifier to the standard two-solution cement composition had a detrimental effect on the measured properties of the material. Cements containing cross-linked PMMA particles exhibited matrices with even dispersion of radiopacifier and reduced porosity in comparison to KyphX and standard two-solution formulations. Furthermore, cement viscosity was increased by the addition of increasing concentrations of radiopacifier in the modified two-solution cements, while the maximum polymerization exotherm and setting time of these materials were decreased. The results indicate that the addition of high concentrations of $ZrO_2$ significantly affects the properties of two-solution bone cements acting as a reinforcing phase when cross-linked spheres are added to the cement solution. These materials were observed to be suitable for vertebroplasty applications.

The present invention recognizes that there are potential problems and/or disadvantages in the above-discussed synthetic pathway regarding surface modification of beads. Several drawbacks were associated with this synthetic pathway, including difficult purification of ethanolamine modified beads, which required extraction in methanol over several days. Ethanolamine is a relatively difficult reagent to remove from particles requiring, besides extraction, several filtration and washing steps. Furthermore, the high reaction temperature necessary for direct amidation of the surface methyl esters with ethanolamine led to the formation of numerous impurities and side-products. As a result, addition of carbon-carbon double bonds to the hydroxyl sites via esterification with acryloyl chloride was not facilitated. $^1$H-NMR measurements revealed that only a few sites on the surface of the beads are modified with carbon-carbon double bonds when employing this technique. This observation confirmed that this method did not allow for efficient modification of the nanospheres surface, which translated into a low degree of grafting and formation of high concentrations of homopolymer into the final product. Various embodiments of the present invention may be advantageous in that they may solve or reduce one or more of the potential problems and/or disadvantages discussed above in this paragraph.

In addition to the advantages previously described, it is an object and advantage of the present invention to provide a novel synthetic pathway (method) for more efficient surface modification of cross-linked PMMA nanospheres for grafting of PMMA nanospherical brushes onto the nanospheres at high densities (PMMA-g-PMMA).

Other objects and advantages of the present invention include: 1. higher grafting efficiency of PMMA nanospherical brushes, 2. simpler steps required for modification of the surface of the cross-linked PMMA beads on larger scales, 3. higher yields, 4. easier control of the reaction parameters, 5. product workup can be facilitated by simple evaporation, centrifugation or filtration, 6. at least one step (preferably more than one step, e.g., three steps) of the method can be performed at room temperature, and 7. bone cements prepared with these PMMA nanospherical brushes exhibit ideal handling and viscosity allowing for an increase in the polymer-to-monomer ratio in comparison to cements prepared with PMMA nanospheres.

In accordance with the forgoing objects and advantages, a mild and efficient method of grafting PMMA brushes onto cross-linked PMMA nanospheres is provided. In brief, this novel method includes one or more of the following steps: 1. hydrolysis of the surface methyl esters of the PMMA nanoparticles; 2. synthesis of 2-aminoethyl acrylate; 3. coupling of the PMMA nanospheres surface carboxylic acid groups with 2-aminoethyl acrylate, and 4. grafting of PMMA onto the surface carbon-carbon double bonds to give brushes. As discussed in further detail herein and in the Examples below, preliminary results showed that the grafting density achieved with this method is superior in comparison to previous techniques, in addition to the fact that the steps required for the modification of the particles can be applied on a large scale and at room temperature. Preliminary results also showed adequate exothermal and mechanical properties besides optimal viscosity for cements made with brushes.

In accordance with an embodiment of the present invention, and as further explained in the Examples below, grafting of PMMA brushes was performed through a multistage reaction scheme. Briefly, cross-linked PMMA nanoparticles (~300 nm in diameter) were surface modified via a series of reactions for attachment of aminoethyl acrylate groups that served as initiating sites for brush grafting. PMMA brushes were tethered on the surface of the nanospheres via free radical graft copolymerization of methyl methacrylate (MMA) in water using potassium persulfate (KPS) as the initiator. To determine optimal brush molecular weight ($M_w$) for addition in two-solution cements, the reactions were performed at MMA concentrations of 2, 4 and 5 wt % with KPS concentrations varying from 0.4 to 1 wt %. The degree of modification in each reaction step was verified by $^1$H NMR (Bruker DPX-300). $M_w$ of grafted chains was determined by GPC (Waters 2414) with a multi-angle light scattering detector (miniDawn TREOS, Wyatt). The graft density and degree of stretching of brush compositions diluted in tetrahydrofuran was determined with dynamic light scattering (DLS, Wyatt). Selected brush compositions were added to two-solution cements, which were prepared as described previously. Brush-cements prepared at increasing P:M ratios (1:1 to 1.2:1) were subjected to viscometry using a Brookfield Viscometer (DV-E). The concentration of residual monomer was measured with differential scanning calorimeter in isothermal mode (DSC 7, Perkin Elmer). The results were compared with a standard formulation containing linear PMMA (TSBC) and cements prepared with a mixture of PMMA nanospheres and linear PMMA.

In accordance with an embodiment of the present invention, the results of the these methods showed that a higher degree of surface modification was achieved with this method, which allowed for high brush grafting efficiencies, as confirmed by $^1$H NMR. The $M_w$ of the grafts was observed to increase with an increase in the concentration of MMA up to 5 wt %. The composition 2 wt % MMA/0.4 wt % KPS showed appropriate $M_w$ for the preparation of brush cements (110 kg/mol). DLS results revealed that brush densities on the nanospheres core decreased exponentially ($R^2$=0.97) with an increase in the $M_w$ of the grafts, reaching a maximum grafting density at 2 wt % MMA/0.4 wt % KPS (1.02 chains/nm$^2$) and a minimum at 5 wt % MMA/0.4 wt % KPS (0.39 chains/nm$^2$). Brush stretching, determined by the ratio of brush thickness (h) to the radius of gyration ($R_g$) of grafts (h/$R_g$), exhibited a linear decrease with increasing $M_w$ of grafts ($R^2$=0.72). This result points to a possible collapse of the higher $M_w$ grafted chains onto the nanoparticle core due to the lower graft densities observed for these compositions. Cements prepared with brushes synthesized at 2 wt % MMA/0.4 wt % KPS allowed for a significant increase in the P:M ratio (up to 1.2:1) in comparison to the TSBC (0.9:1) and nanospheres cements. Brush cements prepared at P:M ratios of 1:1 and 1.1:1 exhibited significantly lower viscosities than nanospheres cements at the same P:M ratios. Residual monomer in the cement matrix was significantly reduced when PMMA brushes substituted the linear PMMA (2.5 wt % in comparison to 12.5 wt % for TSBC). The decrease in residual monomer achieved with brush addition is a result of the increase in the polymer concentration in the mixture and higher degrees of monomer conversion.

In accordance with an embodiment of the present invention, the novel synthetic pathway (method) described herein showed advantages over other methods employed for efficient modification of PMMA particles and grafting of PMMA brushes at high densities. The graft density was observed to vary with graft $M_w$, being tuned by simple variations in the concentrations of monomer and initiator, which ultimately allowed for cement viscosity reduction through maximum graft attachment and stretching. The addition of brushes synthesized via this method enabled the preparation of solutions at higher P:M ratios, which exhibited lower viscosities than the linear TSBC and nanospheres formulations. The addition of brushes also resulted in a significant decrease in the residual monomer concentration in cured cements.

In accordance with an embodiment of the present invention, novel multi-solution bone cements are provided with reduced monomer concentration, lower viscosities, and the complete substitution of the dissolved PMMA linear polymer portion of the cement mixture with PMMA nanospherical brushes. The cross-linked core of the spherical brush will swell in monomer and the tethered chains will play the role of dissolved linear polymer, thereby imparting viscosity to the cement mixture and providing a mechanically coupled interface at the surface of the beads. Other embodiments of the present invention, as described herein, have shown that the partial substitution of the linear PMMA phase of the cement mixture for cross-linked PMMA nanospheres allowed for a significant increase in the polymer concentration (polymer-to-monomer ratio), providing an effective means for tailoring viscosity without degrading the mechanical integrity of the material. The total substitution of the linear PMMA phase for PMMA nanospherical brushes allows for further increase in the polymer-to-monomer ratio (polymer concentration in the cement mixture) in relation to cements prepared with linear polymer (standard two-solution cement) and nanospheres-containing cements, which is partially mixed with linear polymer. This is expected to reduce the levels of residual monomer in this cement formulation and to enhance the material/mechanical properties through physical entanglements of the grafted PMMA nanospherical brushes with polymerized chains in the cement matrix.

BRIEF DESCRIPTION OF THE DRAWINGS

The present invention will be more fully understood and appreciated by reading the following Detailed Description in conjunction with the accompanying drawings, in which:

FIG. 32 is a table that shows multi-solution bone cement compositions, according to an embodiment of the present invention.

DETAILED DESCRIPTION

Figure 1:
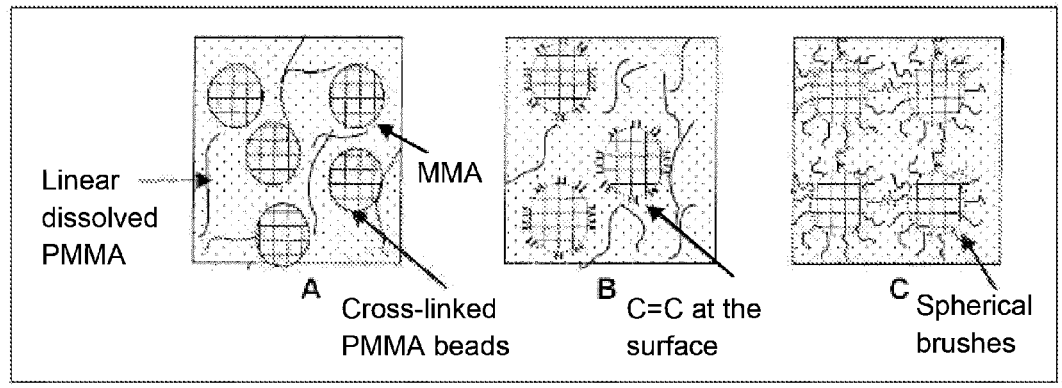
FIG. 1 is a schematic of three bone cement systems according to an embodiment of the present invention.

Referring now to the drawings, wherein like reference numerals refer to like parts throughout, there is seen in FIG. 1 (FIG. 1A-C) three cement systems according to the present invention. Briefly, FIG. 1(A) shows linear polymer and cross-linked beads in monomer, FIG. 1(B) shows linear polymer, and C=C modified cross-linked beads in monomer, and FIG. 1(C) shows polymer brushes in monomer.

An embodiment of the present invention generally comprises multi-solution based bone cements having polymer-to-monomer (P:M) ratios approaching 2:1 and material properties that are comparable to currently available powder-liquid cements.

In accordance with an embodiment of the present invention, the viscosity of the cement solutions of the present invention are a function of the total P:M ratio, the ratio of cross-linked beads to linear polymer, and the cross-link density and size of the beads. The bone cements of an embodiment of the present invention are formed by adding polymer in the form of cross-linked poly(methyl methacrylate) (PMMA) beads to solutions of dissolved linear polymer. Alternatively, the present invention is formed by replacing the linear polymer with spherical PMMA brushes. Cross-linked PMMA particles swell in monomer but do not dissolve, minimizing their contribution to the viscosity of the polymer solutions compared to the dissolved linear polymer.

An embodiment of the present invention involves the enhancement of the interfacial bonding of this particle phase to the polymerized PMMA matrix, and subsequently the mechanical properties of the cement, by creating reactive sites at the surface of the cross-linked beads that could participate in the free radical polymerization reaction during cement curing.

An embodiment of the present invention also encompasses the synthesis of spherical polymer brushes, consisting of cross-linked PMMA beads with linear PMMA molecules covalently tethered to their surfaces. The spherical PMMA are mixed with methyl methacrylate (MMA) monomer to create bone cement formulations which do not required additional dissolved linear PMMA. In the presence of the monomer, the cross-linked bead component of the spherical brushes will swell and the tethered PMMA chains will act like dissolved polymer, although anchored at one end, thereby imparting both viscosity to the mixtures through physical chain entanglements and a mechanically coupled interface at the surface of the beads.

In accordance with an embodiment of the present invention, plain cross-linked PMMA beads can be used in combination with dissolved linear PMMA in methyl methacrylate monomer (MMA) to form the first cement type, as seen in FIG. 1(A).

In accordance with an embodiment of the present invention, the cross-linked PMMA beads can be modified via chemical reaction, in order to create functional reactive sites at the surface of the beads, consisting of carbon-carbon double bonds. These bonds will be able to participate in the free radical polymerization reaction that occurs during bone cement setting, creating a covalent or chemical bond between the cross-linked beads and the polymerized cement matrix. These cross-linked PMMA beads can be used in combination with dissolved linear PMMA in MMA monomer to form the second cement type, as seen in FIG. 1(B). Using functionalized beads in this cement composition improves interfacial bonding between the particle phase and the polymerized PMMA matrix, resulting in cements with enhanced mechanical properties.

In accordance with an embodiment of the present invention, the last cement type is based on the synthesis of spherical polymer brushes, consisting of cross-linked PMMA beads with linear PMMA molecules covalently tethered to their surfaces. Spherical PMMA brushes are then be mixed with methyl methacrylate (MMA) monomer to create the third cement type, as seen in FIG. 1(C). This cement composition does not require additional dissolved linear PMMA. In the presence of the monomer, the cross-linked bead component of the spherical brushes will swell and the tethered PMMA chains will act like dissolved polymer, although anchored at one end, thereby imparting both viscosity to the mixture through physical chain entanglements and a mechanically coupled interface at the surface of the beads.

Advantages of the invention are illustrated by the following Examples. However, the particular materials and amounts thereof recited in these examples, as well as other conditions and details, are to be interpreted to apply broadly in the art and should not be construed to unduly restrict or limit the invention in any way.

EXAMPLES

Example 1

Synthesis of Cross-Linked PMMA Beads

This example relates to the synthesis of cross-linked PMMA beads. In brief, cross-linked PMMA beads have been synthesized via suspension polymerization of methyl methacrylate, using benzoyl peroxide (BPO), 2,2'-azo-bis-isobutyrylnitrile (AIBN), or potassium persulfate (KPS) as the initiator, ethylene glycol dimethacrylate (EGDMA) as the cross-linker (in varying concentrations), and poly(vinyl alcohol) (PVA) as the stabilizer. Resulting beads were subjected to post-synthesis heat treatment at 91° C. for 18 h in order to decompose any residual BPO and yield polymer that is stable in monomer solutions containing DMPT. Bead size can be controlled by varying the suspension medium and the speed of mixing during the synthesis. Beads that have been synthesized to date range in size from less than 1 µm to over 100 µm in diameter, with the majority in the 10-50 µm range. Cross-linker concentrations have been varied between 1% and 30%. The degree to which the beads swell in monomer solutions is inversely proportional to the cross-linker concentration used in the synthesis.

Example 2

Preparation of Multi-Solution Based Bone Cement with Cross-Linked PMMA Beads This example relates to the preparation of multi-solution based bone cement with cross-linked PMMA beads as synthesized in Example 1. First, the desired ratio of cross-linked beads to PMMA powder (linear chains) is determined. These two components are massed and subsequently mixed together in a suitable container. Next, MMA is added to two graduated cylinders. The desired concentrations of BPO initiator or DMPT activator are then dissolved in MMA in separate containers, followed by the addition of 10-30 wt % barium sulfate (if radiopacity is desired, e.g., for vertebroplasty and kyphoplasty applications). The solutions are transferred to polypropylene cartridges. Next, the mixture of PMMA powder and cross-linked PMMA beads is added to the MMA solutions. The cartridges are sealed, vigorously agitated by hand, and placed on a rotating drum mixer for 6 hours. This is a significant reduction in mixing time as compared to current two-solution cement formulations without cross-linked beads (18 hr). Following mixing, the cartridges are removed and stored upright at 4° C. The solutions can be mixed through a static mixing nozzle and polymerize in the same manner as two-solution bone cement without cross-linked beads.

Example 3

Figure 2:
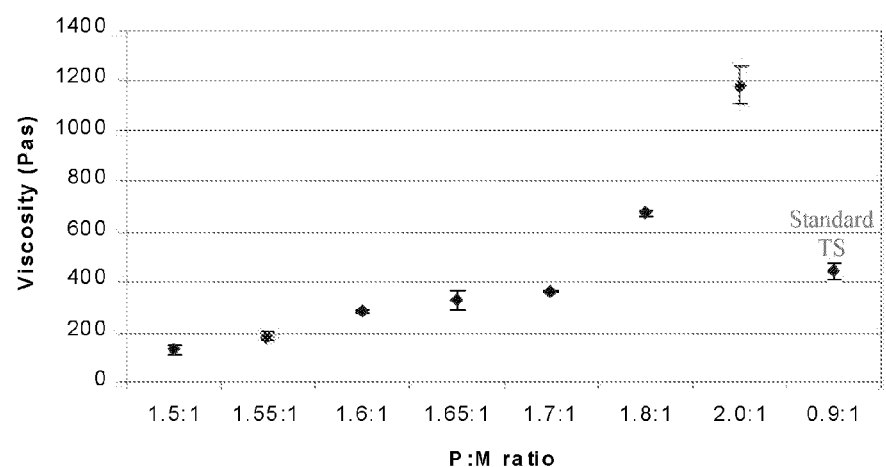
FIG. 2 is a graph of viscosity versus polymer-to-monomer ratios for multi-solution bone cements according to an embodiment of the present invention.

Properties of Multi-Solution Based Bone Cement with Cross-Linked PMMA Beads This example relates to the properties of the multi solution based bone cement with cross-linked PMMA beads as described in Example 2. A number of experiments have been performed to characterize the properties of solutions and potential cement compositions of multi-solution based bone cement with cross-linked PMMA beads. The viscosity of solutions consisting of cross-linked PMMA beads, linear PMMA, and MMA, increase significantly with increasing polymer-to-monomer (P:M) ratio, as seen in FIG. 2. FIG. 2 depicts the viscosity versus polymer-to-monomer ratio for multi-solution based bone cements with cross-linked PMMA beads. Solutions had a constant ratio in the concentration of cross-linked beads to linear PMMA. As expected, viscosity increases significantly with increasing P:M ratio. The addition of cross-linked PMMA beads allows for a nearly double P:M ratio compared to standard two-solution (TS) cements with comparable solution viscosity. The viscosity of Simplex P commercial bone cement has been reported as 800 Pa*s at 3 min after the onset of mixing. This data also demonstrates that the P:M ratio of these cements can be nearly doubled as compared to standard two-solution cements, while maintaining a comparable viscosity.

The polymerization exotherm measured for multi-solution bone cement with cross-linked PMMA beads was significantly lower than that of standard two-solution cement with the same initiation chemistry and comparable to the commercially available Palacos R-40 bone cement. There were no significant differences in setting times across the three compositions. These data are for a single cement composition with a P:M ratio of 1.4:1. The polymerization exotherm in setting bone cement is inversely proportional to the P:M ratio, therefore, it is reasonable to expect that a further reduction in exotherm could be achieved by increasing the P:M ratio to the range of 1.7:1, which is certainly feasible from a viscosity standpoint, see FIG. 2.

Table 1 below provides the exotherm and setting time for multi-solution based cement with cross-linked beads, standard two-solution cement, and Palacos R-40 commercial cement. Values are given as the average±one standard deviation and significant differences (p<0.05) are denoted by asterisks.

TABLE 1

| | Palacos R-40 | Two-solution | multi-solution w/beads | |
|---|---|---|---|---|
| P:M   $P_b:P_l$ | 1.71:1 | 0.9:1 | 1.4:1 | 1.8:1 |
| $T_{max}$ (° C.) | 81.18 ± 5.99 | 95.012 ± 5.75* | 75.97 ± 0.94 | |
| $t_{set}$ (min) | 8.48 ± 0.31 | 8.73 ± 0.52 | 9.175 ± 0.12 | |

Figure 3:
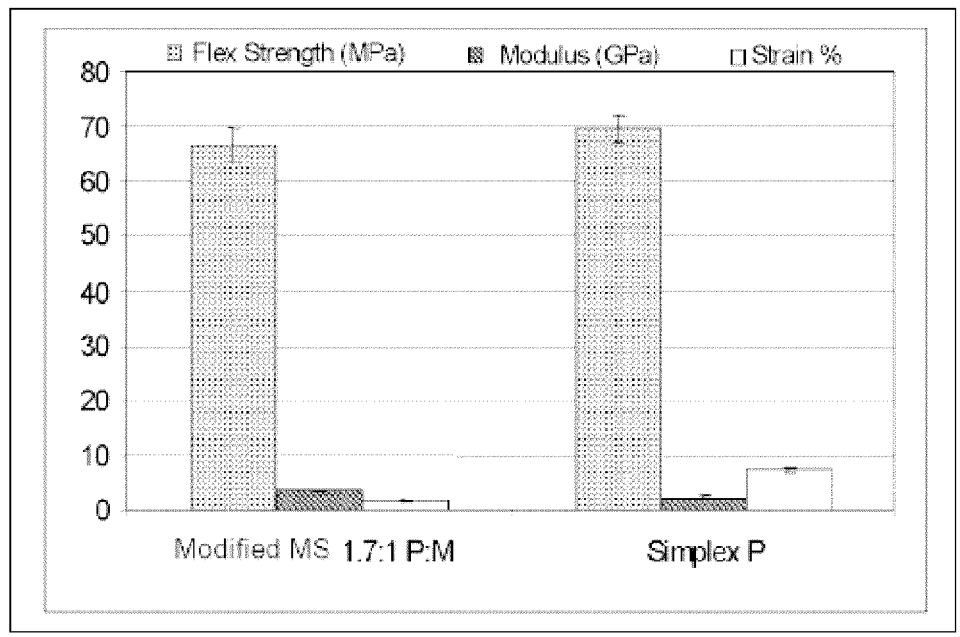
FIG. 3 is a graph of flexural testing data for multi-solution bone cements according to an embodiment of the present invention.

As seen in FIG. 3, in a preliminary investigation of the flexural mechanical properties of multi-solution based bone cements with cross-linked PMMA beads, this type of cement displays comparable flexural strength to Simplex P bone cement. FIG. 3 provides flexural testing data showing flexural strength, modulus, and strain-to-failure for one composition of multi-solution based bone cement with cross-linked PMMA beads at a P:M ratio of 1.7:1 and Simplex P bone cement. There is a significant reduction in the strain-to-failure for the multi-solution based cement.

Figure 4:
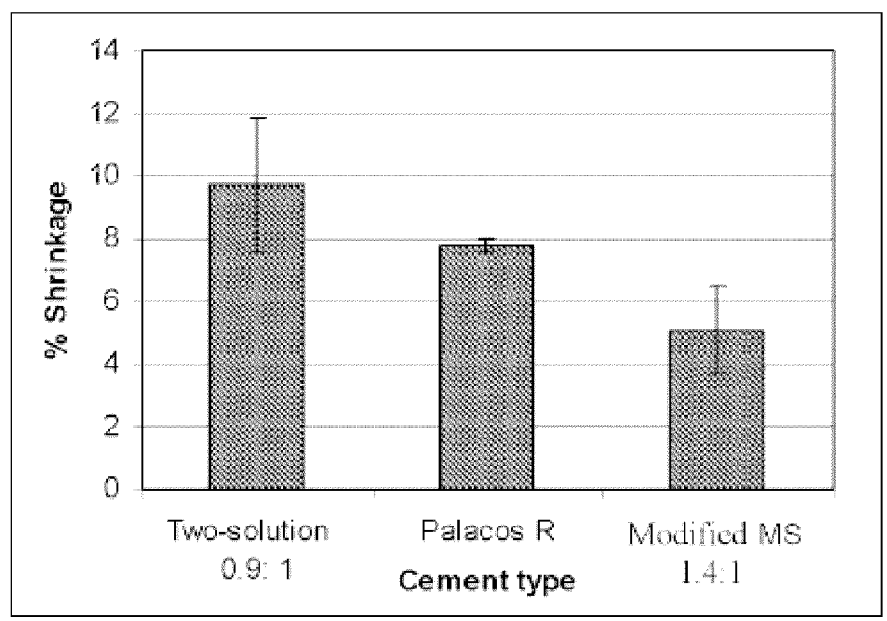
FIG. 4 is graph of volumetric shrinkage verses bone cement composition according to an embodiment of the present invention.

Referring to FIG. 4, tests measuring the volumetric shrinkage of bone cement during the polymerization process show that multi-solution based bone cement with cross-linked PMMA beads at a P:M ratio of 1.4:1 had significantly reduced shrinkage versus standard two-solution cement and Palacos R-40 bone cement. FIG. 4 depicts volumetric shrinkage versus cement composition. Increasing the P:M ratio of multi-solution bone cement via the addition of cross-linked PMMA beads reduced the volumetric shrinkage of the cement, which is due to the conversion of monomer to polymer. This data demonstrates another cement property for which an increase in the P:M ratio is beneficial.

Example 4

Surface Modification of PMMA Cross-Linked Beads

This example relates to the surface modification of PMMA cross-linked beads as synthesized in Example 1. The bead-matrix interface can be mechanically strengthened by promoting covalent bonding between the two phases. Therefore, cross-linked PMMA beads have been modified to create unsaturated carbon double bonds at their surface. These double bonds can participate in the free radical polymerization reaction during matrix formation, potentially creating a chemical bond at the bead-matrix interface.

Step One: Surface Modification of PMMA Beads with Ethanolamine

Figure 5:
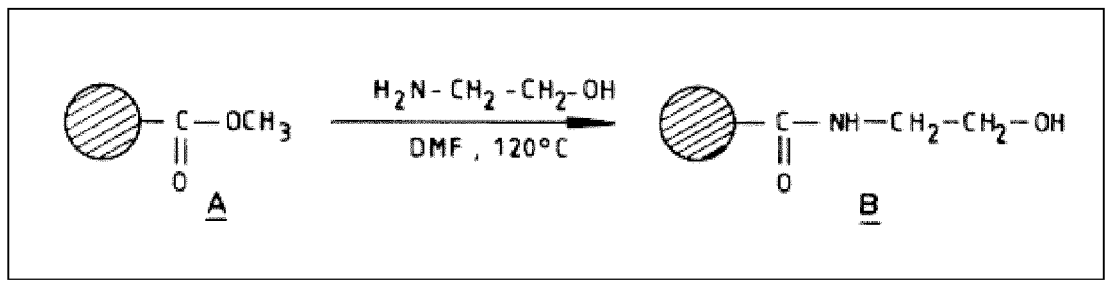
FIG. 5 is a reaction schematic of PMMA with ethanolamine in DMF according to an embodiment of the present invention.
Figure 6:
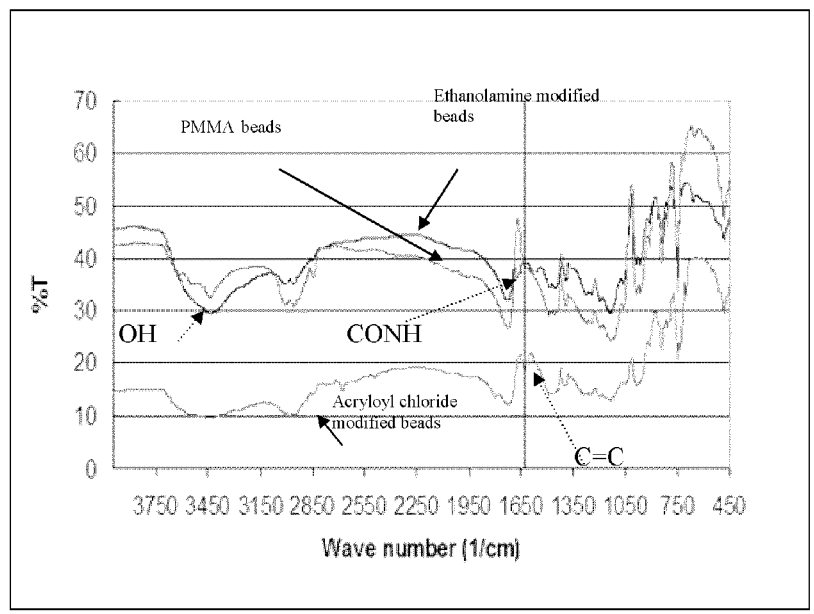
FIG. 6 is a graph of FTIR profiles in transmission mode of the modification reactions according to an embodiment of the present invention.

The first step in the formation of modified PMMA beads according to the invention is to modify the surface of PMMA beads by adding a hydroxyl group. This reaction replaces the ester group with a hydroxyl group, as shown in FIG. 5. The reaction was performed at 120° C. in N,N dimethylformamide (DMF). Twenty grams of cross-linked PMMA beads were swollen for 12 hours in DMF. Then the beads were subjected to a reaction with 25 g of ethanolamine at 120° C. for 9 hours. The reaction was then cooled to ambient temperature. The beads were washed with water, followed by methanol. Finally, the beads were subjected to soxholet extraction with methanol for 48 hours to extract any ethanolamine residue. FTIR analysis of the beads was performed by incorporating the modified beads in a potassium bromide (KBr) pellet. FIG. 6 contains three lines starting from the left (related to each other relative to the vertical axis) including a "top," "middle," and "bottom" line or spectrum. FIG. 6 illustrates the FTIR spectra of cross-linked PMMA beads (middle spectrum) and ethanolamine surface modified PMMA beads (top spectrum). FIG. 6 details the FTIR profiles in transmission mode of the two step modification reactions. The middle line shows the spectrum of the unmodified cross-linked PMMA beads. The top line shows the spectrum of ethanolamine modifies beads. The bottom line shows the spectrum of acryloyl modified beads. Note the carbon-carbon double bond peak at $\approx 1640$ $cm^{-1}$. The hydroxyl group is very clear at 3450 $cm^{-1}$ and amide group at 1680 $cm^{-1}$. These two peaks increase in intensity with increasing reaction time or decreasing cross-linker concentration.

Step Two: Surface Modification with Acryloyl Chloride

Figure 7:
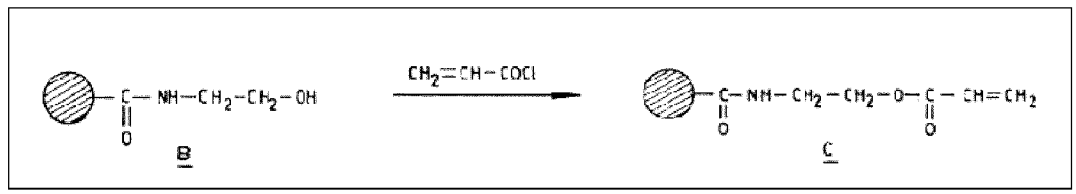
FIG. 7 is a reaction schematic of modified PMMA beads with acryloyl chloride in dichloromethane according to an embodiment of the present invention.

The second step in the formation of modified PMMA beads according to the invention is to subject the ethanolamine modified cross-linked PMMA beads to acryloyl chloride in dry dichloromethane in the presence of triethylamine, as seen in FIG. 7. Five grams of cross-linked PMMA beads were swollen in 25 g of dry dichloromethane and cooled on ice under stirring. The reaction was permitted to go for 6 hours at 0° C. and then for another 6 hours at room temperature. The product was then washed with 0.1 N HCl followed by saturated sodium hydrogen carbonate solution, followed by water, and finally methanol. The product was dried in a vacuum at room temperature. FIG. 6 shows the FTIR spectrum of acryloyl chloride modified beads (bottom line) in KBR pallets. Note the drop in the hydroxyl peak at 3450 $cm^{-1}$ and the formation of the carbon-carbon double bond peak at 1640 $cm^{-1}$.

Example 5

Preparation of Multi-Solution Bone Cement with Surface Modified PMMA Beads

This Example relates to the preparation of multi-solution bone cement with the surface modified PMMA as synthesized in Example 4. The formation of modified PMMA beads according to the invention also requires determining the desired ratio of surface modified, cross-linked beads to PMMA powder (linear chains). These two components are massed and subsequently mixed together in a suitable container. Next, MMA is added to two graduated cylinders. The desired concentration of BPO initiator or DMPT activator is then dissolved in the MMA, followed by the addition of 10-30 wt % barium sulfate (if radiopacity is desired). The solutions are transferred to 200 ml polypropylene cartridges. Next, the mixture of PMMA powder and surface modified, cross-linked PMMA beads is added to the MMA solutions. The cartridges are sealed, vigorously agitated by hand, and placed on a rotating drum mixer for 6 hours. Following mixing, the cartridges are removed and stored upright at 4° C. The solutions can be mixed through a static mixing nozzle and polymerize in the same manner as multi-solution bone cement without cross-linked beads.

Example 6

Synthesis of PMMA-PMMA Spherical Polymer Brushes

Figure 8:
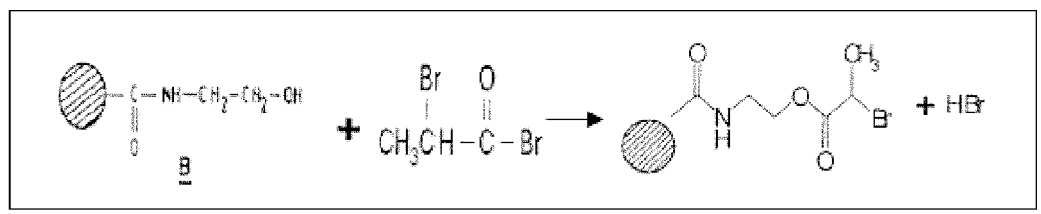
FIG. 8 is a reaction schematic of a modification reaction according to an embodiment of the present invention.

This Example relates to the synthesis of PMMA-PMMA spherical polymer brushes. The synthesis of the polymer brushes of the present invention is performed by surface modification of PMMA beads with ethanolamine as previously described in Example 4, followed by modification with 2-bromoisobutyryl bromide and finally an atom transfer radical polymerization (ATRP) reaction with MMA. Surface modification with 2-bromoisobutyryl bromide was performed on ethanolamine modified PMMA beads in THF at 0° C. in the presence of triethylamine for 12 hrs. This reaction was continued for 24 hours at room temperature followed by filtrations, cleaning and finally drying in a vacuum at room temperature. FIG. 8 is a schematic of the reaction between ethanolamine modified PMMA beads and 2-bromoisobutyryl bromide.

Figure 9:
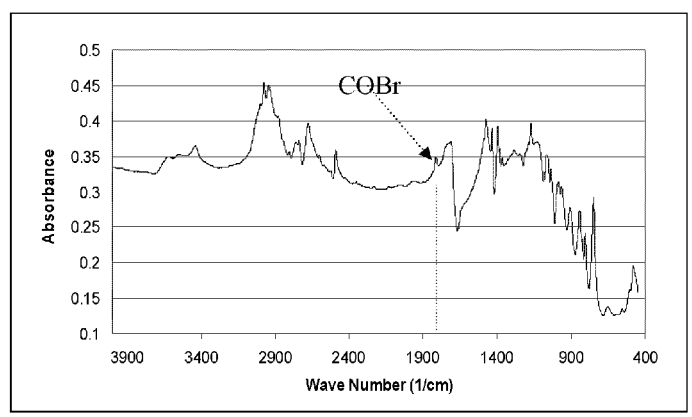
FIG. 9 is a graph of the FTIR profile of 2-bromopropionyl bromide modified PMMA beads according to an embodiment of the present invention.

FTIR analysis in a KBr disk was performed on the modified beads to confirm the surface modification. FIG. 9 shows the FTIR profile of 2-bromoisobutyryl bromide modified cross-linked PMMA beads, where the peak at 1813 $cm^{-1}$ is the COBr peak. Note the drop in the hydroxyl peak and the appearance of COBr at 1813 $cm^{-1}$ and 1168 $cm^{-1}$.

Atom Transfer Radical Polymerization (ATRP)

Atom transfer radical polymerization (ATRP) reaction was carried out in a Schlenk flask at room temperature for 24 hours in the presence of surface brominated PMMA beads, Cu(I) Br, Cu(II) Br, hydroquinone free MMA, and hexamethyl triethylene triamine. The product of the reaction was cleaned thoroughly, then weighed and imaged. Before the ATRP reaction, PMMA modified beads were 100 micron or less in diameter. Bead diameter increased after the reaction to as much as 200 microns. In addition, the weight of the beads was measured before and after the reaction. The weight increased by 200%.

Alternate Synthesis Route

Cross-linked PMMA nanospheres were synthesized as described in Example 10, infra, and were modified with ethanolamine and acryoyl chloride as previously described in Example 4, resulting in $CH_2=CH_2$ end groups on the surface of the PMMA beads that serve as initiation sites for graft polymerization of the PMMA brushes. Brush synthesis was carried out in a three-neck flask under a nitrogen atmosphere at 70° C. Potassium persulfate (KPS) was used as the initiator for free radical polymerization of MMA using water as the medium for suspension polymerization. Briefly, 1 g of acryloyl chloride modified nanospheres were dispersed in 80 mL of deionized water under vigorous stirring and the temperature was raised to 70° C. KPS was then added to the flask at a concentration ranging from 0.10-1.0 wt % and the mixture was stirred for 30 min. MMA monomer (5 to 15 wt %) was added dropwise to the medium and the reaction was carried out for 8 hrs. The product was collected and subjected to sohxlet extraction for 24 hr.

Example 7

Preparation of Bone Cement with PMMA-PMMA Spherical Brushes

This Example relates to the preparation of bone cement with PMMA-PMMA spherical brushes as synthesized in Example 6. The preparation of the third type of cement according to the present invention differs from the procedures for the first two types in that the polymer brushes will be the only solid polymer component added to the MMA, initiation chemicals, and radiopacifier in order to form the cement solutions (i.e., no linear polymer is dissolved).

One or more of the multi-solution bone cements according to the present invention have the capacity to meet the clinical need of improved cements for fixation of total joint replacements, along with other applications including vertebroplasty (VP) and kyphoplasty (KP) which are minimally invasive procedures used to treat vertebral compressive fractures. The change in form of cement, from powder-liquid to multi-solution based, significantly simplifies the mixing and delivery procedure in the operating room and produces a cement of more consistent quality, by eliminating variability in these processes. The multi-solution bone cements according to the present invention also have well controlled viscosities which remain relatively constant during the mixing and delivery process, as opposed to the viscosity of current commercial cements which is highly dynamic and increases significantly from the point of mixing to implantation of the cement. This property is particularly desirable for VP and KP applications.

Example 8

This example describes the effect of overall polymer-to-monomer ratio (P:M) and polymer bead (Pb) to linear polymer (Pl) ratio on the viscosity of modified multi solution bone cements.

Cross-linked polymer beads were synthesized. These beads consisted of 12% crosslinker with a nominal bead size of about 20 to 50 µm. These were made using suspension polymerization methods. Then, multi-solution bone cements were made with MMA monomer, 80,000 g/mol molecular weight linear PMMA polymer and the cross-linked PMMA beads. Various ratios of bead to linear polymer and total polymer to monomer were fabricated and their viscosity was determined using rheometric methods at room temperature. The ranges were: P:M ratio of 1.3:1 to 1.4:1, and Pb:Pl ratio of 1:1 to 2.5:1.

Figure 10:
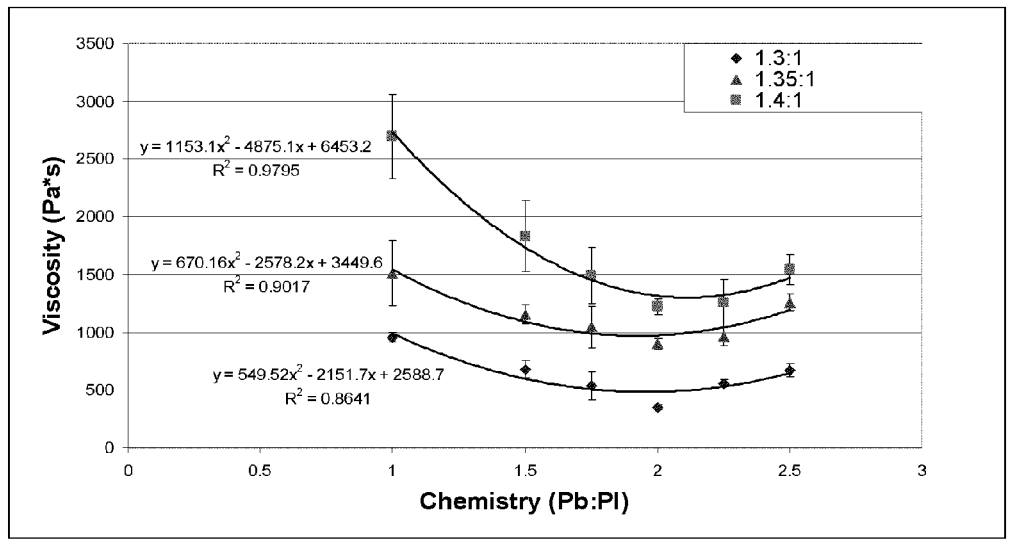
FIG. 10 is a graph of a summary of viscosity versus Pb:Pl ratio for three different P:M ratio multi-solution bone cements according to an embodiment of the present invention.

The results of viscosity testing are summarized in FIG. 10, which shows a summary of viscosity versus Pb:Pl ratio for three different P:M ratio multi solution bone cements.
Note that the viscosity decreases with decreasing P:M ratio, and that increasing Pb:Pl ratio first decreases viscosity (below 2:1) and then slightly increases (above 2:1) viscosity.

It can be seen that the viscosity of the cement varies both with bead-to-linear-polymer ratio as well as polymer to monomer ratio. There is an increase in viscosity with increasing P:M ratio at every fixed Pb:Pl ratio. There is also a very interesting change in viscosity with ratio of bead polymer to linear polymer. There is a decrease, then slight increase in viscosity is the quantity of bead polymer is increased relative to linear polymer with a distinct minimum occurring at about 2:1 for all three P:M ratio cases. This indicates that the viscosity will decrease as the amount of bead polymer increases up to the 2:1 ratio. Above this ratio, increasing the Pb:Pl ratio slightly raises the viscosity and eventually the viscosity levels out (data not shown). These changes appear to reflect complex viscosity behavior where at less than the 2:1 ratio, the beads interfere with the mechanism of viscosity formation (primarily linear polymer chain sliding) and reduce the overall viscosity, whereas above 2:1, the viscosity increases as the bead-bead interactions begin to create increased viscosity.

This example shows that viscosity of multi-solution bone cement can be modified by the presence of cross-linked polymer beads, and that a minimum viscosity condition is developed at a ratio of Pb:Pl of around 2:1.

Example 9

This Example shows the mechanical properties of modified multi solution bone cement made from cross-linked polymer beads, linear polymer and monomer after the cements have been polymerized as they would be in-vivo.

Modified multi solution bone cements consisting of linear 80,000 g/mol polymer, cross-linked polymer PMMA beads (with 12% EGDMA cross linker), MMA monomer and BPO and DMPT were used to make polymerized solid cement samples for mechanical testing. The Multi-solution mixtures were dispensed through a static mixing nozzle into rectangular Teflon molds approximately 3 mm×10 mm×40 mm. These samples were then used in three point bending flexural testing to determine the flexural strength (i.e., the stress to cause failure in 3-point bending), flexural modulus (E) and flexural strain to failure. The samples, once fabricated were measured and then tested on a mechanical test frame until failure. The stress, strain and modulus were determined using the standard equations for 3-point bending.

Figure 11A:
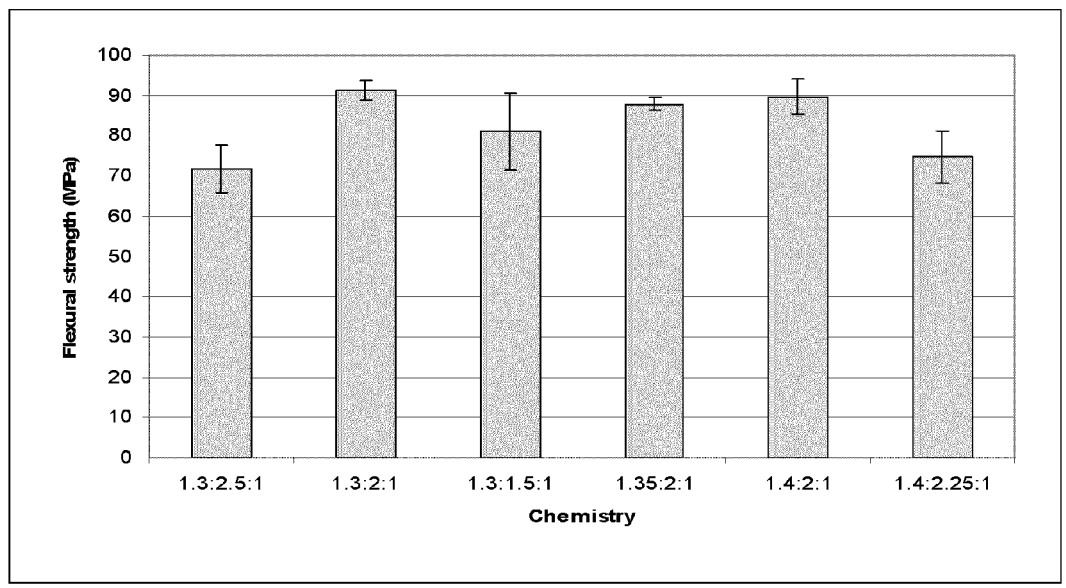
FIG. 11 *a-c* shows the stress to failure, the strain to failure and the modulus of modified multi-solution bone cements according to an embodiment of the present invention.
Figure 11B:
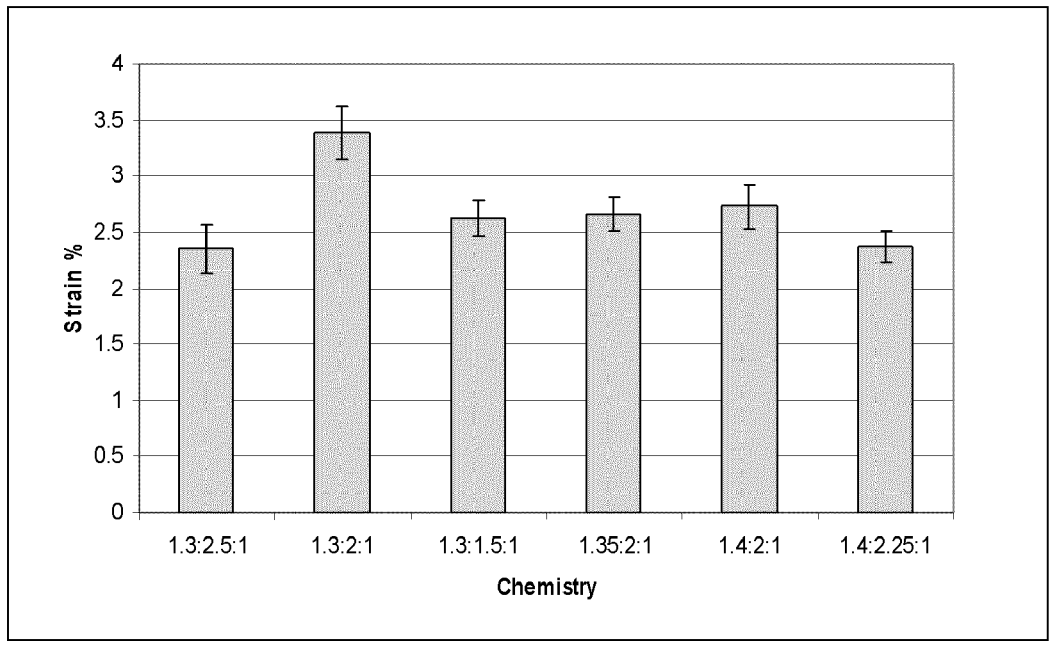
Figure 11C:
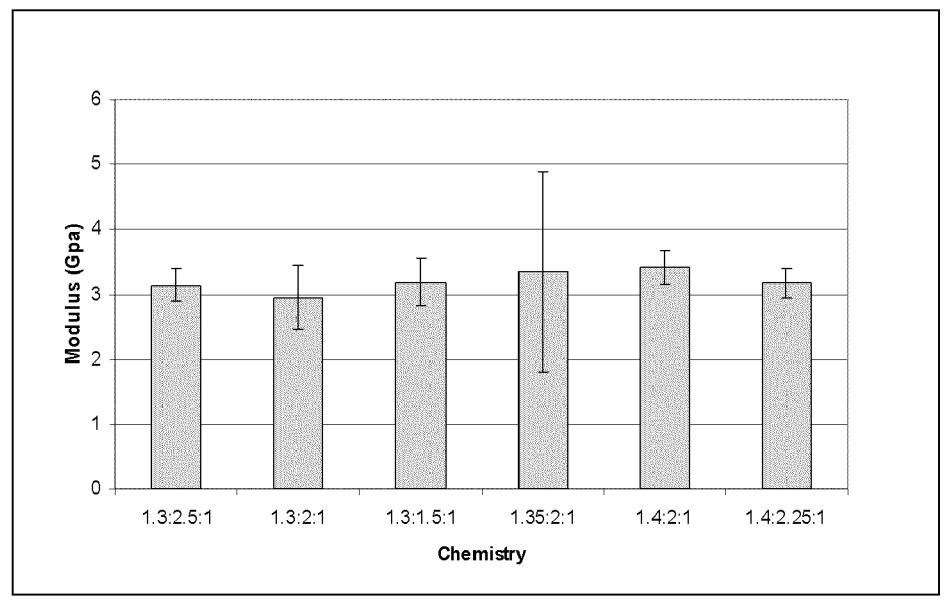

The results are shown in FIG. 11 (11A-11C). Shown are the stress to failure, the strain to failure and the modulus. The x-axis nomenclature is such that the first number is the P:M ratio and the second set of numbers are the Pb:Pl ratio. For example, 1.3:2.5:1 means P:M ratio of 1.3:1 and Pb:Pl of 2.5:1. The results show that for a variety of combinations, the strength of the resulting polymerized cements ranges from 70 MPa to 90 MPa, the strain to failure ranges from 2.3 to 3.3 and the modulus is in the range of 3 GPa. All of these values are in the range of current commercial powder-liquid cements.

In an attempt to tailor viscosity and extend the application of this multi-solution bone cements, it has been shown herein that the viscosity of multi-solution cements can be manipulated by changes in the polymer-to-monomer ratio (denoted by P:M g PMMA/100 mL MMA) and by the addition of cross-linked particles (denoted by Pb) to the linear polymer (denoted by Pl) to make up the total polymer phase (e.g., the mixing of cross-linked microspheres or nanospheres (Pb) with the linear PMMA powder (Pl) at fixed ratios). Increasing the P:M ratio up to 1.4:1 significantly increased the viscosity of two-solution cements prepared with cross-linked PMMA microspheres, however increasing the Pb:Pl ratio at a fixed polymer-to-monomer composition had the effect of decreasing viscosity (up to a 2:1 ratio). These experiments confirmed the viability of tailoring viscosity without compromising the mechanical performance of two-solution cements for extended applications. Accordingly, the following Examples relate to the viscosity characteristics and curing parameters of novel multi-solution cements containing cross-linked PMMA microspheres (e.g., 20-100 μm) and nanospheres (e.g., 300-330 nm) added to the linear polymer phase, and are discussed for cements prepared at different compositions. The effect of PMMA particle size on these properties as well as the range of compositions suitable for applications in the treatment of vertebral compression fractures are also discussed.

Example 10

Exothermal Characteristics of Cements Containing Cross-Linked PMMA Particles

This Example describes the effect of the addition of cross-linked microspheres and nanospheres on the exothermal behavior of two-solution cements, which was evaluated (at a fixed BPO:DMPT ratio of 1) and compared to the standard formulation of two-solution bone cements. The setting characteristics of standard two-solution bone cements have been previously characterized by Hasenwinkel and coworkers at specific BPO:DMPT molar ratios (see Hasenwinkel et al, *A novel high-viscosity, two-solution acrylic bone cement: effect of chemical composition on properties*, J. Biomed Mater Res 1999; 47:36-45; and Hasenwinkel et al, *Effect of initiation chemistry on the fracture toughness, fatigue strength, and residual monomer content of a novel high-viscosity, two-solution acrylic bone cement*, J Biomedical Materials Research 2002; 59, 411-421).

An additional variable in the modified two-solution cements of an embodiment of the present invention is the presence of two polymer phases: 1) dissolved linear PMMA ($P_L$) and 2) dispersed cross-linked PMMA microspheres or nanospheres ($P_b$). The linear PMMA (80,000 g/mol) was used as received (Dajac Laboratories, Feasterville Pa., USA) and the cross-linked beads were synthesized in house via two different polymerization techniques.

Briefly, PMMA microspheres were synthesized via suspension polymerization of methyl methacrylate (MMA), 7.5% v/v (Fluka) using water as the suspension medium, azobisisobutyro-nitrile (AIBN), 0.1% w/v (Sigma-Aldrich) as the initiator, polyvinyl alcohol (PVA), 2% w/v (Sigma-Aldrich) as the stabilizer and ethylene glycol dimethacrylate (EGDMA), 25% v/v (Aldrich) as the cross-linker agent. Microspheres were relatively polydisperse with diameter in the range 20-100 μm. PMMA nanospheres were synthesized via boiling temperature soap-free emulsion polymerization of MMA (6.25% v/v), using water as the dispersion medium, potassium persulfate (KPS), 0.1% w/v (Sigma-Aldrich) as the initiator and EGDMA (25% v/v) as the cross-linker. Resulting nanospheres were subjected to post-synthesis centrifugation for separation of supernantant and cleaning, followed by lyophilization for drying. This technique allows for the synthesis of monodisperse nanospheres ranging in size from 300 to 330 nm. For the preparation of two-solution cements, benzoyl peroxide (BPO) (Aldrich), N,N-dimethyl p-toluidine (DMPT) (Aldrich) and MMA (Fluka) (Aldrich) were used as received without further purification.

The preparation of the standard two-solution cement composed of linear PMMA followed the technique described by Hasenwinkel and coworkers, supra. Cartridges of standard two-solution formulation were prepared at a P:M ratio of 0.9:1.

For the other modified two-solution cements, first the desired ratio of cross-linked nanospheres or microspheres ($P_b$) to linear PMMA ($P_l$) was determined. These two components were massed and mixed together forming the powder phase (P) of the subsequent mixture. Next, part of the total MMA volume was split and added to two graduated cylinders, in which one was mixed with 1.25 g of BPO (1.25 g/100 mL MMA) and the other with 0.7 mL DMPT (0.7 mL/100 mL). The two mixtures BPO/MMA and DMPT/MMA were transferred to two polypropylene cartridges followed by the addition of the powder phase. The remaining MMA volume added to the polypropylene cartridges. The polypropylene cartridges were sealed, vigorously agitated by hand and placed in a rotating drum mixer for 18 hours. Following mixing, the cartridges were stored upright at 4° C. The use of a radiopacifier was avoided in this Example in order to enhance the effect of the presence of a cross-linked phase and particle size on the behavior of novel two-solution cements. Additional Examples, set forth infra, will discuss the effects of elevated concentrations of a radiopacifier on the properties of the standard and modified two-solution bone cements.

The maximum polymerization temperatures and setting times of modified two-solution cements were measured, according to ASTM standard F451, and compared to the setting characteristics of standard two-solution cements. A smaller, custom-designed PTFE mold comprising a total volume of 3 mL was also used to record maximum polymerization temperatures and setting times of the cement compositions with the goal of replicating the approximate volume of cement delivered into a vertebral body during vertebroplasty. The maximum exotherm is defined as the peak in the temperature versus time curve during polymerization, while setting time is given by the time corresponding to the average temperature between ambient and maximum temperatures. Maximum temperatures and setting times are reported as the average of three measurements of each composition in both molds. Differences in maximum exotherm and setting times of compositions prepared with nanospheres and microspheres in comparison to the standard formulation were statistically analyzed using a Dunnett Test for multiple comparisons of all the cements with the control (STSBC) at a level of confidence of 95%. In order to evaluate the effect of particle size and polymer concentration in the groups of modified cements, linear contrasts between nanospheres and microspheres cements were performed. The setting parameters of cements were measured for the compositions described in Table 2, as follows:

TABLE 2

Cement compositions subjected to exothermal testing in the standard and custom designed molds.

| Cement formulation | P:M ratios | $P_b$:$P_l$ ratios |
|---|---|---|
| STSBC | Fixed 0.9:1 | — |
| Microspheres | 1:1, 1.1:1 | 1:1, 1.5:1, 2:1 |
| Nanospheres | 1:1, 1.1:1 | 1:1, 1.5:1, 2:1 |

These compositions were particularly selected based on suitable handling and flow rate of cements injected through a 12 G and 15 cm needle attached to a mixing nozzle. Cements containing a large fraction of cross-linked particles ($P_b$:$P_l$>2:1) exhibited gritty appearance, which made injection more difficult due to clogging of material in the delivery needle.

Figure 12:
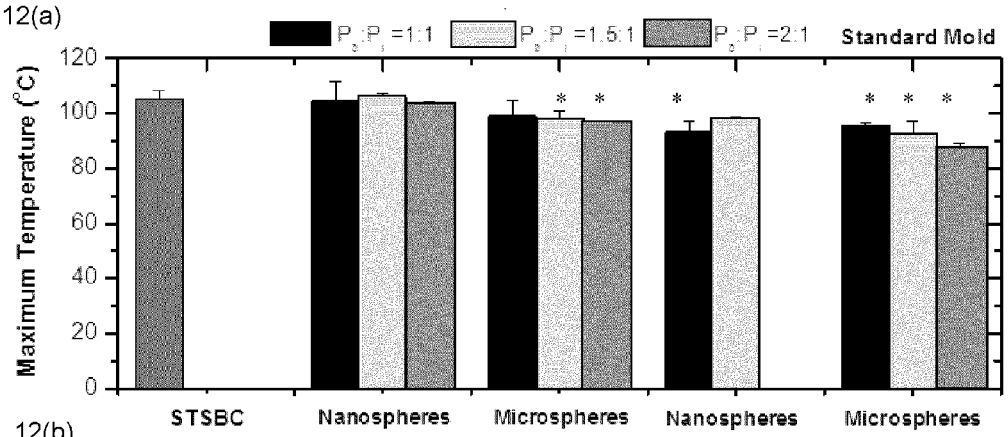
FIGS. 12*a-b* show the maximum polymerization temperatures and setting times, respectively, for cements containing cross-linked nanospheres and microspheres compared to STSBC, according to an embodiment of the present invention.
Figure 12:
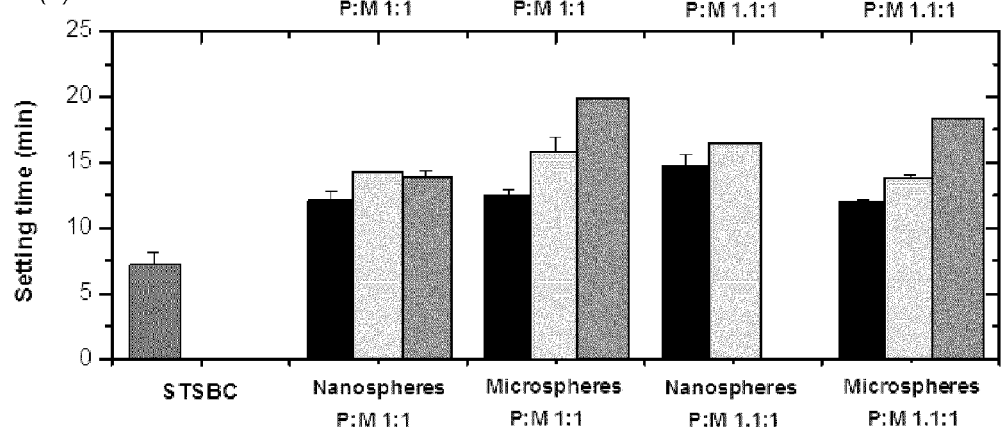
Figure 13:
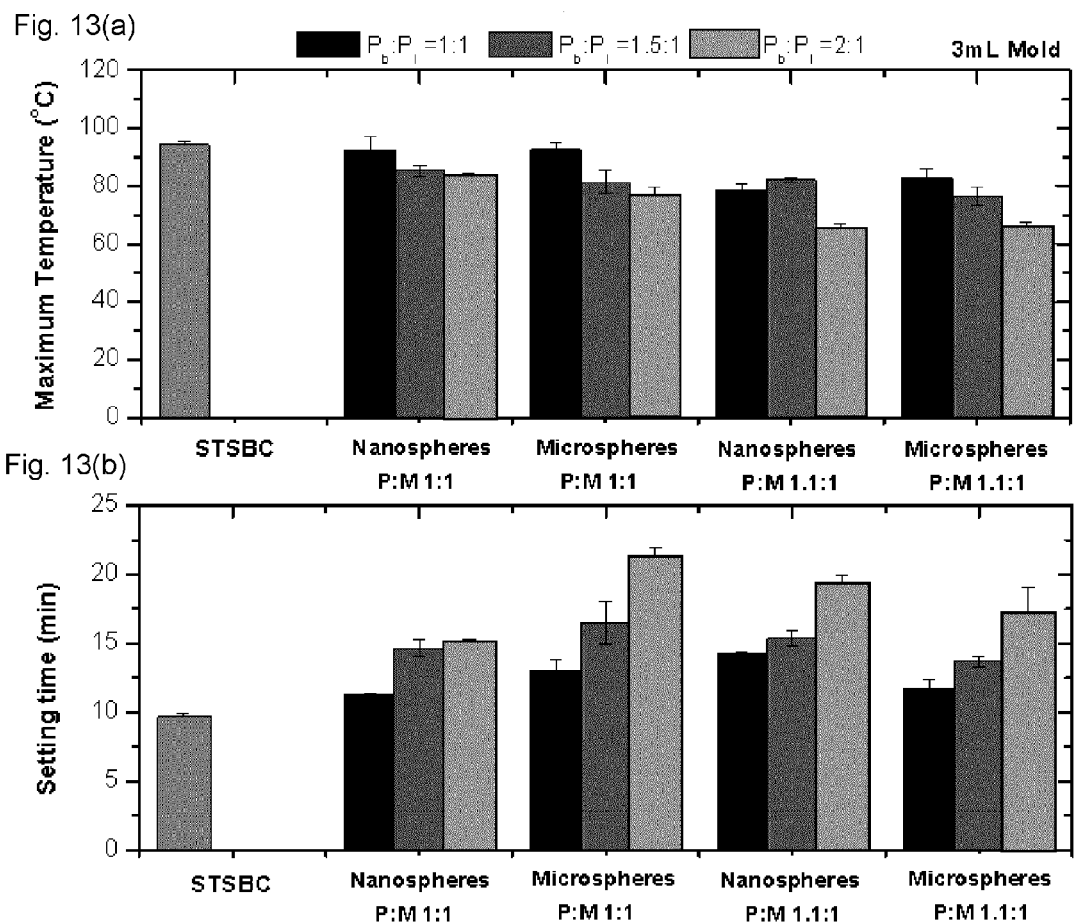
FIGS. 13*a-b* show the maximum polymerization temperatures and setting times, respectively, for cements containing cross-linked nanospheres and microspheres compared to STSBC, according to an embodiment of the present invention.

FIGS. 12-13 illustrate the exothermal characteristics of cements prepared with nanospheres and microspheres at P:M ratios of 1:1 and 1.1:1 as compared to STSBC (P:M ratio of 0.9:1) for experiments performed in the standard ASTM mold and a custom-designed mold with a 3 ml volume and XX mm thick, respectively.

FIGS. 12a and 12b show the maximum polymerization temperatures and setting times, respectively, for cements containing cross-linked nanospheres and microspheres compared to STSBC. Cements were prepared at increasing P:M and $P_b:P_l$ ratios. Results were obtained using a standard ASTM mold. The maximum polymerization temperature decreased and the setting time increased in comparison to the standard formulation across the cements compositions. The symbols (*) in the first panel (FIG. 12a) indicate the compositions which showed a significant difference compared to the control STSBC ($p<0.05$). In the second panel (FIG. 12b), all the composition showed a significant difference in comparison to the control STSBC ($p<0.05$).

In particular, FIG. 12a shows maximum polymerization temperatures of the different compositions being compared with the standard formulation (STSBC). The results show a significant ($p<0.05$) decrease in maximum exotherm for some of the compositions as indicated in the Figure. These compositions showed a decrease in maximum exotherm ranging from 8 to 18° C. compared to the STSBC. Additionally, there is a significant increase ($p<0.05$) in the setting time of cements (FIG. 12b) prepared with cross-linked microspheres and nanospheres for all of the compositions in comparison to the setting time of the standard formulation (approximately 7 minutes). Setting time increased at least 5.9 minutes (nanospheres-containing cements at a P:M of 1:1 with a $P_b:P_l$ of 1:1) and at most 12 minutes (microspheres-containing cement at a P:M of 1:1 with a $P_b:P_l$ of 2:1) with the addition of cross-linked particles.

FIGS. 13a and 13b show the maximum polymerization temperatures (FIG. 13a) and setting times (FIG. 13b) for cements containing cross-linked nanospheres and microspheres compared to STSBC. Cements were prepared at increasing P:M and $P_b:P_l$ ratios. Results were obtained using a custom-designed exothermal mold with a total volume of 3 mL. The results show that the maximum polymerization temperature decreased and the setting time increased in comparison to the standard formulation across the cements compositions. A significant decrease ($p<0.05$) in maximum temperatures for all the compositions in comparison to STSBC is shown, except nanospheres and microspheres-containing cements at a P:M of 1:1 with a $P_b:P_l$ of 1.5:1. The setting time of cements prepared with cross-linked particles increased significantly ($p<0.05$) in comparison to STSBC, except for nanospheres cement at a P:M of 1:1 with a $P_b:P_l$ of 1:1 and microspheres cement at a P:M of 1.1:1 with a $P_b:P_l$ of 1:1.

In particular, the exothermal parameters measured with the smaller mold in FIG. 13a showed a significant decrease ($p<0.05$) in maximum temperatures for all the compositions in comparison to the STSBC formulation, except in two cases (nanospheres and microspheres-containing cements at a P:M of 1:1 with a $P_b:P_l$ of 1.5:1). The reduction in maximum temperature with the addition of cross-linked particles ranged from 8.5 to 29° C. across compositions, in which nanospheres and microspheres containing cements prepared at a P:M of 1.1:1 with a $P_b:P_l$ of 2:1, presented the highest reduction in maximum polymerization temperature (27.6 and 29° C., respectively). Similar to the results illustrated in FIG. 12b, the setting time of cements prepared with cross-linked particles increased significantly ($p<0.05$) in comparison to the standard two-solution formulation (except for nanospheres cement at a P:M of 1:1 with a $P_b:P_l$ of 1:1 and microspheres cement at a P:M of 1.1:1 with a $P_b:P_l$ of 1:1, see FIG. 13b). The increase in setting time ranged from 3.5 minutes (microspheres-containing cements at a P:M of 1:1 with a $P_b:P_l$ of 1:1) to 11.5 minutes (microspheres-containing cements at a P:M of 1:1 with a $P_b:P_l$ 2:1) in comparison to the setting time measured for the standard formulation (approximately 9 minutes). Lower maximum polymerization temperatures were expected to be measured with the custom-designed mold due to the considerably smaller volume of material interacting with the thermocouple.

For all of the compositions tested, including those containing nanospheres and microspheres in the two molds, the results showed that when the content of cross-linked beads increased ($P_b:P_l$ ratio), the setting time became longer. The smaller volume of material polymerized in the 3 mL mold, in order to replicate the approximate amount delivered during surgery, exhibited lower exothermal temperatures but approximately the same setting time. The reduction in maximum temperature measured for cements containing a cross-linked phase may be associated with the dissipation of energy by the PMMA particles dispersed in the matrix. Nanospheres and microspheres may have had the role of an insulator, thereby absorbing and dissipating the excess of heat generated during curing of the cement.

Particle size does not have a strong effect on maximum temperature of two-solution cements containing cross-linked PMMA beads, showing significant differences between microspheres and nanospheres only when the groups are contrasted at a P:M of 1:1 ($p<0.05$) in both molds. When the contrast is performed at a P:M of 1.1:1 there is no significant difference between the groups of cements prepared with nanospheres and microspheres in both molds. On the contrary, there is a significant effect of particle size on the setting time of cements prepared with nanospheres and microspheres, in which the results showed significant differences when contrasted at both P:M ratios and in both molds. Microspheres-containing cements exhibited longer setting times at P:M of 1:1, while at P:M of 1.1:1 nanospheres cements had longer setting times.

Increasing the P:M ratio decreased the maximum exotherm of cements containing microspheres and nanospheres in the two different molds used in this study. Contrast analysis between nanospheres (or microspheres) cements prepared at P:M ratios of 1:1 and 1.1:1 revealed that there is a significant difference between the P:M ratios ($p<0.05$). Similarly there is a significant difference in setting time ($p<0.05$) among the compositions tested. Setting times of microspheres cement decrease with an increase in P:M, while nanospheres-containing cements exhibited an increase in setting time with increasing P:M. Studies of the effect of powder-to-liquid ratio (P:L) on the setting properties of commercial cements suggest that a reduction in setting time is expected with a increase in the P:L ratio. The addition of a cross-linked phase in the cement matrix resulted in lower exotherms and longer setting times for both cements containing cross-linked PMMA microspheres and nanospheres, without promoting increasing viscosity and deleterious effects on the mechanical properties of the material. In addition to the improved curing properties of the two-solution cements, the incorporation of a reinforcing cross-linked phase may also improve the mechanical properties of this material.

Example 11

Viscosity Behavior of Novel Two-Solution Bone Cements

This Example describes the measurement of the static viscosities of the cements containing cross-linked PMMA beads of an embodiment of the present invention and the standard formulation. The static viscosity measurements were performed to evaluate the effect of the addition of cross-linked PMMA particles on the rheological behavior of two-solution cement formulations. Low viscosity coupled with a simultaneous decrease in the percentage of monomer is a desirable property in cements used for the treatment of vertebral compression fractures. Since the standard two-solution cement has a relatively high viscosity for a low polymer-to-monomer ratio, cross-linked spheres were added to the typical formulation in an attempt to lower viscosity and extend the application of the this material.

The static viscosities were measured using a digital viscometer (Brookfield viscometer DV-E) equipped with a coaxial spindle (SC4-14) and water-jacketed sample chamber (SC4-6R). The rheological measurements were performed at room temperature and at variable rotational speeds (from 1 to 100 rpm), depending on the range of viscosities of the different compositions, using the same spindle to perform all of the measurements. Shear rate is proportional to speed for a given spindle and for the combination of spindle/chamber used, taking into account geometry, this parameter was given by multiplying rotational speeds by a conversion factor 0.4. Prior to the start of the experiments, the instrument was calibrated using silicone oil calibration standards (Brookfield Engineering Laboratories Inc.) to ensure accurate readings within an error of +/−1% of any full scale spindle speed/viscosity range.

Cements were prepared, as described in the previous Example, and tested after a period of at least 3 days following mixing to allow complete swelling of the cross-linked particles in the cement solution. The compositions shown in Table 2, supra, were measured as well as the viscosity of microspheres-containing cements in a P:M range from 1:1 to 1.4:1 with $P_b:P_l$ from 1:1 to 4:1. However, at elevated concentrations of cross-linked particles a more powdery morphology resulted, making measurements of viscosity more complex due to quick wetting of the solutions. Therefore, these compositions are described more qualitatively in terms of suitability for use in KP and VP applications. Three measurements of each composition were performed at different shear rates and the average viscosity and standard deviation are reported herein.

Figure 14:
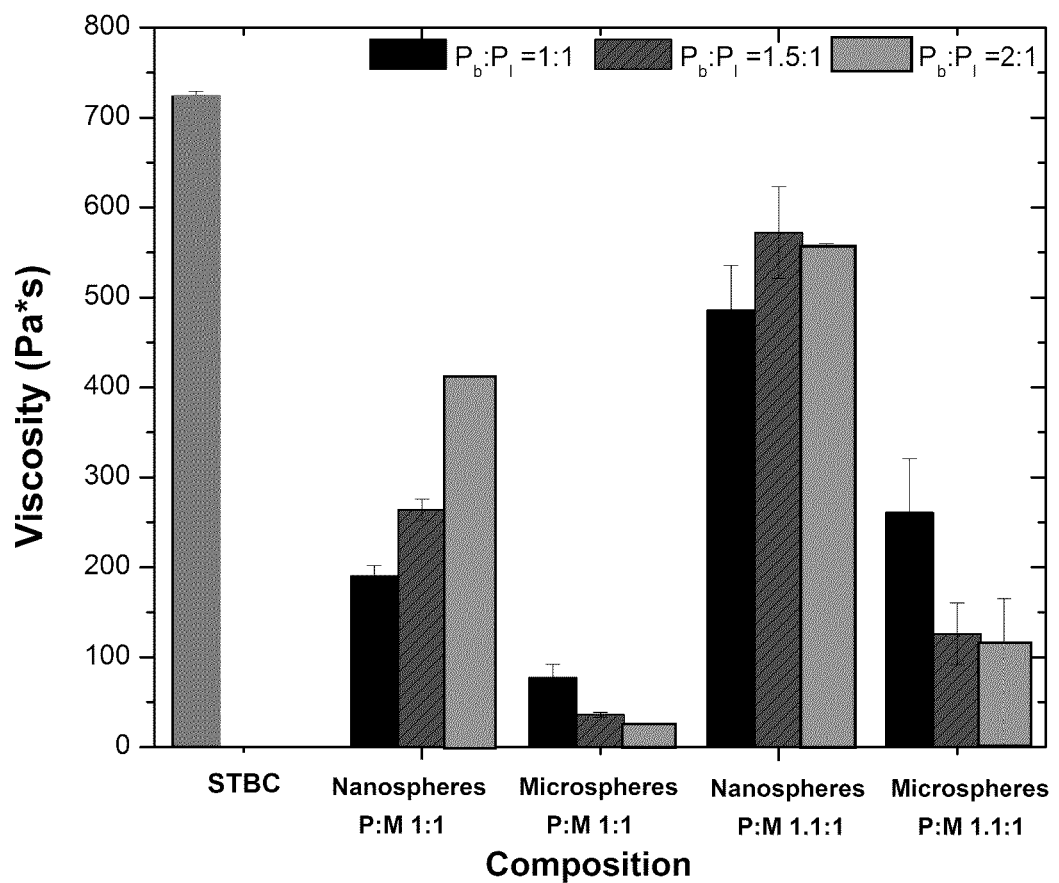
FIG. 14 shows the results of a comparison between viscosities of standard and modified-two solution bone cements at fixed shear rate (4.8 s$^{-1}$), according to an embodiment of the present invention.

The results illustrated in FIG. 14 show a comparison between viscosities of standard and modified-two solution bone cements at fixed shear rate (4.8 s$^{-1}$). From this data it is evident that the addition of cross-linked PMMA nanospheres and microspheres significantly reduced viscosity (p<0.05) in comparison to the standard two-solution formulation. Cements composed of microspheres showed lower viscosities than cements prepared with nanospheres at the same P:M and $P_b:P_l$ ratios. The higher viscosity achieved with nanospheres-containing cements is a result of the increased surface area of the particles, and therefore improved diffusion of monomer into the smaller particles. This fact is confirmed by the higher swelling coefficients in MMA (Q) obtained for nanospheres in comparison to microspheres, 1.26 and 0.98 ml/g, respectively. Cements containing nanospheres and microspheres showed particular rheological behavior with the addition of increasing contents of cross-linked particles in the powder mixture ($P_b:P_l$ ratios).

Figure 15:
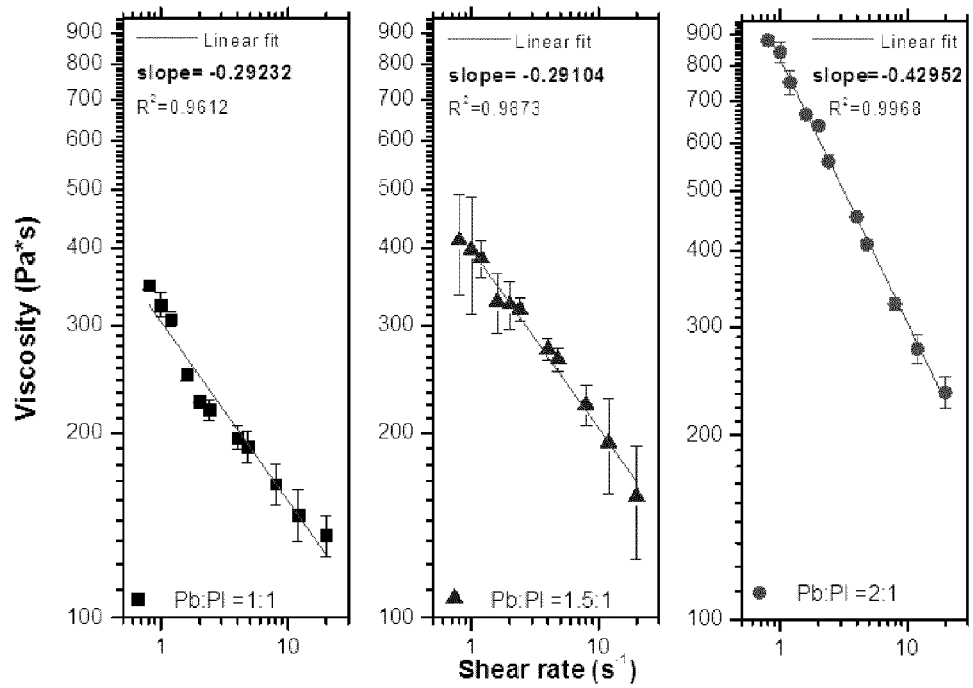
FIG. 15*a-b* show graphical plots illustrating viscosity as a function of increasing shear rate of nanospheres-containing cements (log-log scale), according to an embodiment of the present invention.
Figure 15:
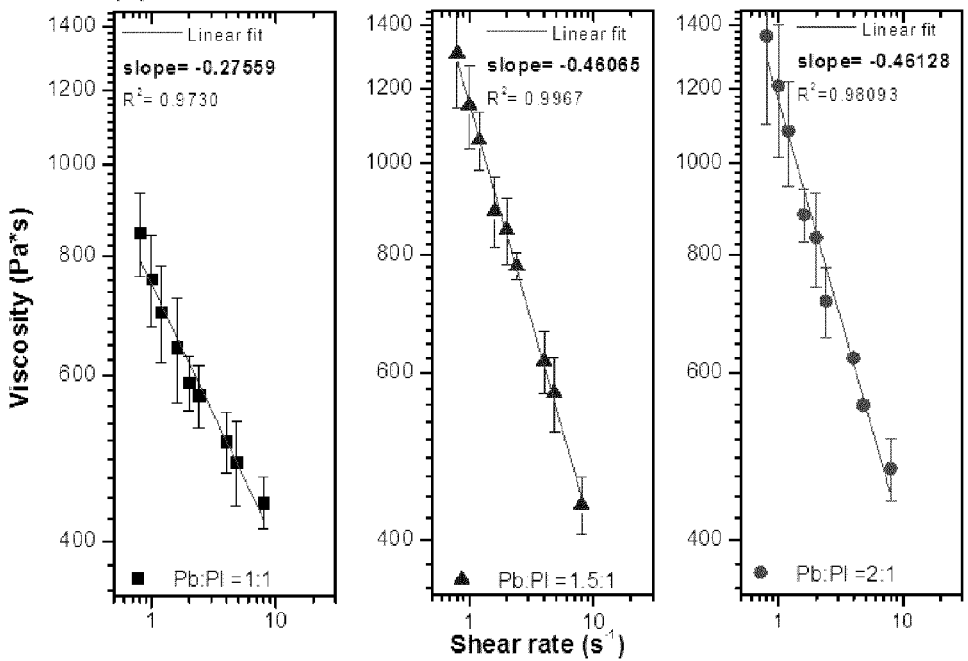
Figure 16:
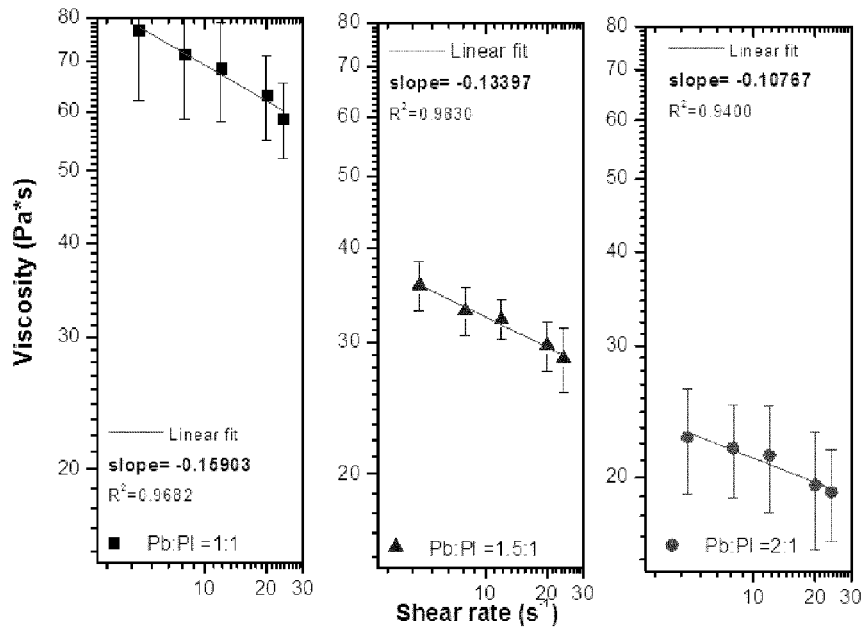
FIG. 16*a-b* show graphical plots illustrating viscosity as a function of increasing shear rate of nanospheres-containing cements (log-log scale), according to an embodiment of the present invention.
Figure 16:
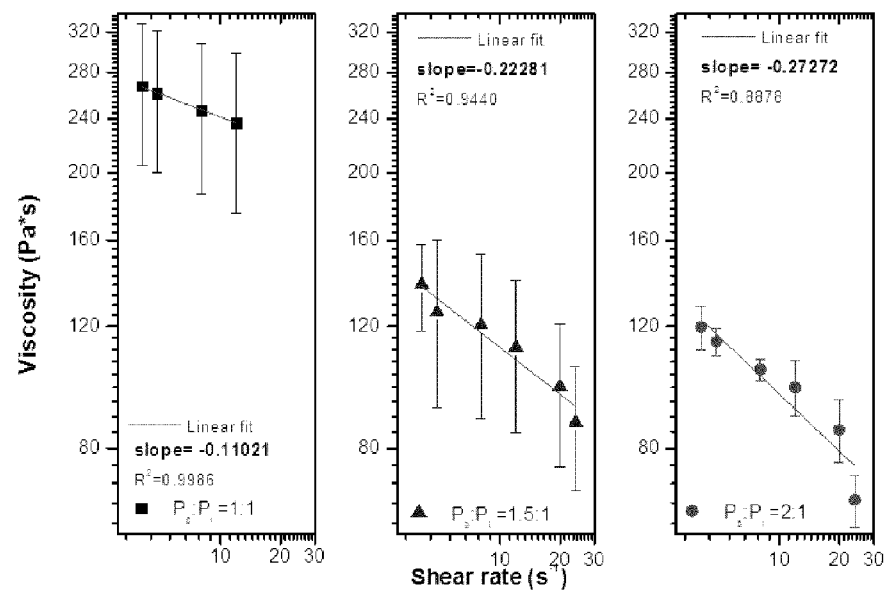

FIGS. 15-16 show graphical plots illustrating viscosity as a function of increasing shear rate of nanospheres-containing cements (log-log scale). The results in FIGS. 15 and 16 illustrate the range of viscosities measured at increasing shear rates for cements prepared with nanospheres and microspheres, respectively. The data is presented in double log plots for the different compositions compared (Table 2, supra). The slopes of the regression lines shown in FIGS. 15 and 16 give the type and degree of non-Newtonian flow, in which a slope zero would imply Newtonian behavior. Cements containing nanospheres exhibited an increase in viscosity with increasing volume fraction of particles in the mixture (highly non-Newtonian behavior), in which slopes varied from −0.29 to −0.43 with increasing $P_b:P_l$ for a P:M of 1:1 and from −0.27 to −0.46 for a P:M of 1.1:1. Cements containing microspheres showed the opposite behavior with respect to particle concentration, with decreasing viscosity at increasing $P_b:P_l$ ratio in the cement mixture. This cement also showed a lower degree of shear thinning with slopes varying from −0.16 to −0.10 with increasing $P_b:P_l$ ratio at a P:M of 1:1 and from −0.11 to −0.27 at a P:M of 1.1:1. STSBC was more pseudoplastic than microspheres-containing cements with a slope of −0.43 (data not shown).

Analyzing individual curves of viscosity versus shear rate, it was observed that the viscosity of microspheres-containing cements decreases only slightly with increasing shear over most of the shear rate range, while the viscosity of nanospheres containing-cements decreases almost linearly at higher shear rates (see FIG. 15, showing the linear decrease in viscosity with increasing shear rate at the two P:M ratios studied; FIG. 16 showing microspheres-containing cements presented a slight decrease in viscosity with increasing shear rate in which the slopes from the regression lines were lower than those measured for nanospheres-containing cements (as shown in FIG. 15)). This information is important to estimate the flow behavior of the different cements in restricted environments, such as in a small cannula or needle. Even though the viscosity of nanospheres-containing cement is higher, its more pseudoplastic nature explains the higher flow rate of this material in comparison to cements containing microspheres.

Figure 17:
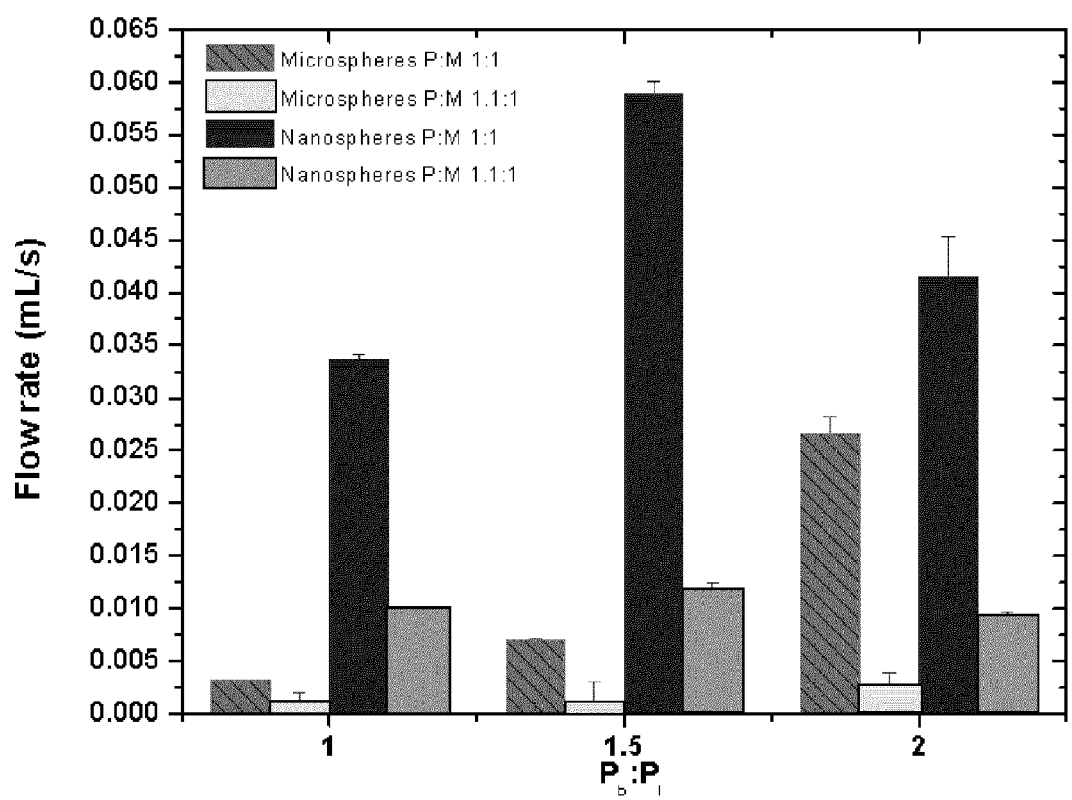
FIG. 17 shows the results of cements containing cross-linked nanospheres and microspheres prepared at different compositions, which were injected with a 12 G and 15 cm long needle for evaluation of injectability, according to an embodiment of the present invention.

Cements prepared at different compositions were injected with a 12 G and 15 cm long needle for evaluation of injectability, and the results are displayed in FIG. 17 (showing flow rate of cements containing nanospheres and microspheres at P:M ratios of 1:1 and 1.1:1). The results show that the flow rate is higher for nanospheres-containing cements, even though these compositions showed significantly higher viscosity than cements prepared with microspheres.

The observation of a weaker shear thinning behavior of microspheres-containing cements could explain the phenomenon of shear induced demixing observed with these materials. During injection of these cements separation of liquid monomer was visible during delivery. This separation led to clogging of microsphere particles in the delivery needle, which decreased flow rate significantly during injection. Even though the viscosity of nanospheres-containing cements is increased in comparison to microspheres, the injectability of these cements is suitable at a P:M of 1:1 and 1.1:1 at the $P_b:P_l$ ratios compared, as shown in FIG. 17. Above a $P_b:P_l$ ratio of 1.5:1 the mixture becomes very gritty and highly volatile, which made it difficult to measure viscosity due to the quick drying of the dough. At compositions above a P:M of 1.1:1 the increase in viscosity achieved with the addition of higher loads of nano spheres would not make this material suitable for delivery through small needles. Microspheres-containing cements, on the other hand, showed a decrease in viscosity with increasing volume fraction of particles. Viscosity decreased with an increase in $P_b:P_l$ at all P:M ratios explored, increasing with an increase in the P:M ratio. This decrease in viscosity, however, is apparent for $P_b:P_l>2.5$, since at these compositions the cements showed a very gritty and dry handling, which prevented continuing flow in the viscometer. Cement preparations above a P:M of 1.2:1 exceed the viscosity of the standard two-solution formulation. The range of viscosities suitable for injection is shown in FIG. 14.

The increase in viscosity achieved with the addition of a larger volume fraction of nanospheres in the cement solutions and the enhancement in non-Newtonian behavior observed for nanospheres-containing cements are consistent with previous results in the literature. The improved injectability of cements containing nanoparticles is a result of the more pronounced shear thinning achieved with the addition of smaller particles. The addition of cross-linked particles in the standard two-solution bone cement formulation was demonstrated to be an effective method to tailor viscosity making this material suitable for applications in the treatment of vertebral compression fractures.

The range of viscosities measured for cements modified with cross-linked PMMA microspheres and nanospheres combined with longer setting times must enable efficient delivery of material into the appropriate sites of fractured vertebral bodies, providing interdigitation with the cancellous bone. The addition of cross-linked nanospheres and microspheres in Examples 10 and 11 were shown to reduce the maximum exotherm when higher volume fractions of particles are employed and to significantly increase the setting time. Likewise, viscosity was significantly reduced in comparison to the standard formulation at higher polymer-to-monomer ratios. Taking into account that the standard two-solution bone cement has been shown to exhibit superior properties and easy preparation and handling, the modification of these cements thorough the addition of cross-linked particles was demonstrated to successfully tailor the viscosity and exothermal properties of this material, making it more suitable for applications in the treatment of compression fractures.

As detailed in some of the previous Examples, the viscosity of two-solution cements can be manipulated by subtle changes in the polymer-to-monomer ratio (denoted by P:M, g PMMA/100 mL MMA) and by the addition of cross-linked beads in the linear polymer phase. This additional variable involves mixing of cross-linked microspheres or nanospheres (denoted by $P_b$) with the linear PMMA powder (denoted by $P_l$) at fixed ratios. It was discussed that increasing the P:M ratio up to 1.4:1 significantly increased the viscosity of two-solution cements prepared with cross-linked PMMA microspheres, however increasing the $P_b$:$P_l$ ratio at a fixed polymer-to-monomer composition had the effect of decreasing viscosity (up to a 2:1 ratio). This disclosure confirmed the viability of tailoring viscosity without compromising the mechanical performance of two-solution cements for extended applications.

In the following Examples, the effects of the addition of $ZrO_2$, in concentrations tuned for fluoroscopic visualization, on the material properties of novel two-solution bone cements modified by the addition of cross-linked PMMA nanospheres or microspheres in the powder phase are described. The influence of increasing radiopacifier concentration on the compressive strength, porosity, viscosity and curing parameters of these cements is also discussed.

Example 12

Cement Formulations and Powder Morphology

This Example describes the synthesis of PMMA microspheres and PMMA nanospheres. An additional variable in the modified two-solution cements of an embodiment of the present invention is the presence of two polymer phases: 1) dissolved linear PMMA ($P_l$) and 2) dispersed cross-linked PMMA microspheres or nanospheres ($P_b$). The linear PMMA (80,000 g/mol) was used as received (Dajac Laboratories, Feasterville Pa., USA) and the cross-linked beads were synthesized via two different polymerization techniques.

Briefly, PMMA microspheres were synthesized via suspension polymerization of methyl methacrylate (MMA), 7.5% v/v (Fluka) using water as the suspension medium, azobisisobutyro-nitrile (AIBN), 0.1% w/v (Sigma-Aldrich) as the initiator, poly-vinyl alcohol (PVA), 2% w/v (Sigma-Aldrich) as the stabilizer and ethylene glycol dimethacrylate (EGDMA), 25% v/v (Aldrich) as the cross-linker agent. Microspheres presented a relatively high polydispersity with diameters in the range 20-100 μm.

PMMA nanospheres were synthesized via boiling temperature soap-free emulsion polymerization of MMA (6.25% v/v), using water as the dispersion medium, potassium persulfate (KPS), 0.1% w/v (Sigma-Aldrich) as the initiator and EGDMA (25% v/v) as the cross-linker. Resulting nanospheres were subjected to post-synthesis centrifugation for separation of supernatant and cleaning, followed by lyophilization for drying. This technique allows for the synthesis of monodisperse nanospheres ranging in size from 300 to 330 nm. For the preparation of two-solution cements, benzoyl peroxide (BPO) (Aldrich), N,N-dimethyl p-toluidine (DMPT) (Aldrich), MMA (Fluka) and $ZrO_2$ (Aldrich) were used as received without further purification. KyphX HV-R (Kyphon Inc, Sunnyvale, Calif.) containing 30% $BaSO_4$ was used as the control for the compression experiments and optical density measurements. This cement has been broadly used clinically in the treatment of vertebral compression fractures due to its low initial viscosity and extended dough time as compared to other commercial cements.

Example 13

Standard Cements Preparation

This Example describes the preparation of the standard two-solution cement composed of linear PMMA has been described by Hasenwinkel and coworkers (see Hasenwinkel et al, *A novel high-viscosity, two-solution acrylic bone cement: effect of chemical composition on properties*, J. Biomed Mater Res 1999; 47:36-45; and Hasenwinkel et al, *Effect of initiation chemistry on the fracture toughness, fatigue strength, and residual monomer content of a novel high-viscosity, two-solution acrylic bone cement*, J Biomedical Materials Research 2002; 59, 411-421), and the preparation of modified two-solution cements of an embodiment of the present invention.

Briefly, cartridges of standard two-solution formulation were prepared at a 0.9:1 P:M ratio.

For the modified two-solution cement compositions, first the desired ratio of cross-linked nanospheres or microspheres ($P_b$) to linear PMMA ($P_l$) was determined. These two components were massed and mixed together forming the powder phase (P) of the subsequent mixture. A fixed 1:1 P:M ratio with 1.5:1 $P_b$:$P_l$ was used throughout the course of the experiments and this composition was specifically selected based on handling and injectability properties. Next, part of the total MMA volume was split and added to two graduated cylinders, in which one was mixed with 1.25 g of BPO (1.25 g/100 mL MMA) and the other with 0.7 mL DMPT (0.7 mL/100 mL). The two mixtures BPO/MMA and DMPT/MMA were transferred to two polypropylene cartridges followed by the addition of the powder phase. The remaining MMA volume was mixed with zirconium dioxide ($ZrO_2$) in concentrations of 5, 20 and 30% (w/v), vigorously agitated and transferred to the polypropylene cartridges. Radiolucent cements were also made for comparison. The polypropylene cartridges were sealed, vigorously agitated by hand and placed in a rotating drum mixer for 18 hours. Following mixing, the cartridges were stored upright at 4° C. Upon demand, the solutions can be mixed through a static mixing nozzle. KyphX was prepared according to manufacturer instructions.

Example 14

Preparation of Samples for Mechanical Testing and Optical Density Measurements

This Example describes the preparation of the standard two-solution cement composition, and the modified two-solution cement compositions (as described in the previous Example), with $ZrO_2$. Cements of all three compositions were prepared at 0, 5, 20 and 30% $ZrO_2$ and injected into a Teflon mold consisting of cylindrical holes, each 6 mm in diameter and 12 mm height, for the casting of compression samples as per ASTM standard F451-99a. The cylindrical samples were allowed to polymerize in the mold for 1 hour followed by 24 hours of curing in air after removal from the mold. The specimens were sanded flush with 400-grit sand paper and were visually inspected for defects. Samples presenting external voids or defects greater than 0.5 mm were excluded. Three samples from each composition were randomly selected from the pool of samples and imaged with X-ray for evaluation of optical density. Measurements of sample height and diameter were taken with a digital micrometer.

Example 15

Optical Density Measurements and Porosity Evaluation

This Example describes optical density measurements of the standard two-solution cement composition, and the modified two-solution cement compositions with $ZrO_2$ (as described in the previous Example).

Optical density measurements were obtained from the digital x-ray images. These images were taken in air at an x-ray tube voltage of 42 kV. This voltage can give excellent information about details (small pores, fractures) in small bone cement specimens when they are studied surrounded by air.

The contrast in an image on an electronic display or monitor is in the form of different brightness or brightness ratios between various points within the image area. Radiopacity (or contrast) is determined by comparing the images of the test specimen and its background on the x-ray film or digital image. The optical density values vary from 0 to 255. Kjellson et al defined contrast as a local difference ($\Delta I$) in the transmitted x-ray intensity through a subject compared with the transmitted x-ray intensity through the adjacent background as:

$$\text{Contrast} = \frac{I_{max} - I_{min}}{I_{max}} \quad (1)$$

Where, $I_{max}$ represents transmittance through the background (or brightness) and $I_{min}$ the transmittance of the subject (see Kjellson F, Almen T, Tanner K E, McCarthy I D, Lidgren, *Bone cement X-ray contrast media: A clinically relevant method of measuring their efficiency*, J Biomed Mater Res B: Appl Biomater 2004; 70B:354-361).

Photoshop (Adobe Version 8.0) was used to measure the gray scale (brightness index) of the specimens and of the immediately adjacent background. A line was drawn parallel to the sample vertical axis and 15 measurements of brightness were taken randomly along this line paired with the immediately adjacent background for each group of samples (5 random measurements in each specimen). The contrast was determined using equation (1) and average contrast and standard deviations were calculated for each group of samples. Differences in contrast with increasing concentration of radiopacifier for groups of cements prepared with nanospheres, microspheres, and STSBC were statistically evaluated using two-way ANOVA with simple effect analysis at a level of significance of 95%.

The distribution of pores within the samples was qualitatively characterized using scanning electron microscopy (SEM-JEOL 5600) in both secondary and backscattered electron imaging. Prior to imaging, the samples were cross-sectioned and gently polished with running water and sand paper grits-600 and 1200, and the polishing was completed with an alumina solution (0.05 µm) until obtaining a minor-like surface free of scratches. The polished surface was gold sputtered for 80 seconds and SEM micrographs were taken with voltages in the range 10-13 kV.

Figure 18:
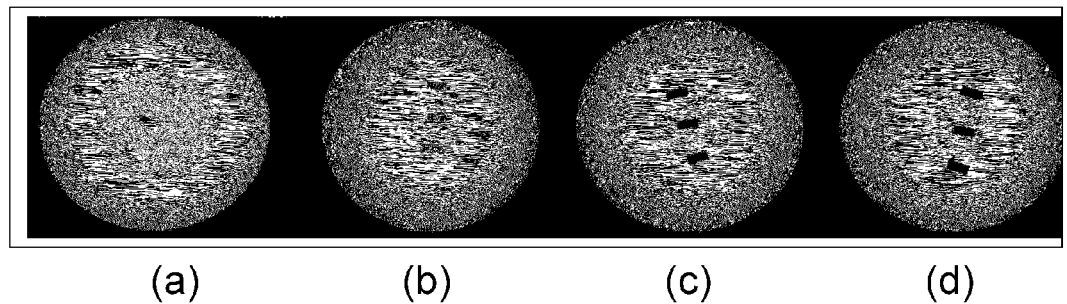
FIG. 18 shows x-ray images of modified two-solution cements prepared with nanospheres at (a) 0% $ZrO_2$ (b) 5% $ZrO_2$ (c) 20% $ZrO_2$ and (d) 30% $ZrO_2$, according to an embodiment of the present invention.

The results show that optical density increased linearly as a function of radiopacifier concentration in the three two-solution formulations evaluated. Radiographs of the various cement preparations were obtained as illustrated in FIG. 18, and the optical densities of all compositions are compared in FIG. 19. Specimens without $ZrO_2$ were not completely transparent to x-rays.

FIG. 18 shows x-ray images of modified two-solution cement prepared with nanospheres at (a) 0% $ZrO_2$ (b) 5% $ZrO_2$ (c) 20% $ZrO_2$ and (d) 30% $ZrO_2$. There is an increase in contrast with increasing concentration of radiopacifier up to 30%. The cement prepared at 0% $ZrO_2$ was not completely transparent to x-rays.

Figure 19:
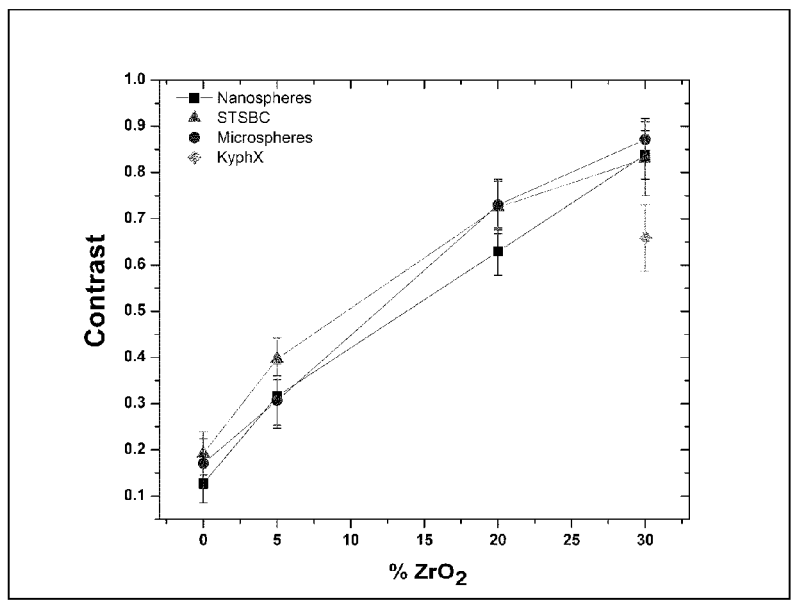
FIG. 19 shows the contrast values comparison for two-solution cement preparations (standard and modified with microspheres and nanospheres) with increasing radiopacifier concentrations, according to an embodiment of the present invention.

FIG. 19 shows the contrast values comparison for two-solution cement preparations (standard and modified with microspheres and nanospheres) with increasing radiopacifier concentrations. X-ray images of cylindrical bone cement samples were taken in air at an x-ray tube voltage of 42 kV. KyphX (♦) presented lower optical density than the three cement formulations prepared at 30% $ZrO_2$, presenting contrast values in the range of two-solution cements containing 20% $ZrO_2$. The data shows a significant increase in radiopacity with increasing concentration of $ZrO_2$ for STSBC (▲), nanospheres (■) and microspheres (●) cements (p<0.05).

As shown in FIG. 19, the contrast values between the area corresponding to the specimen and the background increased with increasing $ZrO_2$ content across the three formulations. The standard deviations are somewhat high, probably due to the presence of internal porosity and inhomogeneity of the cement matrices. The standard deviations are particularly high for KyphX and standard two-solution compositions. There is a significant increase in contrast with increasing concentration of $ZrO_2$ in all the three cement formulations (p<0.05). Also, there is a significant difference in contrast (p<0.05) among the three cement compositions compared at 0% (except between STSBC and microspheres), 5% (except between nanospheres and microspheres) and 20% (except between microspheres and STSBC). At 30% $ZrO_2$ the contrast values of cements containing nanospheres, microspheres or the standard formulation are not significantly different (p>0.05). KyphX (30% $BaSO_4$) has contrast in the range found for 20% $ZrO_2$ with the three different cements and has lower contrast than the cements prepared at 30% $ZrO_2$.

These results are in agreement with the contrast values measured by Kjellson et al for acrylic bone cements specimens containing 5% (contrast value 0.339) and 15% (contrast value 0.733) $ZrO_2$ imaged under the same x-ray tube voltage (40 kV) and conditions applied as described herein (see Kjellson F, Almen T, Tanner K E, McCarthy I D, Lidgren, *Bone cement X-ray contrast media: A clinically relevant method of measuring their efficiency*, J Biomed Mater Res B: Appl Biomater 2004; 70B:354-361). Indeed cements containing $ZrO_2$ are expected to have higher opacity than those containing $BaSO_4$ when imaged at an accelerating voltage of 40 kV because this voltage produces its peak intensity just above the zirconium K-border (18 kV). These results point out the possibility of reducing the concentration of radiopacifier below 30% when $ZrO_2$ is used instead of $BaSO_4$. This last observation is important considering that viscosity was observed to increase with the addition of increasing concentrations of radiopacifier.

Example 16

Compression Testing

This Example describes compression testing of the standard and modified bone cement compositions, as described in the previous Examples. Standard and modified two-solution bone cements and the control KyphX were subjected to compression testing in an MTS hydraulic system (model #) with a 22.5 kN capacity load cell. The cylindrical samples were tested at room temperature at a displacement rate of 0.05 mm/s. The specimens were placed individually between two steel parallel platens and compressed to 50% strain. Five samples of each composition were tested in compression. Stress and strain data were obtained by dividing the load and deformation by the cross-sectional area and initial length of the specimens, respectively. Ultimate compressive stress was defined as the peak stress while compressive yield strength was determined using the 2% offset method of the Hookean portion. Compressive modulus was calculated from the slope of the linear region of the stress-strain curve. Two-way ANOVA with simple effects analysis was applied at a level of significance of 95% to determine the effect of cement composition and radiopacifier concentration on each variable measured in the compression test (ultimate compressive stress, modulus and strain to failure).

Porosity

Porosity was qualitatively evaluated in cylindrical samples casted for compression testing, as described above. The different cement preparations presented particular porosity distribution as shown in FIG. 20.

Figure 20:
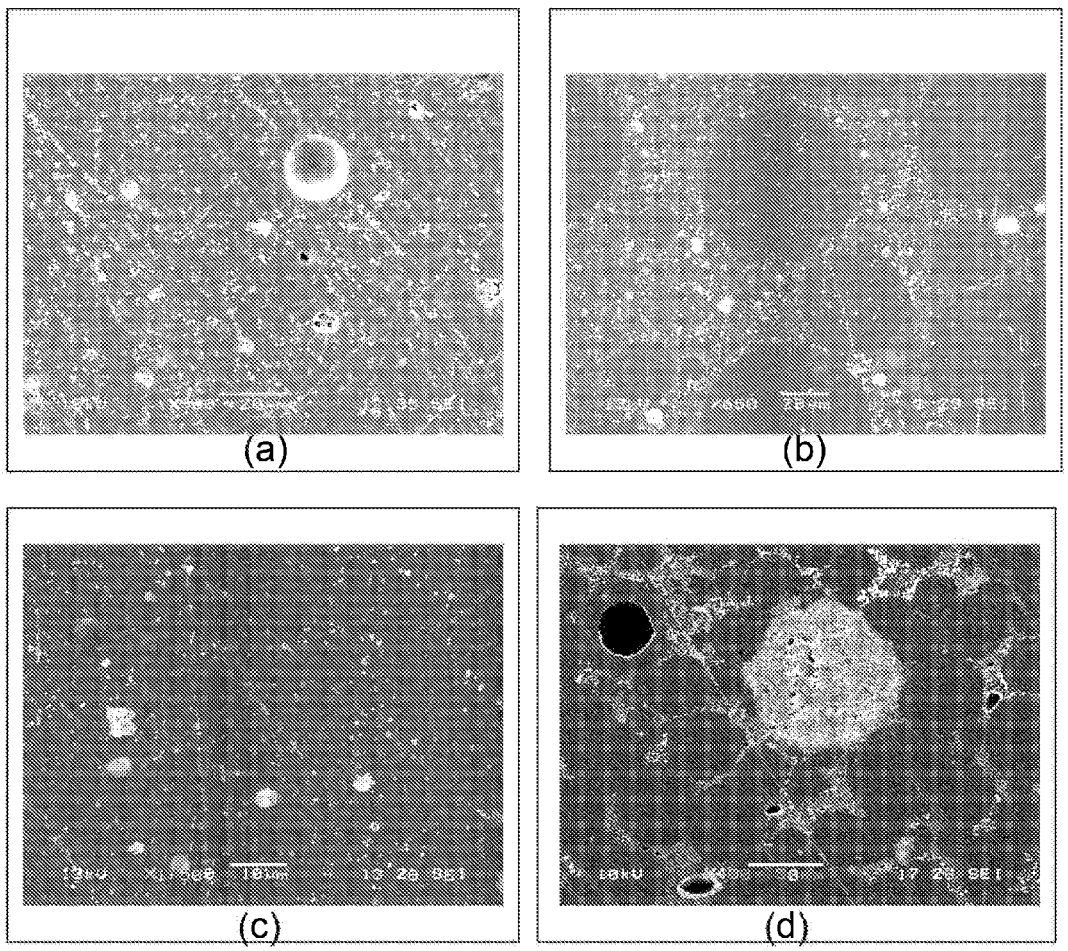
FIG. 20 shows secondary electron SEM images illustrating porosity distribution of the standard and modified bone cement compositions (mid-section of cylindrical specimens prepared at 30% $ZrO_2$), according to an embodiment of the present invention.

FIG. 20 shows secondary electron SEM images illustrating porosity distribution of the standard and modified bone cement compositions (mid-section of cylindrical specimens prepared at 30% $ZrO_2$). FIG. 20 shows (a) STSBC (900×) (b) microspheres-containing cements (650×) (c) nanospheres-containing cements (1500×), and (d) KyphX (400×) at 30% $BaSO_4$. There is a presence of micropores in the standard two-solution and KyphX formulations. White agglomerations are evidence of radiopacifier clumps, which are larger for the KyphX formulation.

As shown in FIG. 20, clumps of radiopacifier can be clearly identified as white agglomerates on the surface. A visual inspection of the cross-sections of the samples revealed that the incidence of macropores (defined as pores with diameter $\geq 1$ mm) was more frequent in cement preparations with the standard two-solution formulation (a) and KyphX (d). The KyphX formulation showed the typical $BaSO_4$ agglomeration discussed in the literature, with large clumps (about 50 µm in diameter) present all over the surface cross-sections. PMMA beads were also observed surrounded by regions of polymer matrix containing a great extent of microporosity (defined as pores with diameter <1 mm). Microspheres-containing cements showed pores formed by the removal of polymer beads from the cement matrix (about 100 µm in diameter). Conversely, nanospheres-containing cements presented very few macropores distributed on the outer interfaces of the samples, and only very small micropores were visible on the cross-sections. Qualitatively there was an evident difference in the appearance of the matrices containing $ZrO_2$ and $BaSO_4$. The larger extent of pores in the KyphX cement might translate into lower strengths and nucleation sites for crack propagation. Kurtz et al observed that three different bone cements presented porosity in which $BaSO_4$ was observed as an agglomerate of particles with typical length scales on the order of 1 µm (see Kurtz S M, Villarraga M L, Zhao K, Edidin A A, *Static and fatigue mechanical behavior of bone cement with elevated barium sulfate content for treatment of vertebral compression fractures*, Biomaterials 2005; 26:3699-3712). In this paper, Kurtz et al found no correlation between the $BaSO_4$ content and the incidence of macroporosity, suggesting that other factors, mainly the composition of the cement matrix, may influence the generation of large pores.

It is important to point out that $ZrO_2$ was added to two-solution cements instead of $BaSO_4$ due to a detrimental effect observed when mixing this contrast agent into solutions containing nanospheres. $BaSO_4$ led to the formation of a powdery mixture of difficult handling, which could not be mixed or delivered through a static nozzle. It could be argued that the increased surface area of the particles exposed to the monomer solution (nanospheres plus $BaSO_4$ particles, which have size distribution in the nano-scale range) induced this effect due to more difficult wetting. However, even at very low concentrations of $BaSO_4$ (2 and 5%) the same detrimental effect was observed. This observation indicates that $BaSO_4$ may be inappropriate for the modified two-solution cements, described herein. This negative effect was not observed when $ZrO_2$ was added to the solutions, on the contrary the cements presented suitable handling allowing the casting of samples with only a few signs of external porosity or clumping of radiopacifier.

Example 17

Compression Testing and Fracture Analysis

This Example discusses the results of compression tests that were performed to investigate the effect of the addition of increasing concentrations of $ZrO_2$ on the mechanical behavior of two-solution cement preparations. The results show that the static compressive strength of cements containing cross-linked beads exceeded the 70 MPa minimum specification (ASTM F451-99a, as should be understood by those of ordinary skill of the art) for all the compositions investigated, except STSBC containing increasing content of $ZrO_2$.

Figure 21:
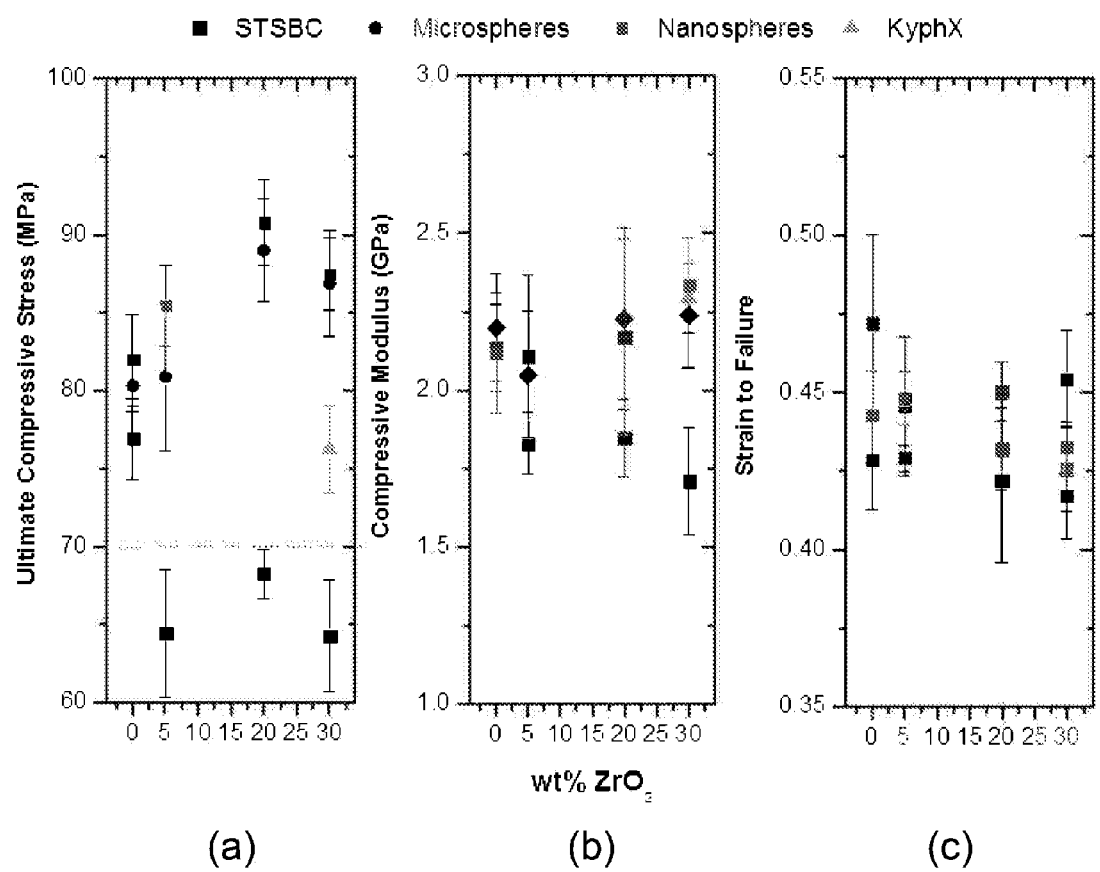
FIG. 21 shows an overall comparison between the compressive properties (compression strength, modulus and strain to failure) of modified cements containing microspheres and nanospheres, and the standard formulation prepared with increasing concentrations of $ZrO_2$, according to an embodiment of the present invention.

FIG. 21 shows an overall comparison between the compressive properties (compression strength, modulus and strain to failure) of modified cements containing microspheres and nanospheres, and the standard formulation prepared with increasing concentrations of $ZrO_2$. A comparison was also made to KyphX at 30% radiopacifier. Compressive yield strength presented values close to the ultimate compressive stress, therefore the data was omitted. FIG. 21 shows ultimate compressive stress (a), compressive modulus (b) and strain to failure (c). Cements prepared with cross-linked particles show significantly higher compressive strength than STSBC ($p<0.05$). The compressive strength of the KyphX cement is lower than the strengths of the modified two solution cements but higher than STSBC.

Microspheres and nanospheres containing cements presented surprisingly high compressive strength, as shown in FIG. 21($a$). This parameter increased significantly with an increase in radiopacifier concentration up to 30% for both formulations ($p<0.05$), reaching compressive strength values higher than 90 MPa (nanospheres-containing cement at 20% $ZrO_2$). In contrast, the standard two-solution formulation showed a significant decrease in compressive strength with an increase in $ZrO_2$ content ($p<0.05$). Simple effects analysis indicated that the mean compressive strength of nanospheres and microspheres-containing cements are not significantly different ($p>0.05$) (the only significant difference in strength was found at 5% $ZrO_2$); however there is a significant difference between the strengths of these two cements and that of the standard two-solution formulation ($p<0.05$) compared at 0, 5, 20 and 30% $ZrO_2$. KyphX showed compressive strength values between the standard two-solution formulation and cements containing cross-linked particles (average approximately 75 MPa). The behavior of the compressive modulus for the three cement formulations and KyphX is illustrated in FIG. 21($b$). There was no significant effect of increasing $ZrO_2$ concentrations on the moduli of cements containing nanospheres and microspheres ($p>0.05$), however STSBC showed a significant decrease in modulus with increasing concentration of radiopacifier in the material ($p<0.05$). Similarly to compressive strength, simple effects analysis indicated that the compressive modulus of nanospheres and microspheres-containing cements are not significantly different ($p>0.05$); however there is a significant difference between the moduli of nanospheres and microspheres-containing cements compared to those of the standard two-solution formulation ($p<0.05$) at 20 and 30% $ZrO_2$. Strain to failure is shown in FIG. 21($c$) for the three cement formulations and KyphX. This parameter shows a significant difference across $ZrO_2$ compositions for microspheres-containing cements and STSBC ($p<0.05$). Contrary, there is no significant effect of $ZrO_2$ concentration on the strain to failure of cements prepared with nanospheres. Simple effects analysis of this parameter also indicated that the strain to failure of nanospheres and microspheres-containing cements are not significantly different; however there is a significant difference between the strains of these two cements and those measured for the standard two-solution formulation ($p<0.05$) (microspheres and STSBC at 0, 20 and 30% $ZrO_2$ and nanospheres and STSBC at 0 and 30%).

The ultimate compressive strength of STSBC cement containing 5, 20 and 30% $ZrO_2$ is below the 70 MPa minimum ASTM requirement. These results indicate that STSBC would not be suitable for the treatment of vertebral compression fractures. The addition of $ZrO_2$ even at a very low concentration (5%) had deleterious effects on the compressive strength of the material. At 30% radiopacifier the results reveal that cements prepared with nanospheres and microspheres have higher compressive strength than KyphX. There is no effect of the PMMA particle size on the compressive properties of two solution-cements containing increasing concentrations of $ZrO_2$, considering the statistical analysis did not indicate any significant differences between microspheres and nanospheres-containing cements in the three parameters evaluated.

The compressive properties measured for modified two-solution cements confirmed that these materials are appropriate to withstand the high loads exerted in the spine and can be designed with sufficiently high levels of $ZrO_2$ to permit visualization under fluoroscopy. Materials properties reported were obtained from compression testing, which is the predominant mode of loading in the spine in vivo. The values reported are higher or in the range of results previously obtained in the literature. For example, Jasper et al measured compressive properties of several conventional commercial cements used in vertebroplasty obtaining compressive modulus ranging from 2.0-2.7 GPa and compressive yield strength and ultimate compressive strength ranging from 50-73 MPa and from 53-80 MPa, respectively (see Jasper L E, Deramond H, Mathis J M, Belkoff S M, *Material properties of various cements for use with vertebroplasty*, J Mater Sci: Mater Med 2002; 13:1-5). $ZrO_2$ in increasing concentrations in modified two-solution cements acted as a rigid reinforcing phase when interacting with the cross-linked beads in the cement matrix. The radiopacifier in this case may have promoted an interaction between the crack fronts and the second phase dispersion, blunting further crack propagation. In contrast, the addition of $ZrO_2$ in standard two-solution cement did not reinforce the matrix, even though a fair distribution of the radiopacifier was observed, as illustrated in FIG. 20($a$). Some of the possible reasons for this result are higher porosity associated with the standard formulation and therefore presence of more sites for crack nucleation, higher viscosity of the dough which does not allow for air bubbles to escape during mixing, and lack of the first phase dispersion (cross-linked particles) which is thought to provide a barrier to crack propagation. The combination of cross-linked beads with the second phase dispersion (considering $ZrO_2$ did not produce significant clumping in the material) allowed for improved mechanical anchorage in the cement matrix.

Figure 22:
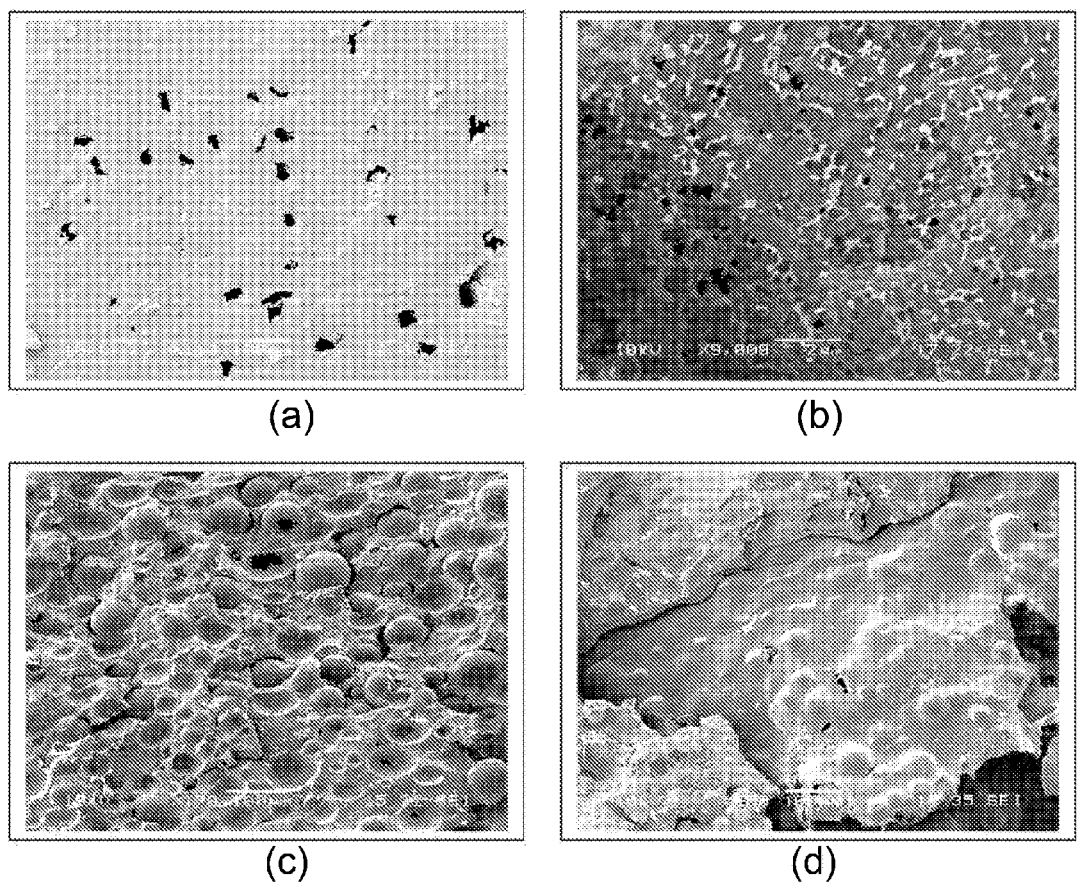
FIG. 22 shows secondary SEM micrographs of fracture surfaces after compression testing illustrating the morphology of the fracture surfaces of samples prepared with 30% $ZrO_2$ for cements containing (a) standard two-solution formulation (110×), (b) modified two-solution containing nanospheres (9000×), (c) modified two-solution containing microspheres (170×) and (d) KyphX at 30% $BaSO_4$ (150×), according to an embodiment of the present invention.

FIG. 22 shows secondary SEM micrographs of fracture surfaces after compression testing illustrating the morphology of the fracture surfaces of samples prepared with 30% $ZrO_2$ for cements containing (a) standard two-solution formulation (110×), (b) modified two-solution containing nanospheres (9000×), (c) modified two-solution containing microspheres (170×) and (d) KyphX at 30% $BaSO_4$ (150×). The nanospheres-containing cement interface is shown at higher magnification in comparison to the other micrographs in order to reveal the nanostructures apparent in the matrix.

The interfaces of the standard two solution formulation (a) showed a very smooth minor-like zone. The fracture surface presented striated areas, which may be an indication of slow stable crack growth. The fracture surface of modified two-solution cement containing nanospheres (b) showed a rough interface. At higher magnifications it is possible to observe a homogeneous nanobeads-matrix structure. Internal cracks propagated in direction to the edge of the sample and not preferentially towards or surrounding beads. Presence of white regions surrounding beads indicates presence of radiopacifier distributed in the matrix. Fracture surfaces of modified standard two-solution cements containing microspheres (c) showed a rougher and grittier appearance. Microspheres embedded in the matrix are clearly seen, the removal of these microspheres created pores in the 50-100 μm range. Voids and microcracks also surrounded the PMMA particles where cracks seemed to grow preferentially through this region. The fracture surface of KyphX (d) presented a very rough and chalky appearance, due to $BaSO_4$ agglomerates, indicating zones with slow crack propagation and crack arrest. The incidence of cracks seems not to increase or decrease with an increasing concentration of radiopacifier for all the formulations evaluated in this study. In addition, the matrices of cements containing nanospheres and microspheres had homogeneous appearance with no substantial clumping of radiopacifier, as shown by the SEM micrographs illustrated in FIG. 20.

Example 18

Viscosity Measurements

This Example describes static viscosity measurements performed in order to evaluate the effect of addition of increasing contents of $ZrO_2$ on the rheological behavior of two-solution formulations. The flow behavior is an important parameter to consider since the actual viscosity of the standard formulation at a P:M 0.9:1 ratio is high for a relatively low polymer-to-monomer ratio. For this reason, cements containing cross-linked particles were designed (as described herein) in an attempt to increase the polymer-to-monomer ratio without subsequently increasing the viscosity of the solutions.

Briefly, the effect of $ZrO_2$ addition in increasing concentrations on the static viscosity of the three cement formulations were evaluated. Rheological measurements were performed with a Brookfield viscometer (DV-E Digital Viscometer) operated with a coaxial spindle and controllable speeds. Measurements were taken at increasing shear rates depending on the viscosity range of each formulation. The cements tested were prepared as described previously. Three measurements of each composition were performed at each shear rate and the average viscosity and standard deviation are reported. Two-way ANOVA with simple effects analysis was performed at a level of significance of 95% to determine the effect of cement composition and radiopacifier concentration on the viscosity behavior.

Figure 23:
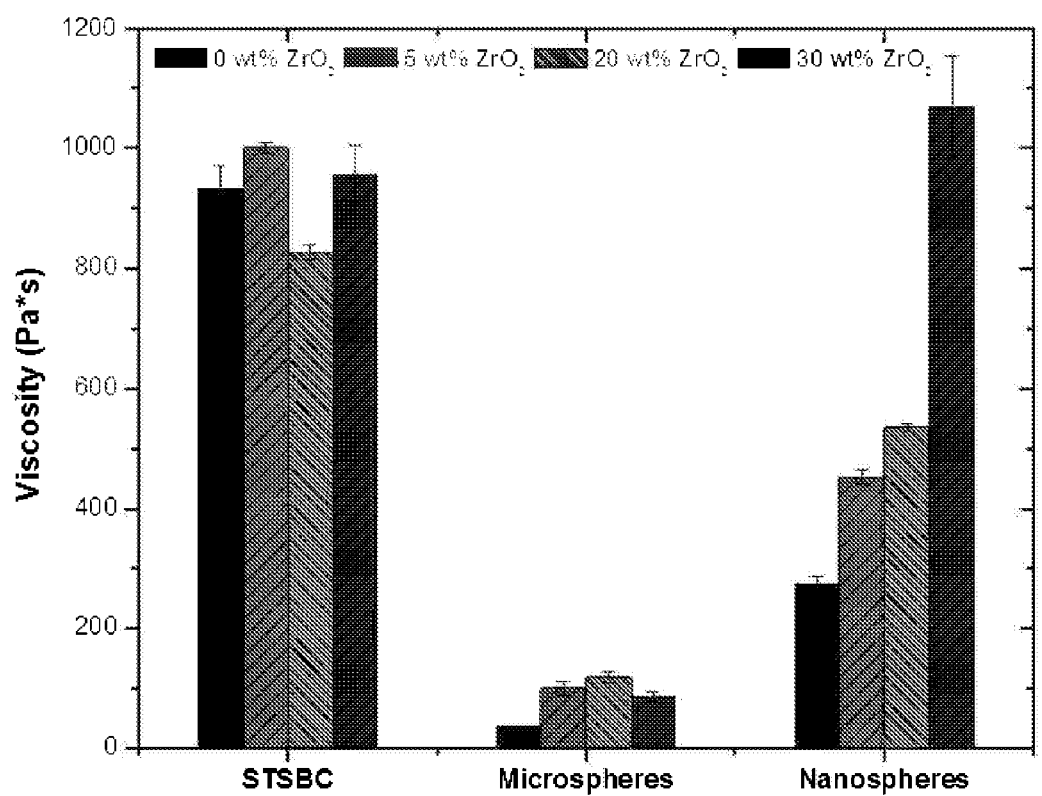
FIG. 23 shows the effect of radiopacifier on the viscosity of cements prepared with STSBC, microspheres and nanospheres, according to an embodiment of the present invention.

FIG. 23 shows the effect of radiopacifier on the viscosity of cements prepared with STSBC, microspheres and nanospheres. Comparison was performed at fixed shear rate (4 $s^{-1}$). The results show that the viscosity decreased (at 0% $ZrO_2$) with the addition of cross-linked particles in the cement matrix. Viscosity of cements containing microspheres and nanospheres were significantly lower than the viscosity of the standard two-solution cements ($p<0.05$).

It is evident from FIG. 23 that there is an effect of radiopacifier on the viscous flow of two-solution cements. Viscosity data is compared at a fixed shear rate (4 $s^{-1}$) for all the three cement compositions. Comparing the three cements in the absence of radiopacifier, it is clear that the viscosity of the solutions decreases with the addition of cross-linked particles. The two-solution cements containing microspheres at 0% $ZrO_2$ showed very low viscosity; indeed the runny nature of this cement would not make it suitable for VP and KP applications due to possible extravasation from the vertebral body. When compared to the STSBC formulation (fixed shear rate of 4 $s^{-1}$), it is shown that the presence of cross-linked microspheres reduced viscosity by about 96% at a P:M 1:1 with $P_b$:$P_l$ 1.5:1 ratio. Cements prepared with cross-linked nanospheres showed higher viscosity than cements containing microspheres. In the absence of radiopacifier the viscosity is about 14% higher than the viscosity measured for microspheres-containing cements; however it is still 70% lower than the initial viscosity of STSBC. The addition of radiopacifier in microspheres-containing cements increased viscosity; however this increase is not significant across $ZrO_2$ concentrations ($p>0.05$) (the only significant difference was observed between 0 and 20% $ZrO_2$). On the contrary, the addition of increasing concentrations of radiopacifier significantly increased the viscosity ($p<0.05$) of cements prepared with nanospheres ($p<0.05$) and significantly affected the STSBC formulation ($p<0.05$) (except there is no significant difference between 0 and 30 and 5 and 30% $ZrO_2$). There is a significant difference among viscosities of the three cement formulations compared at 0, 5, 20 and 30% $ZrO_2$ ($p<0.05$). Simple effects analysis confirmed that the highest viscosity was achieved with nanospheres-containing cement at 30% $ZrO_2$ 1046 Pa*s), followed by STSBC at 5% $ZrO_2$ (1006 Pa*s). The lowest viscosity was measured for microspheres-cements at 0% $ZrO_2$ (35.78 Pa*s).

The substantial increase in viscosity of nanospheres-containing cements in comparison to microspheres at all $ZrO_2$ concentrations is a result of the increased surface area of the beads, which enhances diffusion of the monomer in the particles, and increased volume fraction of particles in the cement mixture. At 30% $ZrO_2$, the nanospheres-containing cements showed difficult handling and slow mixing through a static mixing nozzle, making it unsuitable for delivery with a needle or cannula. On the other hand, at 20% the cement mixed well in the nozzle, making it possible to deliver with a 12 G needle. These viscosity results give a range of compositions suitable for application in the treatment of vertebral compression fractures. Cements containing microspheres can be prepared with high radiopacifier concentrations, while cements containing nanospheres can be prepared with concentrations as high as 20%. Compression tests revealed that the standard formulation containing radiopacifier falls below the minimum ASTM requirement, and combined with the fact that the viscosity of the dough is considerably high it can be concluded that this composition is not adequate for the application discussed herein.

Example 19

Exothermal Testing

This Example describes the measurement of maximum temperatures and setting times for the three different cement types (modified two-solution bone cements with microspheres and nanospheres and the standard solution, described in the previous Examples) containing 0 and 20% $ZrO_2$ in order to discern possible effects of the addition of high concentrations of radiopacifier on the setting characteristics of these cement preparations. As discussed herein, the standard two-solution bone cement has a maximum polymerization exotherm around 100° C. and setting time of about 8 minutes.

Briefly, the exothermal polymerization temperatures and setting times of two-solution cements containing 20% $ZrO_2$ were measured, according to ASTM standard F451 (denominated standard mold, as should be appreciated by those skilled in the art), and compared to the respective formulation containing no radiopacifier added. A smaller custom-designed PTFE mold comprising a total volume of 3 cubic centimeters (denominated 3 CC) was also used to measure the setting characteristics of the cements with the goal of replicating the approximate volume of cement delivered into a vertebral body during vertebroplasty. The maximum exotherm is defined as the peak in the temperature versus time curve during polymerization, while setting time is given by the time corresponding to the average temperature between ambient and maximum temperatures. Maximum temperatures and setting times are reported as the average of three measurements of each composition in both molds. Differences in the maximum exotherm and setting times of the three cement compositions prepared with 0 and 20% $ZrO_2$ were statistically analyzed applying two-way ANOVA with simple effects and Tukey post hoc (for the parameters that did not show significant interaction) at a level of significance of 95%.

Figure 24:
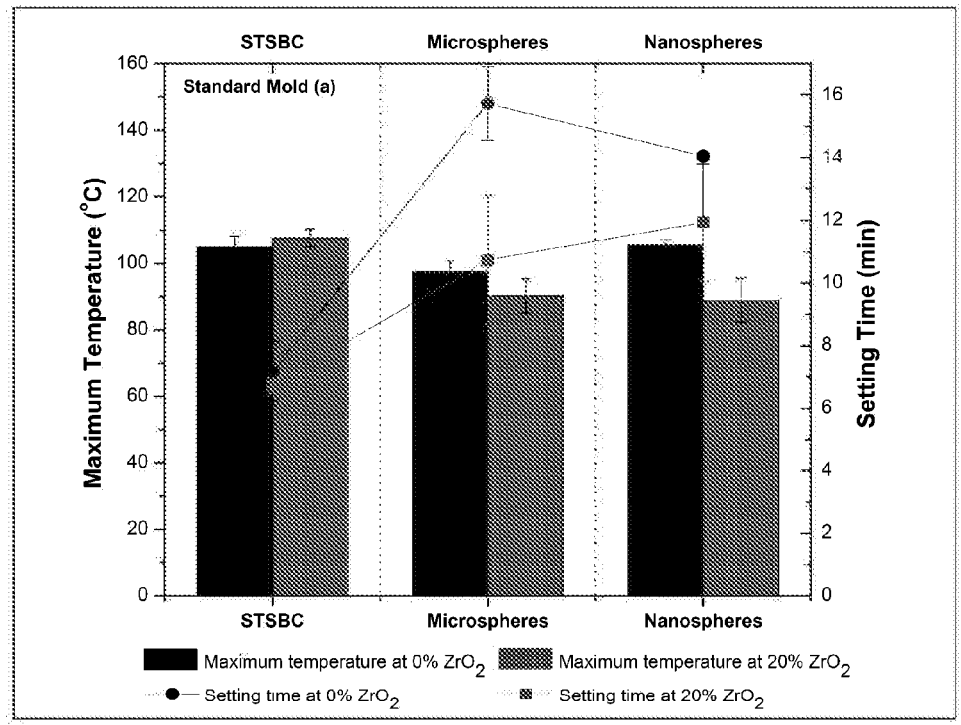
FIG. 24 shows the setting characteristics of cements prepared with nanospheres and microspheres compared at 0 and 20% $ZrO_2$; (a) shows the results obtained with the standard mold, and (b) shows the results obtained with the 3 CC mold, according to an embodiment of the present invention.
Figure 24:
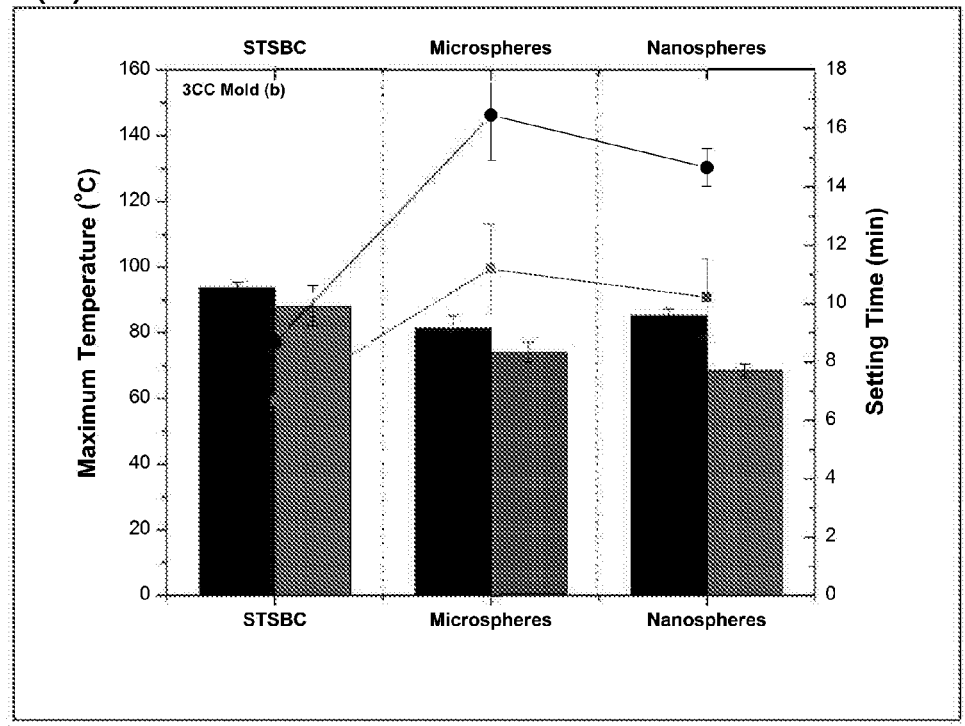

FIG. 24 shows the setting characteristics of cements prepared with nanospheres and microspheres compared at 0 and 20% $ZrO_2$; (a) shows the results obtained with the standard mold, and (b) shows the results obtained with the 3 CC mold. Bars indicate maximum polymerization temperatures and lines and symbols setting times.

As noted, FIG. 24 illustrates the effect of the addition of radiopacifier in the exothermal and setting behavior of standard two-solution, nanospheres and microspheres-containing cements for experiments performed in the standard (a) and custom designed molds (b). It is evident from FIG. 24(a) that in the absence of radiopacifier cements prepared with nanospheres presented maximum exotherm in the range of the standard formulation, while microsphere-containing cements showed lower temperature ($p<0.05$) than the standard formulation. However, the setting times of these cements were significantly increased in comparison to STSBC ($p<0.05$) (using the same initiation chemistry 1.25 g BPO/100 mL MMA and 0.7 mL/100 mL MMA). The addition of 20% $ZrO_2$ produced a significant decrease in maximum exotherm in nanospheres and microspheres cements ($p<0.05$) but not with the standard formulation ($p>0.05$). This decrease was about 10° C. in the maximum polymerization temperature of microspheres and about 15° C. for nanospheres-containing cements. The addition of 20% $ZrO_2$ decreased the setting time of microspheres cements significantly ($p<0.05$) with a reduction of more than 5 minutes; there was also a reduction in setting time for nanospheres-containing cements (about 3 minutes), although not statistically significant. The addition of radiopacifier did not affect the setting time of the STSBC ($p>0.05$). The average maximum temperature of STSBC cement is significantly higher ($p<0.05$) than nanospheres and microspheres-containing cements, both of which did not present significant differences in maximum exotherm ($p>0.05$). Similarly, STSBC had the lowest setting time ($p<0.05$) compared to microspheres and nanospheres cements, which did not show significant differences in setting time ($p<0.05$).

A similar trend is shown in the maximum exotherms obtained with the 3 CC mold. However, there is no indication of interaction between cement type and $ZrO_2$ composition in setting time ($p>0.05$) measured with the smaller mold. Nonetheless, Tukey post hoc tests confirmed that STSBC had the lowest setting time ($p<0.05$) compared to microspheres and nanospheres cements, which did not show significant differences between setting times ($p<0.05$). A decrease of more than 15° C. in the maximum exotherm was measured with the custom-designed mold as compared to the results measured with the standard; however this is an expected result due to the smaller volume of cement surrounding the thermocouple.

The reduction in maximum temperature with the addition of 20% $ZrO_2$ in cements containing nanospheres and microspheres may be associated with the dissipation of energy by the $ZrO_2$ particles in combination with the cross-linked PMMA beads. Since there was no effect of the addition of radiopacifier in the standard-two solution cement ($p>0.05$), which is solely composed of linear polymer, it could be concluded that nanospheres and microspheres acted as an insulator phase in the cements matrix, thereby absorbing and dissipating the excess heat generated during curing of the cement.

The addition of radiopacifier decreased the setting times of cements prepared with cross-linked particles. It is discussed herein that in the absence of radiopacifier the setting time of cements prepared with cross-linked microspheres and nanospheres was longer than that of the standard formulation. The reason for this increase in setting time may be associated with the fact that cross-linked particles swell in monomer, therefore leaving larger amounts of free monomer available in the matrix, which consequently, slow the polymerization process. Thus, when the radiopacifier was added to the cement mixture containing cross-linked particles, the available monomer quickly wetted the $ZrO_2$ particles accelerating polymerization. Even though the setting time of the modified two-solution cements decreased with higher contents of $ZrO_2$, this reduction should not compromise cement injection and handling and, therefore the application in KP and VP. Cements containing high concentration of radiopacifier and nanospheres or microspheres showed appropriate curing properties for applications in the treatment of compression fractures.

The previous eight Examples examined the effect of high concentrations of $ZrO_2$ on the static mechanical properties, porosity and fracture mode, viscosity and curing parameters of novel two-solution cements. The results confirmed the viability of preparing modified two-solution cements containing elevated content of radiopacifier tuned for enhanced visualization under fluoroscopy without degrading the mechanical properties of the material. These cements presented matrices without significant evidence of macroporosity and clumping of the contrast agent, which led to an increase in compressive strength with increasing content of $ZrO_2$. The viscosity of these cements is appropriate as well as the maximum polymerization exotherm and setting times.

In the following Examples, the development of novel two-solution cements containing cross-linked PMMA nanospheres as part of the polymer phase to optimize the material viscosity is described. The novel cements were shown to exhibit reduced viscosity, lower polymerization exotherm, longer setting time and lower concentration of residual monomer in comparison to a standard two-solution bone cement formulation.

As described in the following Examples, PMMA brushes were grafted to the surface of cross-linked PMMA nanospheres in order to improve interfacial bonding of the beads to the cement matrix, allowing for complete substitution of the linear phase of the cement mixture. A goal set forth in these Examples was to develop a novel synthetic pathway, which allows for efficient surface modification of cross-linked PMMA nanospheres for grafting of PMMA nanospherical brushes at high densities. Another goal was to prepare two-solution cements with reduced monomer concentration and lower viscosities by the complete substitution of linear PMMA with PMMA brushes at higher polymer-to-monomer (P:M) ratios.

Example 19

Synthesis of Cross-Linked PMMA Nanospheres

This Example describes the synthesis of cross-linked PMMA nanospheres. The purpose of this synthetic route was to produce monodisperse cross-linked nanospheres.

Figure 25:
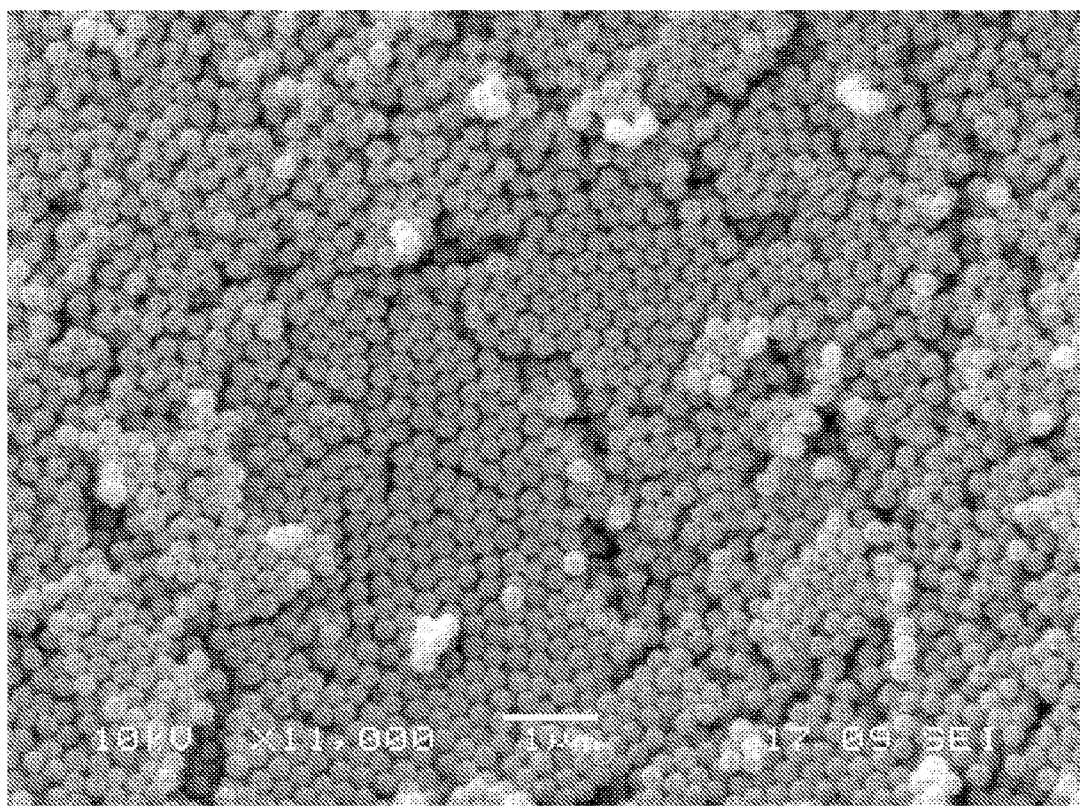
FIG. 25 shows a SEM micrograph of PMMA nanoparticles synthesized via boiling temperature soap-free emulsion polymerization, according to an embodiment of the present invention.

In brief, cross-linked PMMA nanospheres were synthesized via boiling temperature soap-free emulsion polymerization of methyl methacrylate (MMA) using potassium persulfate (KPS) as the initiator and ethylene glycol dimethacrylate (EGDMA) as the cross-linker. Resulting nanospheres were subjected to post-synthesis centrifugation for separation of supernatant and cleaning, followed by lyophilization for drying of the nanospheres. This technique allows for the synthesis of monodisperse nanospheres, reaching almost complete conversion after 2 hours of reaction. Beads that were synthesized range in size from 300 to 330 nm, as illustrated in the micrograph of FIG. 25.

The synthesis is carried out in a 1000 mL three-necked flask filled with 800 mL DI water and a mixture of 50 mL methyl methacrylate (MMA) and ethylene glycol dimethacrylate (EGDMA) (at varying concentrations 10-28%). The mixture is stirred at high speed and the temperature is raised to reflux. After the medium had boiled for 5 minutes potassium persulfate (KPS) is added (0.8 g for 0.10 wt %) and the temperature is maintained at 100° C. for 2 hours after the addition of the initiator. The mixture is subjected to centrifugation steps for removal of supernatant followed by cleaning with water and methanol. The particles are dried by lyophilization during 48 hours and are stored in desiccator.

Example 20

Surface Modification of Cross-Linked PMMA Nanospheres

This Example describes the surface modification of the cross-linked PMMA nanospheres described in Example 19, supra. Based on the findings discussed above in the Background of the Invention Section with respect to the inefficient modification of nanosphere surfaces, a more efficient method that would allow for a higher degree of surface modification was sought, and is described herein. Ideally, a chemical structure containing a hydroxyl group at one end of the chain and an amine group at the other end was envisioned, thus this structure could be directly attached to the surface of the beads via the carboxylic acid group formed under hydrolysis of the methyl ester groups present at the end of the PMMA chains. This idea led to the development of a new synthetic pathway for modification of the surface of PMMA nanospheres and grafting of nanospherical PMMA brushes. This novel method is described in detail in the following four different steps.

Step 1: Hydrolysis of Methyl Ester Groups

Direct coupling to methyl esters is often low yielding and requires harsh reaction conditions; therefore, hydrolysis to the corresponding carboxylic acid can simplify synthetic routes. Consequently, hydrolysis of the surface methyl esters of the PMMA structure was necessary before proceeding with further modification of the beads. Several techniques are well described in the literature for hydrolysis of methyl esters, most of them using lithium hydroxide (LiOH), potassium hydroxide (KOH) or, most recently, trimethyltin hydroxide ($Me_3SnOH$). LiOH hydrolysis was chosen based on observations from the literature. Several studies employing LiOH for hydrolysis of methyl ester groups performed the reactions at room temperature using dichloromethane (DCM) as solvent medium or other typical solvent mixtures such as THF/$MeOH/H_2O$ (3:1:1) or $THF/H_2O$ (9:1) while stifling from 12-24 hours. For the hydrolysis of the PMMA surface methyl esters, THF was used as the solvent, and the reaction was performed at room temperature for 24 hours. The reaction was expected to proceed in THF due to the good solubility of PMMA in this solvent. Reacting 1 g of PMMA nanospheres with a 1 M solution of LiOH (21 mmol) in THF (21 mL) stirred at room temperature for 24 hours hydrolyzed 30% of the functional groups, as assessed by $^1$H NMR. This percentage is within the expected range considering that some of the ester groups might be shielded inside the cross-linked beads.

Briefly, in large scale, the hydrolysis reaction was carried out in a 1000 mL three-necked flask (evacuated and purged with argon) in which 10 grams of LiOH was mixed with 420 mL of THF and stirred until complete dissolution was reached. 20 grams of PMMA cross-linked nanospheres synthesized via boiling temperature soap-free emulsion polymerization was added to the flask containing the 1 M LiOH solution in THF. The flask was resealed and argon purged, and the mixture was stirred for 24 hours at room temperature. The product workup required centrifugation for separation of supernatant (THF), followed by vacuum filtration for rinsing with water and HCl solution for removal of residual LiOH. After separation and purification, the particles were dried in vacuum oven at 45° C. for 24 hours and stored in dessicator. Schematic 1 below illustrates the carboxylic acid structure resulting from hydrolysis with LiOH.

Schematic 1 - Hydrolysis of methyl ester groups from cross-linked PMMA nanospheres with LiOH and formation of carboxylic acid.

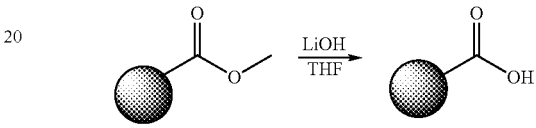

Step 2: Formation of 2-aminoethyl Acrylate Compound

Step 2 was developed following successful cleaving with LiOH. The primary idea was to obtain a chemical structure containing simultaneously an amine group at one end and a double bond at the other end of the chain, thus this structure could be directly attached to the surface of the beads via the carboxylic acid group formed in step 1.

In this step, coupling of N-tBoc protected aminoethanol with acryloyl chloride to form an amine was first performed. Schematic 2 below shows the scheme for the reaction of N-tBoc protected aminoethanol with acryloyl chloride to yield N-tBoc protected 2-aminoethyl acrylate.

Schematic 2 - Steps for formation of 2-aminoethyl acrylate.

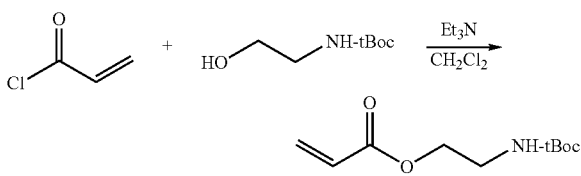

The reaction between N-tBoc protected aminoethanol and acryloyl chloride was observed to occur quickly. The basic reaction was developed by reacting 0.011 mol of acryloyl chloride (0.89 mL) with 0.011 mol of N-tBoc protected aminoethanol (1.7732 mL) in dichloromethane (5 mL). One equivalent of triethylamine (0.011 mol) was added as an HCl scavenger. The reaction was stopped when TLC confirmed no presence of unreacted reagents in the product (approximately 5 minutes after the addition of the reagents). The reaction was performed under argon and an ice bath was used during the addition of the scavenger to avoid overheating.

After completion of the reaction, the post-synthesis treatment involved a series of steps including: 1. washing with 1 M HCl for removal of unreacted triethylamine; 2. washing with water (3×); 3. filtration; 4. drying over magnesium sulfate; 5. rotary evaporation.

After isolation of the product, the tBoc protecting groups were removed by redissolving the mixture in dichloromethane followed by the addition of trifluoroacetic acid (TFA) under argon. This reaction was carried out for 5 hours. The reaction mixture was subjected to rotary evaporation for removal of butyl alcohol generated by hydrolysis of the protecting groups. The dried aminoethyl acrylate product (in crystalline form) was stored in a desiccator.

Schematic 3 below shows the final 2-aminoethyl acrylate product obtained with this procedure. Briefly in large scale, the reaction was performed using a 500 mL one-necked flask, which had the weight recorded and was evacuated and purged with argon. 100 mL of dichloromethane was added to the flask. The flask was placed in an ice bath to avoid excessive heating during the addition of the reagents. 17.8 mL of acryloyl chloride was added using a syringe, followed by the addition of 35.8 mL of N-tBoc protected aminoethanol and 30.6 mL of triethylamine. The mixture was stirred at room temperature for 1 hour. For the first workup the product was poured into a 500 mL separation funnel and was washed twice with a 1M HCl solution (50-100 mL each time). This procedure will remove the residual triethylamine left in the product. The product was also washed twice with water and was dried over magnesium sulfate. Evaporation was performed and the yield was recorded. For removal of the tBoc protecting groups from aminoethyl acrylate, the product was redissolved in 100 mL of dichloromethane and mixed with 100 mL of TFA. The mixture was stirred for 5 hours at room temperature under argon. After reaction completion, the content of the flask was evaporated until the product crystallized. The molecular weight of the aminoethyl acrylate synthesized using this protocol is 115 g/mol ($C_5H_9O_2N$).

Schematic 3 - Resulting aminoethyl acrylate compound after deprotection.

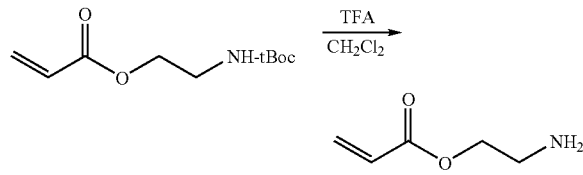

Step 3: Coupling of the PMMA Nanospheres Surface Carboxylic Acid with 2-aminoethyl Acrylate Following confirmation of removal of N-tBoc protecting groups by $^1$H NMR, coupling of aminoethyl acrylate with the carboxylic acid (hydrolyzed PMMA particles) was performed. For this reaction, 28-30% hydrolysis of methyl ester groups was observed based on $^1$H NMR calculations. The amount of PMMA to be used for a desired molar concentration of hydrolyzed monomer was calculated considering 28% hydrolysis. Carbonyldiimidazole (CDI, 1.1 mol equivalents) was used as the coupling agent. CDI was mixed with dimethylformamide (DMF) and the solution was stirred for 30 minutes and reserved for mixing with the other reagents. 1 molar equivalent of the aminoethyl acrylate was transferred to a three-necked flask and mixed with hydrolyzed PMMA swollen in DMF. The solution containing CDI was added to the flask, and the coupling reaction was carried out at room temperature for 24 hours. The post-synthesis treatment included precipitation of the product via centrifugation to remove the organic phase. The particles were redispersed in water and vacuum filtered. The product was washed with water and methanol 3 times.

Schematic 4 below illustrates the resulting structure from the coupling step. Note the carbon-carbon double bond added at the end of the chain, which will act as the initiating site for the free radical polymerization of PMMA brushes.

Briefly in large scale, the reaction was performed in a 500 mL one-necked flask. 6.48 g of the aminoethyl acrylate product synthesized in step 2 was added to flask, which was evacuated and purged with argon. In a separate beaker, 9.1 g of CDI was mixed with 100 mL DMF and stirred for 30 minutes. In a separate flask, 18.2 g of the LiOH hydrolyzed PMMA (considering 28% hydrolysis) was swollen with 150 mL DMF under stifling during 30 minutes. After 30 minutes, the CDI/DMF mixture was added to the flask containing the aminoethyl acrylate and the swollen PMMA/DMF mixture was also transferred to the flask containing the mixture CDI/DMF/aminoethyl acrylate. After purging with argon, the reaction was carried out for 24 hours at room temperature. Product workup included centrifugation for removal of the remaining organic phase, redispersion in water, vacuum filtration and rinsing with water and methanol. The particles were dried in vacuum oven at 45° C. for 24 hours and the product was stored in a dessicator.

Schematic 4 - Coupling between carboxylic acid groups and aminoethyl acrylate compound.

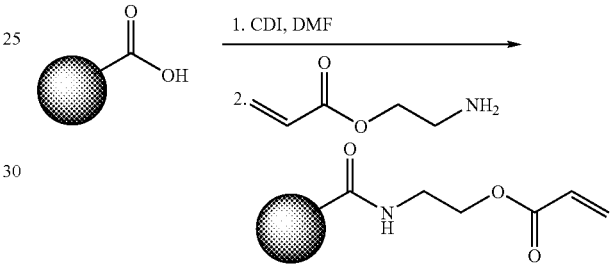

Step 4: Grafting of PMMA Nanospherical Polymer Brushes

This step relates to the synthesis of PMMA spherical polymer brushes tethered to a cross-linked nanosphere core. The synthesis of the polymer brushes was performed by subjecting the coupled product obtained in step 3 to free radical graft copolymerization with MMA in water suspension. Brushes of different molecular weights can be synthesized by variations in the concentration of monomer and initiator feeded. Ideally, a low concentration of monomer should be used (below 10 wt %) to avoid the gel effect in solution, and concentrations of initiator should vary from 0.1 to 1.0 wt %. Higher concentrations of initiator increase the likelihood of residual initiator left on the surface of the particles.

For this procedure, a three-necked flask was equipped with condenser, addition funnel and thermometer. The modified particles were dispersed in water and added to the flask. The flask was again evacuated and argon started. The mixture was let stifling until temperature equilibration at 70° C. When the temperature reached 70° C. the initiator potassium persulfate (KPS), in concentrations varying from 0.1 to 1.0 wt %, was added, and the addition of the monomer (MMA), in concentrations varying from 2 to 5 wt %, was started immediately to avoid particle cross-linking. The reaction was performed for 8 hours. Post-synthesis treatment involved vacuum filtration and washing steps with water and methanol. After filtration the particles were dried in vacuum oven at 70° C. for decomposition of possible residual initiator present in the particles.

Schematic 5 gives the structure of the grafted brush on the modified surface of PMMA nanospheres. Syntheses at different combinations of initiator and monomer concentrations were attempted in order to verify the molecular weight of grafted brushes.

Table 3 gives the molecular weight of brushes synthesized at different conditions in comparison to the molecular weight of brushes obtained with the method previously employed and also discussed in this disclosure.

Briefly in large scale, the reaction was performed in a 1000 mL three-necked flask charged with 720 mL of water and 9 g of the coupled product synthesized in step 3. The flask was sealed under vacuum and purged with argon. The temperature of the medium was raised to 70° C. while stirring. The addition funnel was filled with 37.5 mL of MMA. After the temperature reached 70° C., 2.88 g of KPS were added to the flask. The flask was again sealed, evacuated quickly and purged with argon. Immediately after the addition of the initiator, MMA was added dropwise and the mixture was reacted for 8 hours. Post-synthesis treatment included vacuum filtration and washing steps with water and methanol. This protocol referred to a fixed concentration of monomer and initiator of 5 wt % MMA and 0.4 wt % KPS, respectively. The concentrations were changed accordingly for different combinations of initiator and monomer.

Schematic 5 - Grafting reaction via free radical polymerization of MMA with KPS.

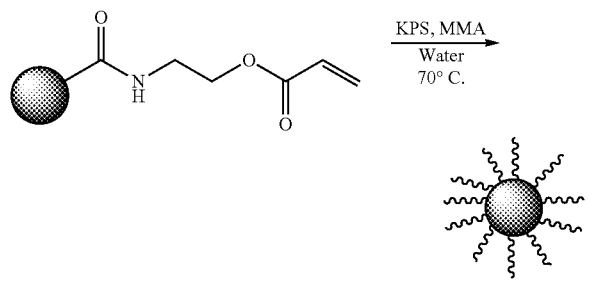

TABLE 3

Weight average molecular weight ($M_w$) and number average molecular weight ($M_n$) obtained for brushes synthesized with different combinations of monomer (MMA) and initiator (KPS).

| Composition [wt % MMA]/[wt % KPS] | Jayachandran modification method[1] | | LiOH methoxy ester cleaving/coupling aminoethanol | |
|---|---|---|---|---|
| | $M_w$ (g/mol) | $M_n$ (g/mol) | $M_w$ (g/mol) | $M_n$ (g/mol) |
| 5 wt % MMA/0.4 wt % KPS | 146300 | 104300 | 312000 | 229900 |
| 5 wt % MMA/0.8 wt % KPS | 33440 | 28870 | 180000 | 124500 |
| 4 wt % MMA/1.0 wt % KPS | 51300 | 47400 | 217050 | 150000 |
| 2 wt % MMA/0.4 wt % KPS | NA* | NA* | 110600 | 80620 |

*Data not available

It is important to point out that the objective was to synthesize chains with molecular weights in the range 80,000-100,000 g/mol, therefore the composition with 2 wt % MMA with 0.4 wt % KPS showed the right molecular weight for the preparation of the cements. Cements prepared at 5 wt % MMA exhibited high viscosity and difficult mixing due to the high molecular weight of the grafts.

Example 20

Preparation of Two-Solution Bone Cements with PMMA Brushes

This Example describes the preparation of two-solution bone cements with PMMA brushes described in the previous Example, where the linear portion of the powder was completely substituted by the nanospherical PMMA brushes.

First, the desired ratio of brush (P) to monomer (M) was determined (P:M ratio). MMA was added to two graduated cylinders and the desired concentration of benzoyl peroxide (BPO) initiator and dimethyl p-toluidine (DMPT) activator was determined and these components were added to the monomer from the two graduated cylinders. The monomer mixture containing BPO or DMPT was transferred to one side of a polypropylene cartridge followed by the addition of the PMMA brush. The cartridges were sealed, vigorously agitated by hand and placed in a rotating drum mixer for 18 hours. Following mixing, the cartridges were stored upright at 4° C. The solutions can be mixed through a static nozzle.

For testing of viscosity, non-setting cement solutions were prepared by simply mixing the brush particles with monomer and mixing the solution for 18 hours. Testing of setting and non-setting cements was only performed after 3 days of preparation of the cement to ensure complete swelling. For the preparation of setting cements a concentration of initiator BPO of 1.25 g/100 mL MMA with a concentration of initiator DMPT of 1.4 mL/100 mL MMA was used.

Cements prepared with brushes synthesized at a composition of 2 wt % MMA and 0.4 wt % KPS exhibited adequate handling and easy mixing through a static nozzle after 24 hours of mixing.

Cements containing this brush composition were prepared a P:M ratios of 1:1, 1.1:1, 1.2:1 and 1.3:1 for comparison with nanospheres-containing cement and the standard cement formulation (TSBC). At a P:M ratio of 1:1 the viscosity was very low and the cement had a more "sticky-like" handling than when containing a mixture of nanospheres and linear polymer. The cement prepared at a P:M ratio of 1.2:1 showed adequate handling and viscosity in the range of the standard formulation (P:M 0.9:1).

Figure 26:
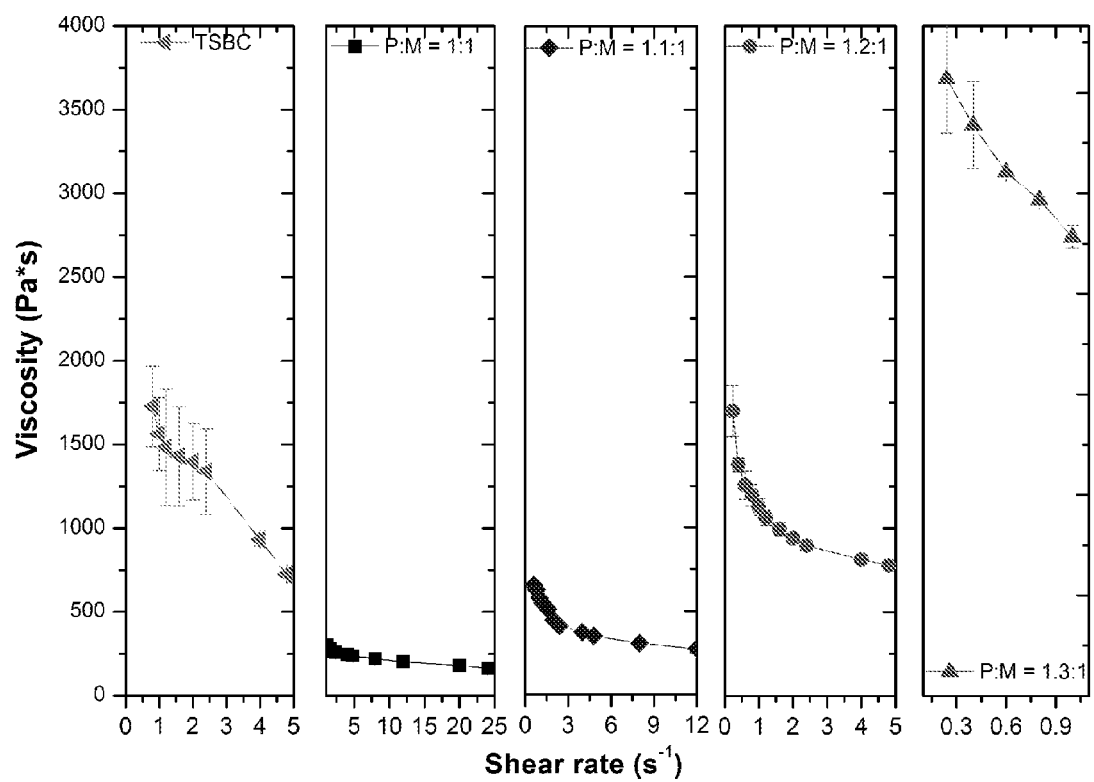
FIG. 26 shows a graphical comparison of brush cement TSBC viscosity with the viscosity of the standard formulation (TSBC) prepared at increasing P:M ratios, according to an embodiment of the present invention.

FIG. 26 shows a graphical comparison of brush cement viscosity at increasing P:M ratios with the viscosity of the standard formulation (TSBC).

Figure 27:
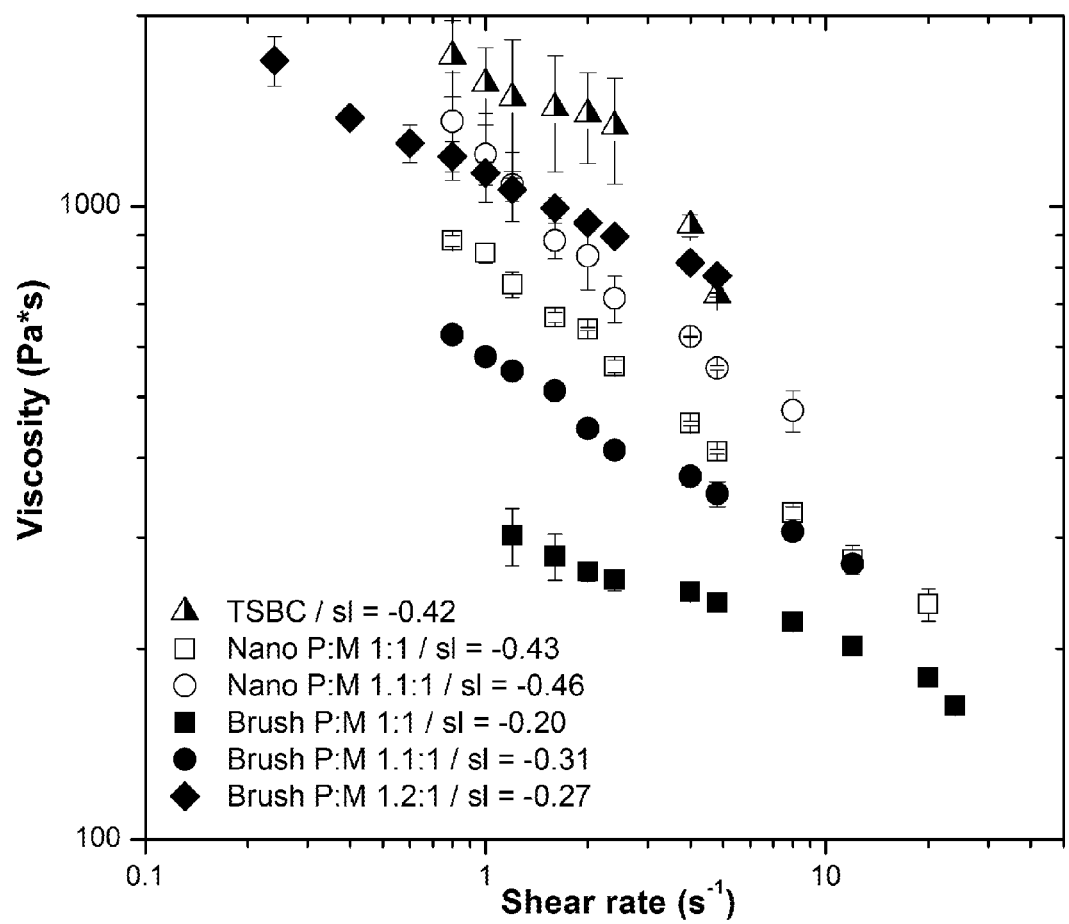
FIG. 27 shows a graphical comparison of Log-log viscosity of TSBC, 1'-TSBC and brush-TSBC at different P:M ratios, according to an embodiment of the present invention.

The viscosity of the brush cements was compared with the viscosity of nanospheres and standard cement in a log-log scale in FIG. 27. From this Figure it is notable that brush cements at P:M ratios of 1:1 and 1.1:1 (dark symbols) exhibited significantly lower viscosities than nanospheres cements ($\eta$-TSBC) at the same compositions (open symbols). It was also observed that the brush cements are less susceptible to shear-thinning than the standard and nanospheres cements, as indicated by smaller slopes. The fact that brush cements exhibited lower pseudoplastic behavior was expected and can be explained by considering that the entangled brush chains are not as susceptible to alignment in the direction of the shear force as when having random chains, which are free to move in the direction of the flow. The mechanical properties of these cements have also been tested in compression and flexural modes.

Preliminary data point to a significant decrease in the compressive and flexural strength of the two-solution cements when brushes are added. A hypothesis that might explain this trend is the observation that the molecular weight of the grafts is lower than the molecular weight of the polymerized chains in the cement matrix, therefore the matrix chains are not able to penetrate and fully swell the brush structure, which leads to a short-range interaction between brushes and precipitation or formation of clumps in the matrix. This phenomenon is described as a dry-brush regime. Brush structures interacting with one another will not permit entanglements with the polymerized chains in the cement matrix, therefore reducing the strength of the material. In addition, clumps or precipitates may act as stress concentrators in the cement matrix.

Measurements of molecular weight of cured cements prepared with brushes and the standard formulation indicated a significant increase in the molecular weight of the fully cured cements in comparison to the starting materials, indicating a higher molecular weight of the interbead-polymer matrix. The maximum polymerization temperatures of brush-containing cements are significantly lower (approximately 65° C.) in comparison to the standard formulation (approximately 95° C.) and is in the range measured for nanospheres-containing cements. Likewise, post-cure residual monomer is significantly reduced when PMMA brushes substitute the linear PMMA in the cement mixture, containing approximately 2.5 wt % residual MMA in average in comparison to 12.5 wt % residual monomer measured for the standard formulation.

In summary this new protocol/method showed satisfactory results for the efficient modification of the PMMA nanospheres for grafting of nanospherical brushes at high densities, leading to the preparation of cements with optimal viscosity at higher P:M ratios and with adequate physical and chemical properties.

Example 21

$^1$H NMR of Reaction Steps

This Example describes additional proton nuclear magnetic resonance data that support the fact that more initiating sites are added to the surface of the nanospheres, following the method of grafting PMMA brushes on cross-linked PMMA nanospheres according to an embodiment of the present invention. This led to a higher density of grafts attached to the surface of the cross-linked PMMA nanospheres.

FIG. 28a-c shows the $^1$H-NMR results for the first and third steps of the modification reaction ("hydrolysis" and "coupling" steps) of the surface of PMMA nanospheres and the final step for grafting of PMMA brushes, as described supra. The arrows marked with "R" indicate peaks associated with PMMA, while the arrows marked with "B" indicate peaks associated with the aminoethyl acrylate. The chemical structure of the hydrolyzed PMMA nanospheres is illustrated on the top left of the spectra and it is assigned to its corresponding chemical shifts in the spectrum (a).

Spectrum (a) illustrates the resulting peaks from the hydrolysis with LiOH, from which it was concluded that approximately 30% of the methyl ester groups have been hydrolyzed from the surface of the beads forming carboxylic acid groups. This percentage of modification was obtained by comparing the integrated areas corresponding to peaks (a) and (c, e). The hydrolysis allowed for coupling with 2-aminoethyl acrylate, as shown in (b). The peaks between δ 6.4 and 5.8 ppm in spectrum (b) are consistent with the double bonds from 2-aminoethyl acrylate. The spectrum also showed a small amount of impurities. The results displayed in FIG. 28c confirmed successful grafting of brushes on the surface of the coupled product (b), as indicated by the absence of the double bond peaks in the final product. The spectrum corresponding to the grafted product (c) exhibited matching peaks with ungrafted PMMA (a), confirming the grafting of PMMA at the initiation sites provided by the intermediate step (b).

Figure 28:
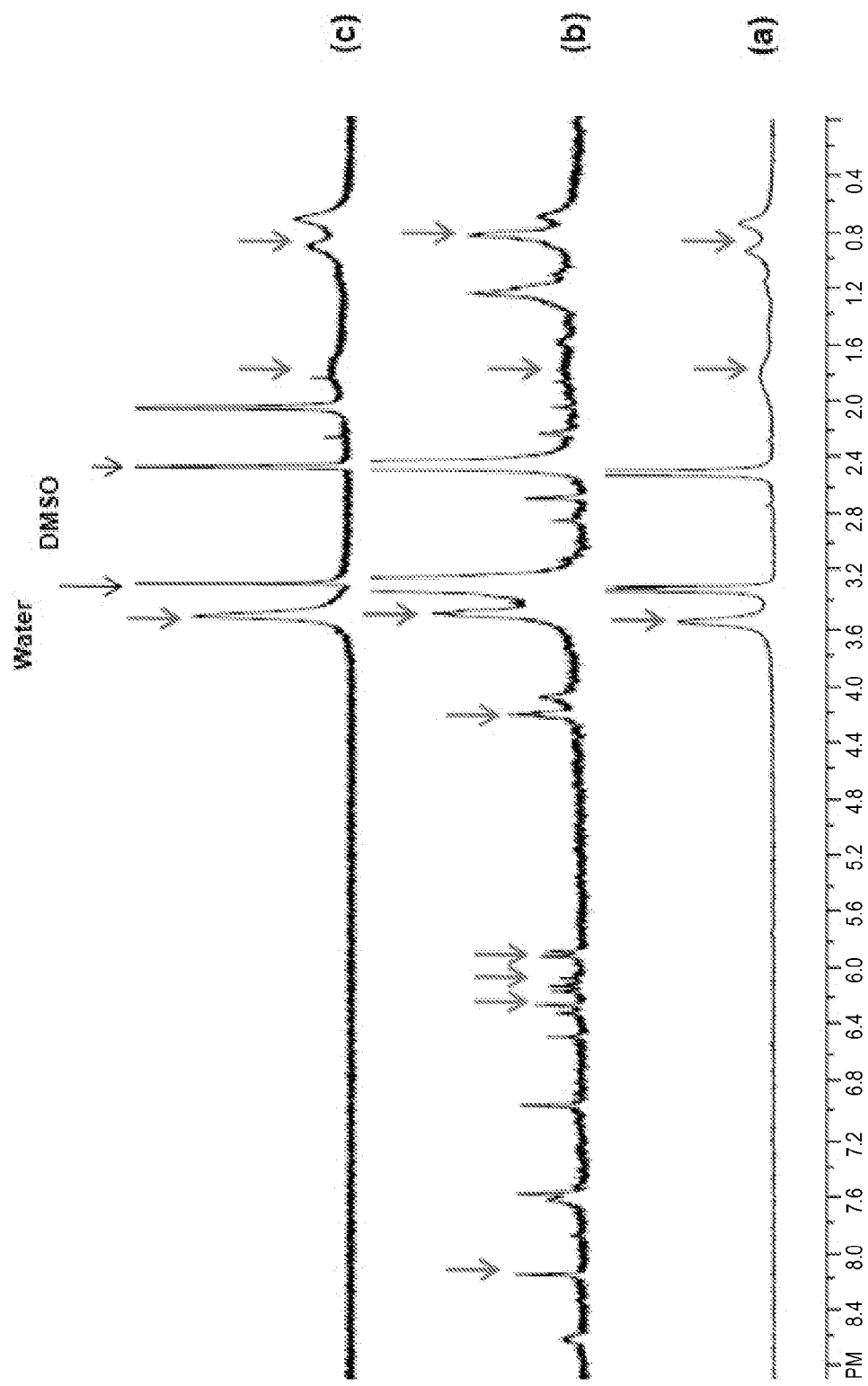
FIG. 28 shows $^1H$ NMR spectra of (a) LiOH hydrolyzed PMMA, (b) 2-aminoethyl acrylate coupled with LiOH PMMA and (c) grafted PMMA brushes, according to an embodiment of the present invention.

The spectrum corresponding to the coupled compound (FIG. 28b) shows the result for the crude product, therefore justifying the presence of impurities. However, these impurities were successfully removed during the purification of the grafted particles, as demonstrated in the spectrum of FIG. 28c. Impurities are a byproduct of the imidazole and the carbonyldiimidazole used during the synthesis of the 2-methyl acrylate compound. All of these spectra were taken in DMSO. The water that comes along with the DMSO as an impurity is also indicated in the spectra of FIG. 28.

Example 22

Methodology Comparison

This Example relates to a comparison between the methodology of an embodiment of the present invention ("new modified") and the previous method ("old modified") following the mechanism proposed by Jayachandran and Chatterji (Jayachandran K N, Chatterji. Synthesis of dense brush polymers with cleavable grafts. European Polym J 2000; 36:743-749) is shown in FIGS. 29 and 30.

Figure 29:
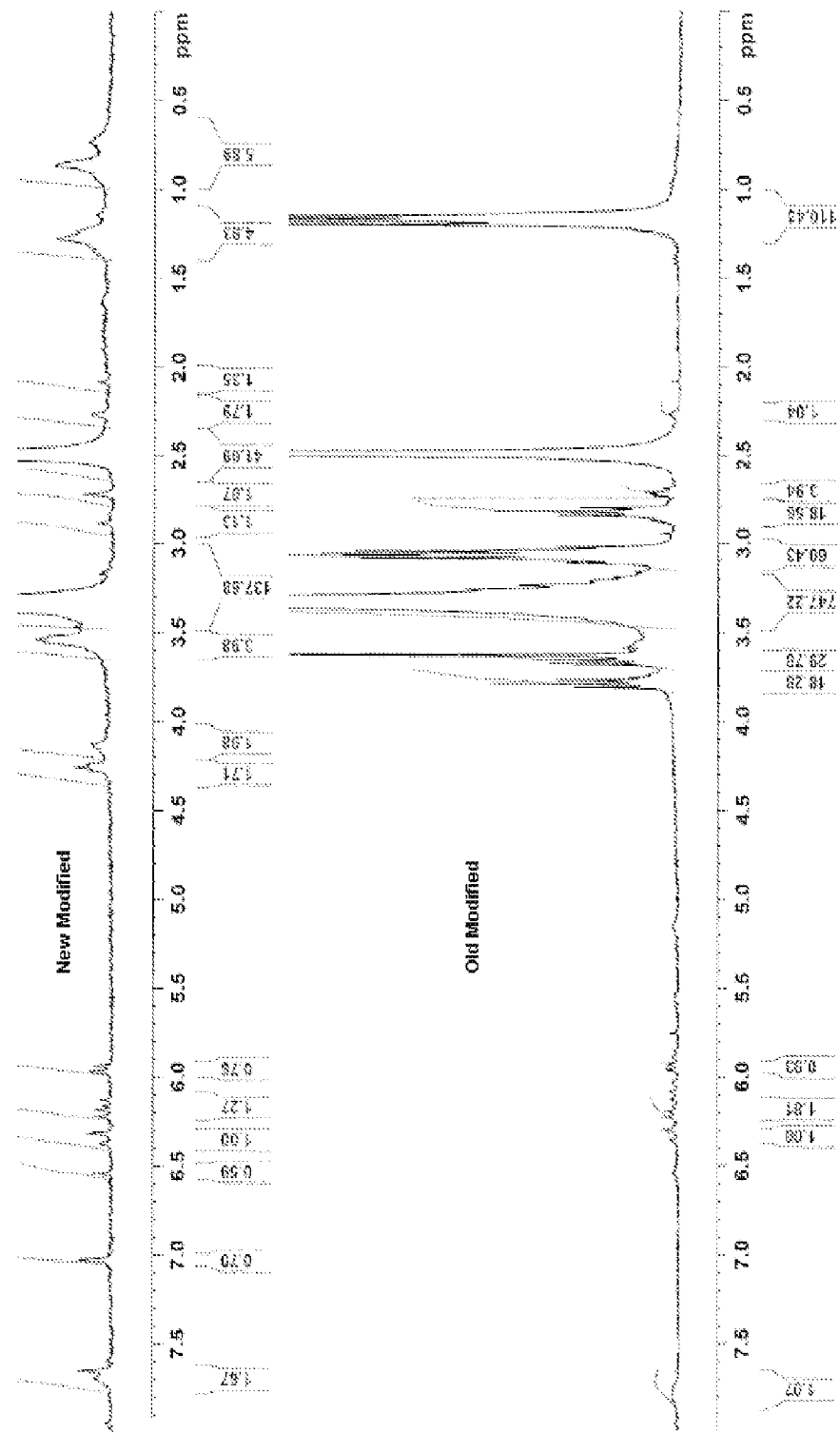
FIG. 29 shows $^1H$ NMR spectra comparing LiOH hydrolyzed PMMA coupled with 2-aminoethyl acrylate (new modified product according to an embodiment of the present invention) with ethanolamine-modified PMMA coupled with acryloyl chloride (old modified product).

FIG. 29 shows a comparison between the coupled product (aminoethyl acrylate and LiOH hydrolyzed PMMA) (labeled new modified) with the coupled product from the reaction with acryloyl chloride (labeled old modified) and ethanolamine-modified PMMA. From the figure, it is evident that the product resulting from the previous methodology contained a large fraction of impurities, and a small fraction of double bonds, as demonstrated by the low relative areas of the peaks between δ 6.4 and 5.8 ppm. Consequently the coupled product obtained by the previous method, did not permit efficient PMMA grafting. It is also difficult to discern in this spectrum methacrylate associated shifts due to the presence of unknown peaks. On the contrary, PMMA associated peaks and peaks corresponding to double bonds from the aminoethyl acrylate compound are clearly present on the spectrum of the coupled product (new modified product according to an embodiment of the present invention), as previously highlighted in FIG. 28b.

Figure 30:
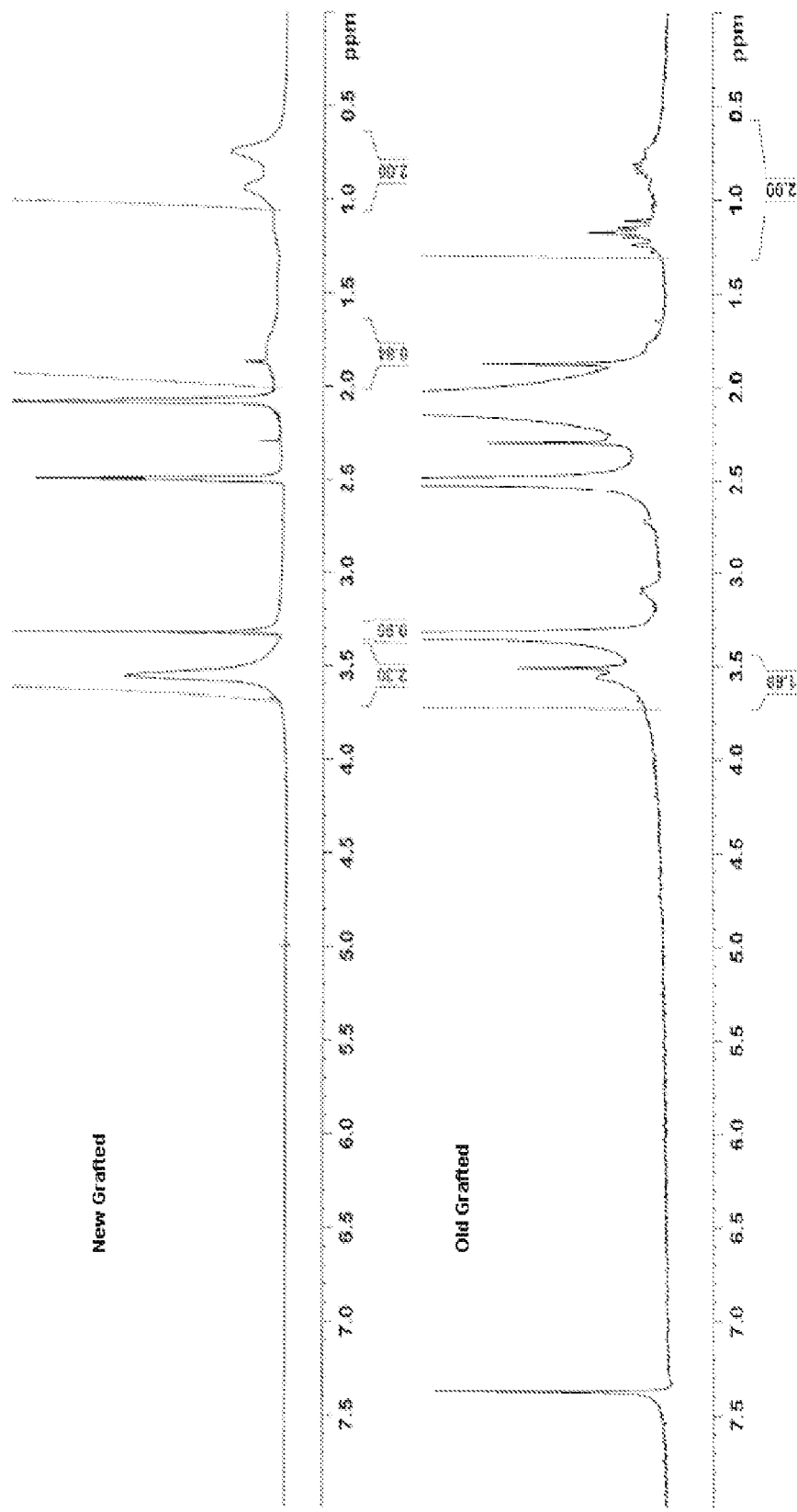
FIG. 30 shows results of grafting of nanospherical brushes via the new methodology (new grafted according to an embodiment of the present invention) compared to the previous synthetic pathway employed (old grafted).

FIG. 30 confirmed that the percentage of methacrylate groups (regions indicated by arrows) was significantly smaller (labeled old grafted) in comparison to the percentage of grafting achieved following the new methodology (labeled new grafted). The arrows indicate peaks associated with PMMA. The percentage of methacrylate groups obtained was higher with the new methodology, as illustrated by the arrows, giving evidence of higher grafting efficiency.

Brush Density

Figure 31:
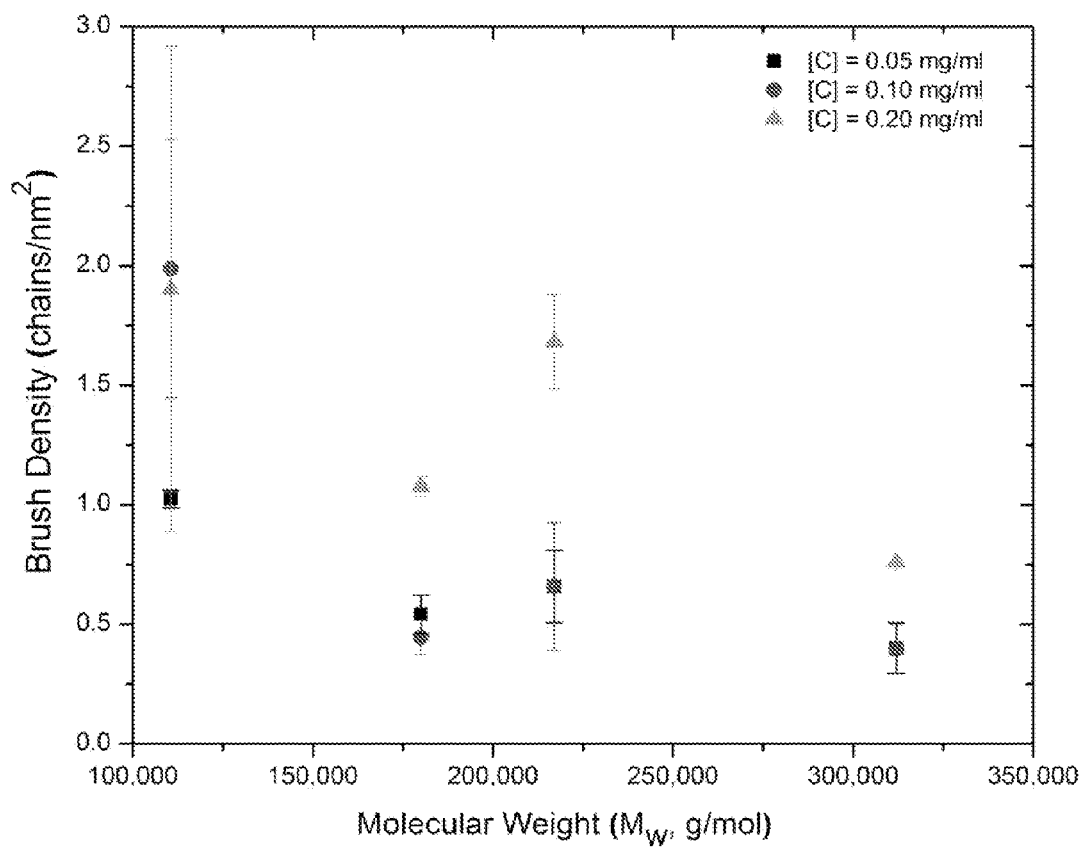
FIG. 31 shows the brush density ($\sigma$) calculated from measurements of the hydrodynamic radii ($R_h$) and molecular weight (number average molecular weight, $M_n$) of the brush structures, plotted as a function of molecular weight of each brush composition, according to an embodiment of the present invention.

FIG. 31 shows the calculated brush densities for each composition prepared by the "new modified" process referenced above, according to an embodiment of the present invention. Solutions were prepared at three different concentrations of brushes in tetrahydrofuran (THF), and obtained from dynamic light scattering experiments in batch mode with a quasi-static light scattering detector (QELS, Wyatt). Note the high graft density obtained for the brush composition with low molecular weight, 2 wt % MMA/0.4 wt % KPS, followed by a significant decrease in density with increasing molecular weight compositions (Graft density is maximized for the lowest graft molecular weight, 2 wt % MMA/0.4 wt % KPS ($M_w$=110,600 g/mol), while minimized for the highest graft molecular weight, 5 wt % MMA/0.4 wt % KPS ($M_w$=312,000 g/mol)). Note the good correlation between the data points at the concentrations 0.05 and 0.10 mg/ml. Significantly lower values of grafting density were observed for brushes synthesized with 5 wt % MMA, most remarkably for the highest molecular weight composition with 5 wt % MMA/0.4 wt % KPS ($M_w$=312,000 g/mol). This result is an indication that the high molecular weight growing chains might have sterically blocked the access to the neighboring initiating sites on the PMMA core. According to Borukhov et al. (Borukhov I and Leibler L. Enthalpic stabilization of brush coated particles in a polymer melt. Macromolecules 2002; 35:5171-5182) at low grafting densities the grafted chains become isolated from each other and form a kind of semispherical cap, resembling the shape of a mushroom. These are referred to as the swollen mushrooms regime or dry mushrooms regime. This collapsed mushroom conformation may end up blocking the access of initiating sites on the core surface. An increase in σ is expected to result in larger stretching of tethered chains leading to enhancements in both the brush density and thickness.

The graft density showed an exponentially decreasing trend with increasing molecular weight of grafts with correlation coefficient values of $R^2=0.70$ for 0.05 mg/ml, $R^2=0.93$ for 0.10 mg/ml and $R^2=0.90$ for 0.20 mg/ml. This trend may confirm the observation that growing chains of high molecular weights may have blocked the access to other initiating sites, which in turn resulted in a collapse of the brushes on the surface of the core particle due to the lower density of grafts present.

Multi-Solution Bone Cement Compositions

FIG. 32 is a table that shows multi-solution bone cement compositions, according to an embodiment of the present invention. This table shows calculations for the linear polymer to monomer ratio of bone cement compositions of an embodiment of the present invention. These calculations demonstrate that there are many multi-solution bone cement compositions of an embodiment of the present invention that have a PI:M ratio under 0.5:1.

While several embodiments of the invention have been discussed, it will be appreciated by those skilled in the art that various modifications and variations of the present invention are possible. Such modifications do not depart from the spirit and scope of the claimed invention.

What is claimed is:

1. A method of grafting Polymethyl methacrylate (PMMA) brushes on cross-inked PMMA nanospheres comprising the steps of:
   a. performing a hydrolysis reaction of surface methyl ester groups of said cross-linked PMMA nanospheres to form surface carboxylic acid groups of said cross-linked PMMA nanospheres;
   b. forming a 2-aminoethyl acrylate compound;
   c. coupling said surface carboxylic acid groups of said cross-linked PMMA nanospheres with said 2-aminoethyl acrylate compound to form a coupled compound with an initiating site; and
   d. grafting said PMMA brushes onto said initiating site.

2. The method of claim 1, wherein the step of performing a hydrolysis reaction further comprises the step of reacting said surface methyl ester groups of said cross-linked PMMA nanospheres with lithium hydroxide, 3. The method of claim 2, wherein the step of reacting said surface methyl ester groups of said cross-linked PMMA nanospheres with lithium hydroxide further comprises a step of reacting said surface methyl ester groups of said cross-linked PMMA nanospheres with lithium hydroxide in a THF solution.

4. The method of claim 1, wherein the step of forming a 2-aminoethyl acrylate compound further comprises the step of reacting N-tBoc protected aminoethanol with Acryloyl chloride.

5. The method of claim 4, wherein the step of reacting N-tBoc protected aminoethanol with Acryloyl chloride further comprises reacting N-tBoc protected aminoethanol with Acryloyl chloride in a dichloromethane solution to form a N-tBoc protected 2-aminoethyl acrylate compound.

6. The method of claim 5, wherein the step of forming a 2-aminoethyl acrylate compound further comprises a step of isolating said N-tBoc protected 2-aminoethyl acrylate compound.

7. The method of claim 6, wherein the step of forming a 2-aminoethyl acrylate compound further comprises a step of removing the tBoc protecting group by hydrolysis from said N-tBoc protected 2-aminoethyl acrylate compound to form said 2-aminoethyl acrylate compound.

8. The method of claim 1, wherein the step of coupling further comprises a step of using carbonyldiimidazole as a coupling agent.

9. The method of claim 8, wherein the step of coupling further comprises a step of mixing carbonyldiimidazole with dimethylformamide.

10. The method of claim 9, wherein the step of grafting said PMMA brushes onto said initiating site further comprises a step of subjecting the coupled compound to free radical graft copolymerization with methyl methacrylate (MMA).

11. The method of claim 10, wherein the step of subjecting further comprises a step of adding said MMA to a water suspension.

12. The method of claim 11, wherein the step of subjecting further comprises a step of adding an initiator to the MMA in the water suspension.

13. The method of claim 12, wherein said initiator is potassium persulfate.

14. The method of claim 13, wherein at least one PMMA brush has a molecular weight of between 80,000 g/mol to 100,000 g/mol.

15. The method of claim 13, wherein the wt % of MMA is about 2 and the wt % of potassium persulfate is about 0.4.

16. The method of claim 1, further comprising a step of synthesizing cross-linked PMMA nanospheres prior to the step of performing.

17. The method of claim 16, wherein the step of synthesizing further comprises a step of boiling temperature soap-free emulsion polymerization of methyl methacrylate (MMA).

* * * * *